United States Patent [19]
Stroman et al.

[11] Patent Number: 4,855,231
[45] Date of Patent: * Aug. 8, 1989

[54] REGULATORY REGION FOR HETEROLOGOUS GENE EXPRESSION IN YEAST

[75] Inventors: David W. Stroman, Bartlesville, Okla.; Paul F. Brust, San Diego, Calif.; Steven B. Ellis, La Jolla, Calif.; Thomas R. Gingeras, Encinitas, Calif.; Michael M. Harpold; Juerg F. Tschopp, both of San Diego, Calif.

[73] Assignee: Phillips Petroleum Company, Bartlesville, Okla.

[*] Notice: The portion of the term of this patent subsequent to Feb. 28, 2006 has been disclaimed.

[21] Appl. No.: 780,102

[22] Filed: Sep. 25, 1985

Related U.S. Application Data

[63] Continuation-in-part of Ser. No. 666,391, Oct. 30, 1984.

[51] Int. Cl.$^4$ .................. C12P 21/00; C12P 21/02; C12N 15/00; C12N 7/00
[52] U.S. Cl. ........................... 435/68; 536/27; 435/70; 435/172.3; 435/255; 435/256; 435/320; 935/27; 935/36; 935/37; 935/56; 935/69
[58] Field of Search ............... 435/68, 172.1, 172.3, 435/255, 256, 320; 536/27; 935/6, 14, 28, 37, 56, 69

[56] References Cited

PUBLICATIONS

Tuite et al., EMBO, vol. 1, pp. 603–608, 1982, "Regulated High Efficiency Expression of Human Interferon-Alpha in *Saccharomyces cerevisiae*."
Bennetzen et al., *J. Biol. Chem.*, vol. 257(6), Mar. 25, 1982, pp. 3018–3025, "The Primary Structure of the *Saccharomyces cerevisiae*-Gene for Alcohol Dehydrogenase 1."
Sibirny et al., Curr. Genet., vol. 8, pp. 107–114, 1984, "Identification of Regulatory Genes of Riboflavin Permeates and α-glucosidase in the Yeast *Pichia guillrermandii*".
Stephien et al., Gene, vol. 24 (2–3), 1983, pp. 289–298, "Synthesis of a Human Insulin Gene, 6. Expression of the Synthetic Proinsulin Gene . . . ".

*Primary Examiner*—Robin Teskin
*Attorney, Agent, or Firm*—J. E. Phillips

[57] ABSTRACT

Novel DNA sequences which are responsive to the presence of methanol, catabolite non-repressing carbon sources and carbon source starvation are provided. In addition, novel constructs including these DNA sequences, as well as transformed organisms therewith are provided. Processes for producing the DNA sequences and constructs of the invention are detailed. The production of polypeptide product under the control of the regulatory regions of the invention is demonstrated.

98 Claims, 27 Drawing Sheets

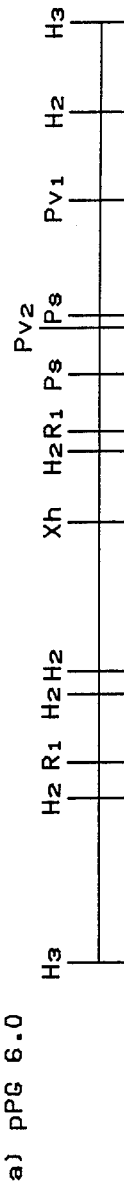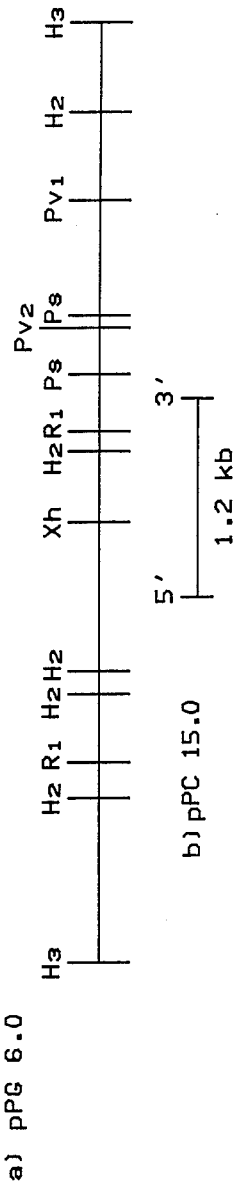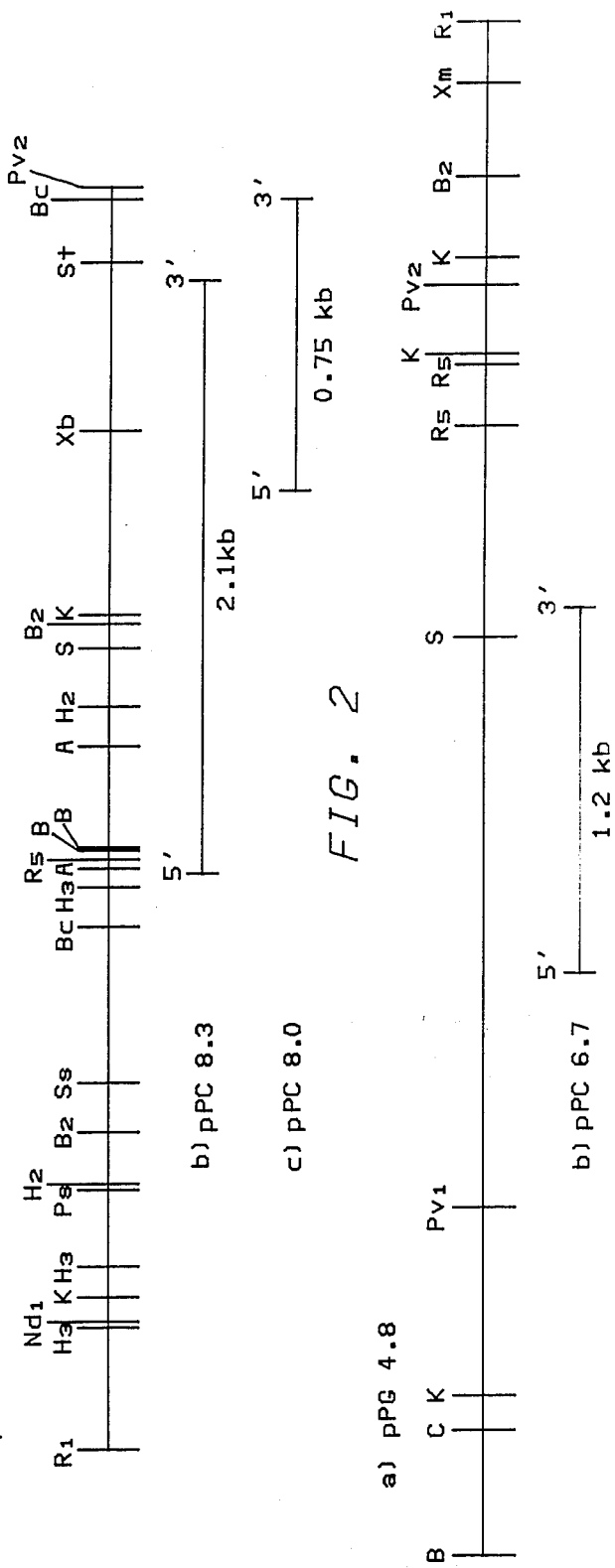

REGULATORY REGION FOR HETEROLOGOUS GENE EXPRESSION IN YEAST

This application is a continuation-in-part of copending application Ser. No. 666,391, filed Oct. 30, 1984.

This invention relates to the field of recombinant DNA biotechnology. In one of its aspects, the invention relates to DNA fragments which regulate the transcription of DNA into messenger RNA, and the initiation and termination of the translation of messenger RNA into protein. In another aspect, the invention relates to expression vectors which incorporate the above-described DNA fragments. In yet another aspect, the invention relates to novel microorganisms transformed with the above-described expression vectors. In a further aspect, the invention relates to the production of polypeptides.

BACKGROUND

As recombinant DNA technology has developed in recent years, the controlled production by microorganisms of an enormous variety of useful polypeptides has become possible. Many eukaryotic polypeptides, such as for example human growth hormone, leukocyte interferons, human insulin and human proinsulin have already been produced by various microorganisms. The continued application of techniques already in hand is expected in the future to permit production by mircoorganisms of a variety of other useful polypeptide products.

The basic techniques employed in the field of recombinant DNA technology are known by those of skill in the art. The elements desirably present in order for a host microorganism to be useful for the practice of recombinant DNA technology include, but are not limited to:

(1) a gene encoding one or more desired polypeptide(s) and provided with adequate control sequences required for expression in the host microorganism, (2) a vector, usually a plasmid, into which the gene can be inserted. The vector serves to guarantee transfer of the gene into the cell and maintenance of DNA sequences in the cell as well as a high level of expression of the above-mentioned gene, and (3) a suitable host microorganism into which the vector carrying the desired gene can be transformed, where the host microorganism also has the cellular apparatus to allow expression of the information coded for by the inserted gene.

A basic element employed in recombinant DNA technology is the plasmid, which is extrachromosomal, double-stranded DNA found in some microorganisms. Where plasmids have been found to naturally occur in microorganisms, they are often found to occur in multiple copies per cell. In addition to naturally occurring plasmids, a variety of man-made plasmids, or hybrid vectors, have been prepared. Included in the information encoded in plasmid DNA is that required to reproduce the plasmid in daughter cells, i.e., an autonomously replicating sequence or an origin of replication. One or more phenotypic selection characteristics must also be included in the information encoded in the plasmid DNA. The phenotypic selection characteristics permit clones of the host cell containing the plasmid of interest to be recognized and selected by preferential growth of the cells in selective media.

The utility of plasmids lies in the fact that they can be specifically cleaved by one or another restriction endonuclease or restriction enzyme, each of which recognizes a specific, unique site on the plasmid DNA. Thereafter, homologous genes, heterologous genes, i.e., genes derived from organisms other than the host, or gene fragments may be inserted into the plasmid by endwise joining of the cleaved plasmid and desired genetic material at the cleavage site or at reconstructed ends adjacent to the cleavage site. The resulting recombined DNA material can be referred to as a hybrid vector.

DNA recombination is performed outside the host microorganism. The resulting hybrid vector can be introduced into the host microorganism by a process known as transformation. By growing the transformed microorganism, large quantities of the hybrid vector can be obtained. When the gene is properly inserted with reference to the portions of the plasmid which govern transcription and translation of the encoded DNA message, the resulting hybrid vector can be used to direct the production of the polypeptide sequence for which the inserted gene codes. The production of polypeptide in this fashion is referred to as gene expression.

Gene expression is initiated in a DNA region known as the promoter region. In the transcription phase of expression, the DNA unwinds exposing it as a template for synthesis of messenger RNA. RNA polymerase binds to the promoter region and travels along the unwound DNA from its 3' end to its 5' end, transcribing the information contained in the coding strand into messenger RNA (mRNA) from the 5' end to the 3' end of the mRNA. The messenger RNA is, in turn, bound by ribosomes, where the mRNA is translated into the polypeptide chain. Each amino acid is encoded by a nucleotide triplet or codon within what may be referred to as the structural gene, i.e., that part of the gene which encodes the amino acid sequence of the expressed product. Since three nucleotides code for the production of each amino acid, it is possible for a nucleotide sequence to be "read" in three different ways. The specific reading frame which encodes the desired polypeptide product is referred to as the proper reading frame.

After binding to the promoter, RNA polymerase first transcribes a 5' leader region of mRNA, then a translation initiation or start codon, followed by the nucleotide codons within the structural gene itself. In order to obtain the desired gene product, it is necessary for the initiation or start codon to correctly initiate the translation of messenger RNA by the ribosome in the proper reading frame. Finally, stop codons are transcribed at the end of the structural gene which cause any additional sequences of mRNA to remain untranslated into peptide by the ribosomes, even though additional sequences of mRNA had been formed by the interaction of RNA polymerase with the DNA template. Thus, stop codons determine the end of translation and therefore the end of further incorporation of amino acids into the polypeptide product. The polypeptide product can be obtained by lysing the host cell and recovering the product by appropriate purification from other microbial protein, or, in certain circumstances, by purification of the fermentation medium in which the host cells have been grown and into which the polypeptide product has been secreted.

In practice, the use of recombinant DNA technology can create microorganisms capable of expressing entirely heterologous polypeptides, i.e., polypeptides not ordinarily found in, or produced by, a given microorganism—so called direct expression. Alternatively, there may be expressed a fusion protein, i.e., a heterologous polypeptide fused to a portion of the amino acid sequence of a homologous polypeptide, i.e., polypeptides found in, or produced by, the wild-type (non-transformed) host microorganism—so called indirect expression. With indirect expression, the initially obtained fusion protein product is sometimes rendered inactive for its intended use until the fused homologous/heterologous polypeptide is cleaved in an extracellular environment. Thus, for example, cyanogen bromide cleavage of methionine residues has yielded somatostatin, thymosin alpha 1 and the component A and B chains of human insulin from fused homologous/heterologous polypeptides, while enzymatic cleavage of defined residues has yielded beta endorphin.

Up to now, commercial efforts employing recombinant DNA technology for producing various polypeptides have centered on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

OBJECTS OF THE INVENTION

An object of our invention is therefore a novel regulatory region responsive to the presence of methanol.

A further object of the invention is a novel catabolite sensitive regulatory region which is responsive to the presence of some carbon sources but which is not responsive to the presence of other carbon sources.

Another object of the invention is a novel regulatory region responsive to carbon source starvation.

Yet another object of our invention is novel vectors capable of expressing an inserted polypeptide coding sequence.

Still another object of our invention is novel yeast strains of the genus Pichia and Saccharomyces.

A further object of the invention is a process for producing polypeptides employing novel yeast strains as described hereinabove.

These and other objects of our invention will become apparent from the disclosure and claims herein provided.

STATEMENT OF THE INVENTION

In accordance with the present invention, we have discovered, isolated and characterized DNA sequences which control the transcription of DNA into messenger RNA and translation of the messenger RNA to give a polypeptide product. The novel DNA sequences of this invention are useful for the production of polypeptide products by (a) yeast strains which are capable of growth on methanol as a carbon and energy source, (b) yeast strains which are capable of growth on glucose, ethanol, fructose and the like; and (c) yeast strains which are capable of growth on glycerol, galactose, acetate and the like.

BRIEF DESCRIPTION OF THE FIGURES

FIG. 1 is a correlation of the relationship between the genomic clone (pPG 6.0) and cDNA clone (pPC 15.0) for protein p76.

FIG. 2 is a correlation of the relationship between the genomic clone (pPG 4.0) and cDNA clones (pPC 8.3 and pPC 8.0) for protein p72 (alcohol oxidase).

FIG. 3 is a correlation of the relationship between the genomic clone (pPG 4.8) and cDNA clone (pPC 6.7) for protein p40.

Figure 4:
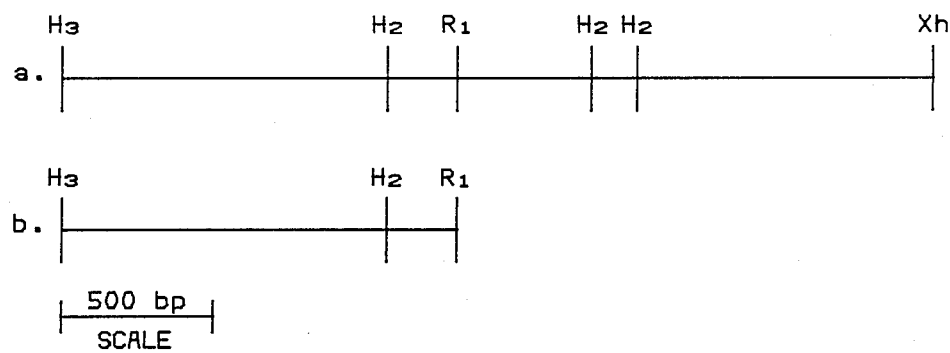
FIG. 4 provides restriction maps of regulatory regions of the invention from clone pPG 6.0.

The following abbreviations are used throughout this application to represent the restriction enzymes employed:

A = AsuII
B = BamHI
$B_2$ = BglII
Bc = BclI
C = ClaI
$H_2$ = HincII
$H_3$ = HindIII
K = KpnI
$Nd_1$ = NdeI
Nr = NruI
Ps = PstI
$Pv_1$ = PvuI
$Pv_2$ = PvuII
$R_1$ = EcoRI
$R_5$ = EcorRV
Rs = RsaI
S = SalI
$S_3$ = Sau3AI
Sc = SacI
Sm = SmaI
Sp = SphI
Ss = SstI
St = StuI
T = TaqI
Th = ThaI
Xb = XbaI
Xh = XhoI
Xm = XmaI In the attached figures, restriction sites employed for manipulation of DNA fragments, but which are destroyed upon ligation are indicated by enclosing the abbreviation for the destroyed site in parentheses.

DETAILED DESCRIPTION OF THE INVENTION

In accordance with the present invention, there is provided a novel DNA fragment comprising a regulatory region responsive to at least one of the following conditions: the presence of methanol, carbon source starvation when cells are grown on some substrates other than methanol, and the presence of non-catabolite repressing carbon sources other than methanol. The regulatory region of the DNA fragment of this invention is capable of controlling the transcription of messenger RNA when positioned at the 5' end of the DNA which codes for the production of messenger RNA. Also included within the scope of our invention are mutants of the above-described DNA fragment.

Further in accordance with the present invention, there is provided a DNA fragment which comprises a regulatory region which is capable of controlling the polyadenylation, termination of transcription and termination of translation of messenger RNA when positioned at the 3' end of the polypeptide coding region which codes for the production of messenger RNA, wherein the transcription and translation of the messenger RNA is controlled by a regulatory region which is responsive to at least one of the following conditions: the presence of methanol, carbon source starvation when cells are grown on some substrates other than methanol and the presence of non-catabolite repressing carbon sources other than methanol. Also included within the scope of our invention are mutants of the above-described DNA fragment.

Still further in accordance with a specific embodiment of the invention, there are provided DNA fragments which direct the incorporation of encoded polypeptide into peroxisomes. Peroxisomes are intracellular bodies present in large amounts in methanol grown yeast cells. These intracellular bodies serve to isolate the incorporated polypeptide product from intracellular fluids and enzymes such as proteases.

In accordance with another embodiment of the invention, genes coding for the production of alcohol oxidase, a protein of about 40 kilodaltons and a protein of about 76 kilodaltons are provided.

In accordance with yet another embodiment of the present invention, plasmids and transformed organisms containing the above-described DNA fragments are provided.

In accordance with still another embodiment of the invention, methods are provided for producing the plasmids and DNA fragments of the invention, as well as heterologous polypeptides, i.e., polypeptides not native to the host organisms.

ISOLATION OF REGULATABLE GENES FROM *PICHIA PASTORIS*

An approximately 20,000 member cDNA library was prepared in *E. coli* with poly A+ RNA isolated from *Pichia pastoris* cells grown on methanol as the sole carbon source (See Example III). The library was screened by hybridization using kinased poly A+ RNA isolated from *Pichia pastoris* grown either in the presence of methanol or ethanol. After several rounds of this plus-minus screening, three distinct, non-homologous cDNA clones were identified as being copies of methanol specific messenger RNA's. These clones were designated as pPC 6.4, pPC 8.0, and pPC 15.0 and were determined to contain inserts of 470, 750 and 1100 nucleotides in length, respectively.

In an attempt to obtain cDNA clones of longer length, a second cDNA library was prepared using milder S1 nuclease digestion conditions than used for the preparation of the first cDNA library and the members of this new library screened individually with $^{32}$P-labeled cDNA clones pPC 6.4, pPC 8.0, and pPC 15.0. As a result, larger cDNA clones were isolated corresponding to cDNA clones pPC 6.4 and pPC 8.0. The larger clones pPC 6.7 and pPC 8.3, were found to contain inserts measuring 1200 and 2100 nucleotides, respectively (See FIGS. 2 and 3). A cDNA clone possessing an insert larger than the 1100 nucleotides for pPC 15.0 has not been observed after screening more than 40,000 cDNA clones.

The isolation of the genomic DNA fragments corresponding to each of these cDNA clones was accomplished by first cutting out and electroeluting from agarose gels *Pichia pastoris* DNA fragments of restriction endonuclease treated chromosomal DNA that hybridized with $^{32}$P-labeled pPC 15.0, pPC 8.0, or pPC 6.4. Then the eluted genomic DNA fragments were cloned into *Escherichia coli* and the appropriate genomic clones identified by screening several times with each of the above cDNA probes.

The relationship of each cDNA clone to its corresponding genomic clone is illustrated in FIGS. 1, 2, and 3. pPC 15.0 is encoded within a 6000 nucleotide HindIII genomic fragment present in clone pPG 6.0 (FIG. 1). The 5' end of the gene encoded by pPC 15.0 is oriented toward the 1300 bp HindIII-EcoRI fragment contained in pPG 6.0, while the 3' end of the gene is proximal to the PstI sites in pPG 6.0.

The cDNA clone pPC 8.3 is included within the genomic clone pPG 4.0 (FIG. 2). pPG 4.0 contains an EcorRI-PvuII insert of 4000 nucleotides of contiguous genomic DNA. The orientation of pPC 8.3 within pPG 4.0 places the 5' end of the gene for this cDNA clone close to the BamHI sites while the 3' end of this gene is located near the PvuII site. The orientation of pPC 8.0 (a related cDNA clone) within pPG 4.0 places the 5' end of this cDNA clone close to the KpnI site at the 3' end of pPG 4.0 and the 3' end of the cDNA clone is located near the PvuII site.

The cDNA clone pPC 6.7 is located entirely within a 4800 nucleotide EcoRI-BamHI genomic fragment (FIG. 3). Clone pPC 6.4 is in turn located completely within cDNA clone pPC 6.7. Since pPC 6.7 was a more complete copy than pPC 6.4, the latter was not investigated further. The 5' end of the gene is positioned closer to the BamHi end than to the EcoRI end of the genomic clone pPG 4.8 (FIG. 3).

In all of these above-described genomic clones, there are at least 1.2 kilobase pairs of flanking genomoic DNA sequence which are 5' to the structural genes copied in each of the cDNA clones.

Each of the genomic and cDNA clones described above have been deposited with the Northern Regional Research Center of the United States of America, Peoria, Ill., to insure access to the public upon issuance of this application as a patent. All clones have been deposited in *E. coli* hosts:

| Plasmid | Host | Accession No. |
| --- | --- | --- |
| pPG 6.0 | *E. coli* LE392-pPG 6.0 | NRRL B-15867 |

-continued

| Plasmid | Host | Accession No. |
| --- | --- | --- |
| pPG 4.0 | *E. coli* LE392-pPG 4.0 | NRRL B-15868 |
| pPG 4.8 | *E. coli* LE392-pPG 4.8 | NRRL B-15869 |
| pPC 15.0 | *E. coli* LE392-pPC 15.0 | NRRL B-15870 |
| pPC 8.3 | *E. coli* LE392-pPC 8.3 | NRRL B-15871 |
| pPC 6.7 | *E. coli* LE392-pPC 6.7 | NRRL B-15872 |
| pPC 8.0 | *E. coli* MM294-pPC 8.0 | NRRL B-15873 |

All of the above organisms have been irrevocably deposited and made available to the public as of Aug. 31, 1984.

UNIQUENESS OF pPG 6.0, pPG 4.0 AND pPG 4.8 TO METHANOL ASSIMILATING YEASTS

Each of the cDNA clones described above have been labeled and employed as probes of chromosomal DNA sequences from a number of methanol assimilating yeasts and a methanol non-assimilating yeast. Homologous genes for all three of the cDNAs were found to exist in essentially all methanol assimilating yeasts, but were clearly not present in methanol non-assimilating yeast (*S. cerevisiae*). It is thus believed that these genes are unique to methanol assimilating yeast. In addition, the Southern hybridization experiments detailed in Example XVII demonstrate that a high degree of homology exists between these unique methanol responsive genes from various methanol assimilating yeasts.

CHARACTERIZATION OF THE RNA TRANSCRIPTS OF THE pPG 6.0, pPG 4.0 AND pPG 4.8 GENES

The influence of methanol on the expression of each of these cloned genes can be observed by studying the effects on transcription of these genes. Isolated poly A+ RNA from *Pichia pastoris* cells grown with ethanol or methanol as sole carbon source was used to prepare Northern hybridization filters (See Example IV). Three identical pairs of filters from methanol and ethanol grown cells (See Example I) were probed separately with $^{32}$P-labeled pPC 15.0, pPC 8.0 and pPC 6.4. The clones pPC 15.0, pPC 8.0, and pPC 6.4 hybridized to RNA molecules (of approximately 2400, 2300, and 1300 nucleotides, respectively) from methanol grown cells. No hybridization of clones pPC 15.0 and pPC 8.0 with the hybridization probed was observed with RNA obtained from cells grown in the presence of ethanol. However, when RNA isolated from cells grown on ethanol was probed with pPC 6.4, the clone hybridized to a 1300-nucleotide RNA molecule identical to that seen with methanol-grown cells but at an estimated (qualitatively) 5-fold lower level.

SIZE DETERMINATION OF PROTEIN PRODUCTS ENCODED BY pPG 6.0, pPG 4.0 AND pPG 4.8

To determine what protein products were encoded by each of the above-identified cDNA clones, poly A+ RNA from *Pichia pastoris* cells grown on methanol was selectively hybridized to each of the cDNA clones. The hybrid-selected mRNA, i.e., mRNA which hybridized to each of the cDNA clones, was then translated in vitro and each of the protein products resolved by electrophoresis using SDS-denaturing conditions (See Example V). The results of these in vitro positive hybridization-translation experiments indicated that clones pPC 15.0, pPC 8.3, and pPC 6.7 select mRNAs which encode information for polypeptides of 76,000 (p76), 72,000 (p72) and 40,000 (p40) daltons, respectively. These same proteins are observed when total poly A+ RNA (i.e., not hybrid-selected) from methanol grown *Pichia pastoris* cells is translated in the same in vitro system.

IDENTIFICATION OF p72 AS ALCOHOL OXIDASE

A. Molecular Weight Comparison

A sample highly enriched for alcohol oxidase protein was prepared by dialysis of cleared cell lysates against H₂O (See Example VII). The crystalline precipitate resulting from this dialysis was shown by SDS electrophoresis to contain predominantly two polypeptides of 76,000 and 72,000 daltons, respectively. The precipitate was subjected to additional purification by chromotography through Sephacryl 200 (See Example VII), which demonstrated that alcohol oxidase activity corresponded to the activity of the purified 72,000 dalton polypeptide. The size of this polypeptide was identical to that of the protein product selected by cDNA clone pPC 8.3 (See Example X).

B. Immunoprecipitation

Additional support that clones pPC 8.3 and pPG 4.0 encode the alcohol oxidase structural gene was obtained by means of an immunological approach (Example XI). The protein preparation isolated from *Pichia pastoris* containing both the 76,000 and 72,000 dalton polypeptides was used to raise specific antisera for these polypeptides in rabbits. When the hybrid-selected poly A+ RNA from clone pPC 8.3 was translated in vitro, only the 72,000 dalton translation product was precipitated by the antisera made against the protein preparation from *Pichia pastoris* cells.

C. Predicted/Actual Amino Acid Sequence Comparison

To further verify that clone pPC 8.3 is in fact the cDNA clone encoding *Pichia pastoris* alcohol oxidase, the amino acid sequence for the amino terminal end of the protein was compared with the predicted amino acid sequence encoded by pPC 8.3. Thus, the NH₂-terminal amino acid sequence (Sequence A) of the isolated 72,000 dalton protein was determined (Example VIII) to be:

Ala—Ile—Pro—Glu—Glu—Phe—Asp—Ile—Leu—
—Val—Leu—Gly—Gly—Gly—Ser—Ser—Gly—Ser.

Sequence A

In parallel, the nucleotide sequence of the 5' end of the gene encoded in pPC 8.3 and pPG 4.0 was determined. The predicted amino acid sequence for amino acids 2-19 (See Sequence B) derived from the DNA sequences of both the genomic and cDNA clones agreed perfectly with the first 18 amino acids of the above determined amino acid sequence (Sequence A) for isolated *Pichia pastoris* alcohol oxidase:

| Predicted amino acid sequence: | | | | | Met | ala | ile | pro | glu | glu | phe |
|---|---|---|---|---|---|---|---|---|---|---|---|
| Nucleotide sequence (pPC 8.3 and pPG 4.0): | | | 5' | | —ATG | GCT | ATC | CCC | GAA | GAG | TTT |
| | | | 3' | | —TAC | CGA | TAG | GGG | CTT | CTC | AAA |
| asp | ile | leu | val | leu | gly | gly | gly | ser | ser | gly | ser |
| GAT | ATC | CTA | GTT | CTA | GGT | GGT | GGA | TCC | AGT | GGA | TCC-3' |
| CTA | TAG | GAT | CAA | GAT | CCA | CCA | CCT | AGG | TCA | CCT | AGG-5' |

Sequence B

In addition, the entire nucleotide sequence for the coding region of the alcohol oxidase gene was determined. The nucleotide sequence determined and the predicted amino acid sequence are set forth in Sequence B' and are believed to be:

| Predicted amino acid sequence: | | | | | Met | ala | ile | pro | glu | glu | phe |
|---|---|---|---|---|---|---|---|---|---|---|---|
| Nucleotide sequence (pPC 8.3 and pPG 4.0): | | | 5' | | —ATG | GCT | ATC | CCC | GAA | GAG | TTT |
| | | | 3' | | —TAC | CGA | TAG | GGG | CTT | CTC | AAA |
| asp | ile | leu | val | leu | gly | gly | gly | ser | ser | gly | ser |
| GAT | ATC | CTA | GTT | CTA | GGT | GGT | GGA | TTC | AGT | GGA | TCC |
| CTA | TAG | GAT | CAA | GAT | CCA | CCA | CCT | AGG | TCA | CCT | AGG |
| cys | ile | ser | gly | arg | leu | ala | asn | leu | asp | his | ser |
| TGT | ATT | TCC | GGA | AGA | TTG | GCA | AAC | TTG | GAC | CAC | TCC |
| ACA | TAA | AGG | CCT | TCT | AAC | CGT | TTG | AAC | CTG | GTG | AGG |
| leu | lys | val | gly | leu | ile | glu | ala | gly | glu | asn | gln |
| TTG | AAA | GTT | GGT | CTT | ATC | GAA | GCA | GGT | GAG | AAC | CAA |
| AAC | TTT | CAA | CCA | GAA | TAG | CTT | CGT | CCA | CTC | TTG | GTT |
| pro | gln | gln | pro | met | gly | leu | pro | ser | arg | tyr | leu |
| CCT | CAA | CAA | CCC | ATG | GGT | CTA | CCT | TCC | AGG | TAT | TTA |
| GGA | GTT | GTT | GGG | TAC | CCA | GAT | GGA | AGG | TCC | ATA | AAT |
| pro | lys | lys | gln | lys | leu | asp | ser | lys | thr | ala | ser |
| CCC | AAG | AAA | CAG | AAG | TTG | GAC | TCC | AAG | ACT | GCT | TCC |
| GGG | TTC | TTT | GTC | TTC | AAC | CTG | AGG | TTC | TGA | CGA | AGG |
| phe | tyr | thr | ser | asn | pro | ser | pro | his | leu | asn | gly |
| TTC | TAC | ACT | TCT | AAC | CCA | TCT | CCT | CAC | TTG | AAT | GGT |
| AAG | ATG | TGA | AGA | TTG | GGT | AGA | GGA | GTG | AAC | TTA | CCA |
| arg | arg | ala | ile | val | pro | cys | ala | asn | val | leu | gly |
| AGA | AGA | GCC | ATC | GTT | CCA | TGT -continued

| Predicted amino acid sequence: | | | | | Met | ala | ile | pro | glu | glu | phe |
|---|---|---|---|---|---|---|---|---|---|---|---|
| GGT | TCT | GCT | TCT | GAT | TCT | GAT | GAC | TTN | CAA | GCC | GAG |
| CCA | AGA | CGA | AGA | CTA | AGA | CTA | CTG | AAN | GTT | CGG | CTC |
| gly | ser | lys | thr | glu | asp | leu | leu | pro | leu | met | lys |
| GGC | TCG | AAA | ACA | GAG | GAC | TTG | CTT | CCA | TTG | ATG | AAA |
| CCG | AGC | TTT | TGT | CTC | CTG | AAC | GAA | GGT | AAC | TAC | TTT |
| lys | thr | glu | thr | tyr | gln | arg | ala | ? | gln | ? | tyr |
| AAG | ACT | GAG | ACC | TAC | CAA | AGA | GCT | TGN | CAA | CNA | TAC |
| TTC | TGA | CTC | TGG | ATG | GTT | TCT | CGA | ACN | GTT | GNT | ATG |
| pro | asp | ile | his | gly | phe | glu | gly | pro | ile | lys | val |
| CCT | GAC | ATT | CAC | GGT | TTC | GAA | GGT | CCA | ATC | AAG | GTT |
| GGA | CTG | TAA | GTG | CCA | AAG | CTT | CCA | GGT | TAG | TTC | CAA |
| ser | phe | gly | asn | tyr | thr | tyr | pro | val | cys | gln | asp |
| TCT | TTC | GGT | AAC | TAC | ACC | TAC | CCA | GTT | TGC | CAG | GAC |
| AGA | AAG | CCA | TTG | ATG | TGG | ATG | GGT | CAA | ACG | GTC | CTG |
| phe | leu | arg | ala | ser | glu | ser | gln | gly | ile | pro | tyr |
| TTC | TTG | AGG | GCT | TCT | GAG | TCC | CAA | GGT | ATT | CCA | TAC |
| AAG | AAC | TCC | CGA | AGA | CTC | AGG | GTT | CCA | TAA | CGT | ATG |
| val | asp | asp | leu | glu | asp | leu | val | leu | thr | his | gly |
| GTT | GAC | GAT | CTG | GAA | GAC | TTG | GTA | CTG | ACT | CAC | GGT |
| CAA | CTG | CTA | GAC | CTT | CTG | AAC | CAT | GAC | TGA | GTG | CCA |
| ala | glu | his | trp | leu | lys | trp | ile | asn | arg | asp | thr |
| GCT | GAA | CAC | TGG | TTG | AAG | TGG | ATC | AAC | AGA | GAC | ACT |
| CGA | CTT | GTG | ACC | AAC | TTC | ACC | TAG | TTG | TCT | CTG | TGA |
| gly | arg | arg | ser | asp | ser | ala | his | ala | phe | val | his |
| CGT | CGT | TCC | GAC | TCT | GCT | CAT | GCA | TTT | GTC | CAC | TCT |
| GCA | GCA | AGG | CTG | AGA | CGA | GTA | CGT | AAA | CAG | GTG | AGA |
| ser | thr | met | arg | asn | his | asp | asn | leu | tyr | leu | ile |
| TCT | ACT | ATG | AGA | AAC | CAC | GAC | AAC | TTG | TAC | TTG | ATC |
| AGA | TGA | TAC | TCT | TTG | GTG | CTG | TTG | AAC | ATG | AAC | TAG |
| cys | asn | thr | lys | val | asp | lys | ile | ile | val | glu | asp |
| TGT | AAC | ACG | AAG | GTC | GAC | AAA | ATT | ATT | GTC | GAA | GAC |
| ACA | TTG | TGC | TTC | CAG | CTG | TTT | TAA | TAA | CAG | CTT | CTG |
| gly | arg | ala | ala | ala | val | arg | thr | val | pro | ser | lys |
| GGA | AGA | GCT | GCT | GCT | GTT | AGA | ACC | GTT | CCA | AGC | AAG |
| CCT | TCT | CGA | CGA | CGA | CAA | TCT | TGG | CAA | GGT | TCG | TTC |
| pro | leu | asn | pro | lys | lys | pro | ser | his | lys | ile | tyr |
| CCT | TTG | AAC | CCA | AAG | AAG | CCA | AGT | CAC | AAG | ATC | TAC |
| GCA | AAC | TTG | GGT | TTC | TTC | GGT | TCA | GTG | TTC | TAG | ATG |
| arg | ala | arg | lys | gln | ile | phe | leu | ser | cys | gly | thr |
| CGT | GCT | AGA | AAG | CAA | ATC | TTT | TTG | TCT | TGT | GGT | ACC |
| GCA | CGA | TCT | TTC | GTT | TAG | AAA | AAC | AGA | ACA | CCA | TGG |
| ile | ser | ser | pro | leu | val | leu | gln | arg | ser | gly | phe |
| ATC | TCC | TCT | CCA | TTG | GTT | TTG | CAA | AGA | TCC | GGT | TTT |
| TAG | AGG | AGA | GGT | AAC | CAA | AAC | GTT | TCT | AGG | CCA | AAA |
| gly | asp | pro | ile | lys | leu | arg | ala | ala | gly | val | lys |
| GGT | GAC | CCA | ATC | AAG | TTG | AGA | GCC | GCT | GGT | GTT | AAG |
| CCA | CTG | GGT | TAG | TTC | AAC | TCT | CGG | CGA | CCA | CAA | TTC |
| pro | leu | val | asn | leu | pro | gly | val | gly | arg | asn | phe |
| CCT | TTG | GTC | AAC | TTG | CCA | GGT | GTC | GGA | AGA | AAC | TTC |
| GGA | AAC | CAG | TTG | AAC | GGT | CCA | CAG | CCT | TCT | TTG | AAG |
| gln | asp | his | tyr | cys | phe | phe | ser | pro | tyr | arg | ile |
| CAA | GAC | CAT | TAT | TGT | TTC | TTC | AGT | CCT | TAC | AGA | ATC |
| GTT | CTG | GTA | ATA | ACA | AAG | AAG | TCA | GGA | ATG | TCT | TAG |
| lys | pro | gln | tyr | glu | ser | phe | asp | asp | phe | val | arg |
| AAG | CCT | CAG | TAC | GAG | TCT | TTC | GAT | GAC | TTC | GTC | CGT |
| TTC | GCA | GTC | ATG | CTC | AGA | AAG | CTA | CTG | AAG | CAG | GCA |
| gly | asp | ala | glu | ile | gln | lys | arg | val | val | asp | gln |
| GGT | GAT | GCT | GAG | ATT | CAA | AAG | AGA | GTC | GTT | GAC | CAA |
| CCA | CTA | CGA | CTC | TAA | GTT | TTC | TCT | CAG | CAA | CTG | GTT |
| trp | tyr | ala | asn | gly | thr | gly | pro | leu | ala | thr | asn |
| TGG | TAC | GCC | AAT | GGT | ACT | GGT | CCT | CTT | GCC | ACT | AAC |
| ACC | ATG | CGG | TTA | CCA | TGA | CCA | GGA | GAA | CGG | TGA | TTG |
| gly | ile | glu | ala | gly | val | lys | ile | arg | pro | thr | pro |
| GGT | ATC | GAA | GCT | GGT | GTC | AAG | ATC | AGA | CCA | ACA | CCA |
| CCA | TAG | CTT | CGA | CCA | CAG | TTC | TAG | TCT | GGT | TGT | GGT |
| glu | glu | leu | ser | gln | met | asp | glu | ser | phe | gln | glu |
| GAA | GAA | CTC | TCT | CAA | ATG | GAC | GAA | TCC | TTC | CAG | GAG |
| CTT | CTT | GAG | AGA | GTT | TAC | CTG | CTT | AGG | AAG | GTC | CTC |
| gly | tyr | arg | glu | tyr | phe | glu | asp | lys | pro | asp | lys |
| GGT | TAC | AGA | GAA | TAC | TTC | GAA | GAC | AAG | CCA | GAC | AAG |
| CCA | ATG | TCT | CTT | ATG | AAG | CTT | CTG | TTC | GGT | CTG | TTC |
| pro | val | met | his | tyr | ser | ile | ile | ala | gly | phe | phe |
| CCA | GTT | ATG | CAC | TAC | TCC | ATC | ATT | GCT | GGT | TTC | TTC |
| GGT | CAA | TAC | GTG | ATG | AGG | TAG | TAA | CGA | CCA | AAG | AAG |
| gly | asp | his | thr | lys | ile | pro | pro | gly | lys | tyr | met |
| GGT | GAC | CAC | ACC | AAG | ATT | CCT | CCT | GGA | AAG | TAC | ATG |
| CCA | CT  | GTG | TGG | TTC | TAA | GGA | GGA | CCT | TTC | ATG | TAC |
| thr | met | phe | lys | phe | leu | glu | tyr | pro | phe | ser | arg |
| ACT | ATG | TTC | CAC | TTC | TTG | GAA | TAC | CCA | TTC | TCC | AGA |
| TGA | TAC | AAG | GTG | AAG | AAC | CTT | ATG | GGT | AAG | AGG | TCT |

-continued

| Predicted amino acid sequence: | | | | | Met | ala | ile | pro | glu | glu | phe |
|---|---|---|---|---|---|---|---|---|---|---|---|
| gly | ser | ile | his | ile | thr | ser | pro | asp | pro | tyr | ala |
| GGT | TCC | ATT | CAC | ATT | ACC | TCC | CCA | GAC | CCA | TAC | GCA |
| CCA | AGG | TAA | GTG | TAA | TGG | AGG | GGT | CTG | GGT | ATG | CGT |
| ala | pro | asp | phe | asp | arg | gly | phe | met | asn | asp | glu |
| GCT | CCA | GAC | TTC | GAC | CGA | GGT | TTC | ATG | AAC | GAT | GAA |
| CGA | GGT | CTG | AAG | CTG | GCT | CCA | AAG | TAC | TTG | CTA | CTT |
| arg | asp | met | ala | pro | met | val | trp | ala | tyr | lys | ser |
| AGA | GAC | ATG | GCT | CCT | ATG | GTT | TGG | GCT | TAC | AAG | TCT |
| TCT | CTG | TAC | CGA | GGA | TAC | CAA | ACC | CGA | ATG | TTC | TTC |
| ser | arg | glu | thr | ala | arg | arg | ser | asp | his | phe | ala |
| TCT | AGA | GAA | ACC | GCT | AGA | AGA | AGT | GAC | CAC | TTT | GCC |
| AGA | TCT | CTT | TGG | CGA | TCT | TCT | TCA | CTG | GTG | AAA | CGG |
| gly | glu | val | thr | ser | his | his | pro | leu | phe | pro | tyr |
| GGT | GAG | GTC | ACT | TCT | CAC | CAC | CCT | CTG | TTC | CCA | TAC |
| CCA | CTC | CAG | TGA | AGA | GTG | GTG | GGA | GAC | AAG | GGT | ATG |
| ser | ser | glu | ala | arg | ala | leu | glu | met | asp | leu | glu |
| TCA | TCC | GAG | GCC | AGA | GCC | TTG | GAA | ATG | GAT | TTG | GAG |
| AGT | AGG | CTC | CGG | TCT | CGG | AAC | CTT | TAC | CTA | AAC | CTC |
| thr | ser | asn | ala | tyr | gly | gly | pro | leu | asn | leu | ser |
| ACC | TCT | AAT | GCC | TAC | GGT | GGA | CCT | TTG | AAC | TTG | TCT |
| TGG | AGA | TTA | CGG | ATG | CCA | CCT | GGA | AAC | TTG | AAC | AGA |
| ala | gly | leu | ala | his | gly | ser | trp | thr | gln | pro | leu |
| GCT | GGT | CTT | GCT | CAC | GGT | TCT | TGG | ACT | CAA | CCT | TTG |
| CGA | CCA | GAA | CGA | GTG | CCA | AGA | ACC | TGA | GTT | GGA | AAC |
| lys | lys | pro | thr | ala | lys | asn | glu | gly | his | val | thr |
| AAG | AAG | CCA | ACT | GCA | AAG | AAC | GAA | GGC | CAC | GIT | ACT |
| TTC | TTC | GGT | TGA | CGT | TTC | TTG | CTT | CCG | GTG | CAA | TGA |
| ser | asn | gln | val | glu | leu | his | pro | asp | ile | glu | tyr |
| TCG | AAC | CAG | GTC | GAG | CTT | CAT | CCA | GAC | ATC | GAG | TAC |
| AGC | TTG | GTC | CAG | CTC | GAA | GTA | GGT | CTG | TAG | CTC | ATG |
| asp | glu | glu | asp | asp | lys | ala | ile | glu | asn | tyr | ile |
| GAT | GAG | GAG | GAT | GAC | AAG | GCC | ATT | GAG | ACC | TAC | ATT |
| CTA | CTC | CTC | CTA | CTG | TTC | CGG | TAA | CTC | TTG | ATG | TAA |
| arg | glu | his | thr | glu | thr | thr | tpr | his | cys | leu | gly |
| CGT | GAG | CAC | ACT | GAG | ACC | ACA | TGG | CAC | TGT | CTG | GGA |
| GCA | CTC | GTG | TGA | CTC | TGG | TGT | ACC | GTG | ACA | CCA | GGT |
| thr | cys | ser | ile | gly | pro | arg | glu | gly | ser | lys | ile |
| ACC | TGT | TCC | ATC | GGT | CCA | AGA | GAA | GGT | TCC | AAG | ATC |
| TGG | ACA | AGG | TAG | CCA | GGT | TCT | CTT | CCA | AGG | TTC | TAG |
| val | lys | trp | gly | gly | val | leu | asp | his | arg | ser | asn |
| GTC | AAA | TGG | GGT | GGT | GTT | TIG | GAC | CAC | AGA | TCC | AAC |
| CAG | TTT | ACC | CCA | CCA | CAA | AAC | CTG | GTG | TCT | AGG | TTG |
| val | tyr | gly | val | lys | gly | leu | lys | val | gly | asp | leu |
| GTT | TAC | GGA | GTC | AAG | GGC | TIG | AAG | GTT | GGT | GAC | TTG |
| CAA | ATG | CCT | CAG | TTC | CCG | AAC | TTC | CAA | CCA | CTG | AAC |
| ser | val | cys | pro | asp | asn | val | gly | cys | asn | thr | tyr |
| TCC | GTG | TGC | CCA | GAC | AAT | GTT | GGT | TGT | AAC | ACC | TAC |
| AGG | CAC | ACG | GGT | CTG | TTA | CAA | CCA | ACA | TTG | TGG | ATG |
| thr | thr | ala | leu | leu | ile | gly | glu | lys | thr | ala | thr |
| ACC | ACC | GCT | CTT | TTG | ATC | GGT | GAA | AAG | ACT | GCC | ACT |
| TGG | TGG | CGA | GAA | AAC | TAG | CCA | CTT | TTC | TGA | CGG | TGA |
| leu | val | gly | glu | asp | leu | gly | tyr | ser | gly | glu | ala |
| TTG | GTT | GGA | GAA | CAT | TTA | GGA | TAC | TCT | GGT | GAG | GCC |
| AAC | CAA | CCT | CTT | CTA | AAT | CCT | ATG | AGA | CCA | CTC | CGG |
| leu | asp | met | thr | val | pro | gln | phe | lys | leu | gly | thr |
| TTA | GAC | ATG | ACT | GTT | CCT | CAG | TTC | AAG | TTG | GGC | ACT |
| AAT | CTG | TAC | TGA | CAA | GGA | GTC | AAG | TTC | AAC | CCG | TGA |
| tyr | glu | lys | thr | gly | leu | ala | arg | phe | stop | | |
| TAC | GAG | AAG | ACC | GGT | CTT | GCT | AGA | TTC | TAA-3' | | |
| ATG | CTC | TTC | TGG | CCA | GAA | CGA | TCT | AAG | ATT-5' | | |

Sequence B'

A comparison of the above nucleotide sequence with the published (Ledeboer et al.) nucleotide sequence for the previously described alcohol oxidase from Hansenula polymorpha reveals numerous significant differences, including the predicted amino acid sequence, the actual size of the gene (and the resulting protein), codon usage bias, and the like.

Identification of p76 as Dihydroxyacetone Synthase

The nucleotide sequence for the first 51 nucleotides of the p76 gene was determined by standard techniques. From this sequence, the amino acid sequence for the amino terminal end of the p76 protein can be predicted:

| Amino acid sequence: | | | | met | ala | arg | ile | pro | lys |
|---|---|---|---|---|---|---|---|---|---|
| Nucleotide sequence: | | | 5' | —ATG | GCT | AGA | ATT | CCA | AAA |
| | | | 3' | —TAC | CGA | TCT | TAA | GGT | TTT |
| pro | val | ser | thr | gln | asp | asp | ile | his | gly | leu |

| Amino acid sequence: | | | | | met | ala | arg | ile | pro | lys |
|---|---|---|---|---|---|---|---|---|---|---|
| CCA | GTA | TCG | ACA | CAA | GAT | GAC | ATT | CAT | GAA | TTG-3' |
| GGT | CAT | AGC | TGT | GTT | CTA | CTG | TAA | GTA | CTT | AAC-5' |

This predicted amino acid sequence for p76 can be compared with the published amino acid sequence for the dihydroxyacetone synthase (DHAS) protein from *Hansenula polymorpha* (Manowicz et al.). Although several differences in the sequences are apparent, there are similarities between the two proteins which can be discerned:

| | |
|---|---|
| Pichia DHAS: | met-ala-arg-ile-pro-lys-pro- |
| Hansenula DHAS: | met-ser-met-arg-ile-pro-lys-ala-val-ser-thr-gln-asp-asp-ile-his-glu- -leu-ala-ser-val-asn-asp-glu-gln-his-gln-arg-ile- |

Based on the significant degree of homology and the similar protein size (about 76,000 daltons) of Pichia p76 and Hansenula DHAS, p76 has been tentatively identified as DHAS from Pichia.

As above with the alcohol oxidase gene, a comparison of the nucleotide sequence for the first 51 nucleotides of the Pichia DHAS protein with the previously published (Janowicz et al.) nucleotide sequence of Hansenula DHAS suggests numerous differences in codon usage bias, the predicted amino acid sequence, the total size of the gene, etc.

DNA Fragments Containing Regulatable Promoters from Pichia pastoris

Figure 5:
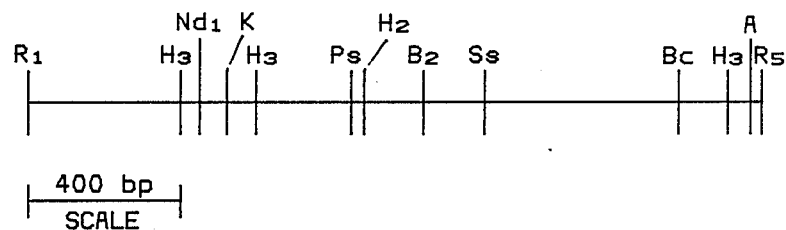
FIG. 5 is a restriction map of the regulatory region of the invention from clone pPG 4.0.
Figure 6:
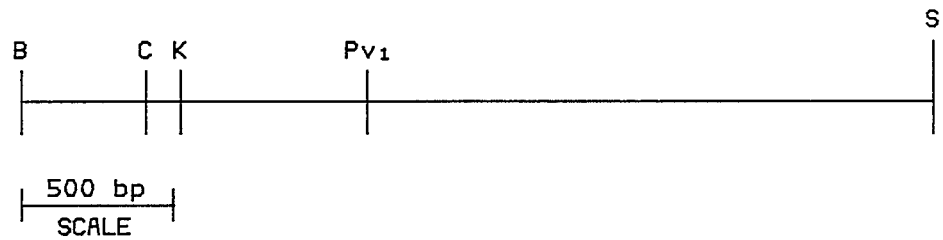
FIG. 6 is a restriction map of the regulatory region of the invention from clone pPG 4.8.

The 5' regulatory regions of the invention are detailed in restriction maps presented in FIGS. 4, 5 and 6. The 5' regulatory region which controls the expression of polypeptide p76 is located within the DNA fragment depicted in FIG. 4a. The approximately 2.9 kilobase pair HindIII-XhoI fragment has been clearly demonstrated to contain the regulatory function as detailed more fully below. Since cDNA clone pPC 15.0 is not a full copy cDNA, it is most likely that at least a portion of the DNA fragment depicted in FIG. 4a includes structural coding sequences for polypeptide p76. Thus, the regulatory function is believed to reside in the approximately 1300 base pair HindIII-EcoRI fragment shown in FIG. 4b. Novel β-galactosidase gene containing constructs, to be discussed in greater detail below, support this suggestion.

The 5' regulatory region which controls the expression of polypeptide p72 (alcohol oxidase is located within the approximately 2000 base pair EcoRI-BamHI DNA fragment illustrated in FIG. 5. Novel β-galactosidase gene containing constructs discussed below demonstrate the regulatable nature of this DNA fragment.

FIG. 6 provides a restriction map for the approximately 3 kilobase pair BanHI-SalI DNA fragment which includes the 5' regulatory region which controls the production of polypeptide p40. This fragment is clearly distinguishable from the 5' regulatory regions detailed in FIGS. 4 and 5 based, inter alia, on the different restriction sites located within the DNA fragment.

Figure 10:
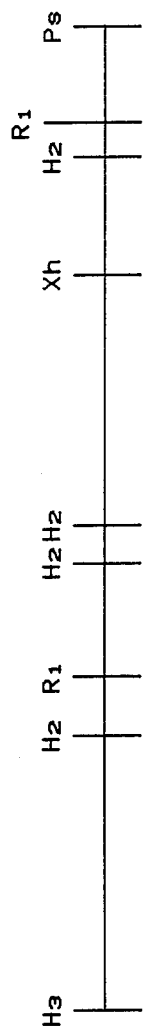
FIG. 10 is a restriction map of the protein p76 structural gene and the 5' regulatory region therefor.
Figure 11:
FIG. 11 is a restriction map of the protein p40 structural gene and the 5' regulatory region therefor.

FIGS. 10, 2a and 11 provide restriction enzyme data for the regulatory regions plus structural genes for polypeptides p76, p72(alcohol oxidase) and p40, respectively. Hence, FIG. 10 provides detail for the 3.8 kilobase pair HindIII-PstI fragment of *Pichia pastoris* genomic DNA which controls and codes for the production of polypeptide p76. FIG. 2a deals with the 4.0 kilobase pair EcoRI-PvuII fragment of *Pichia pastoris* genomic DNA which controls and codes for the production of polypeptide p72(alcohol oxidase). FIG. 11 presents the 3.7 kilobase pair BamHI-EcorRV fragment of *Pichia pastoris* genomic DNA which controls and codes for the production of polypeptide p40.

The genomic clones, pPG 6.0, pPG 4.0 and pPG 4.8 have also been characterized by restriction mapping. Thus, clone pPG 6.0 is detailed in FIG. 1a. As a point of reference the 5' end of the DNA fragment is deemed the origin. Clone pPG 6.0 is a HindIII fragment of *Pichia pastoris* chromosomal DNA which is about 6 kilobase pairs in length, and is cleaved as follows by various restriction enzymes:

| Restriction Enzyme | Cleavage Sites | Distance From Origin (bp) |
|---|---|---|
| HincII | 5 | 1070, 1740, 1890, 3320, 5520 |
| EcoRI | 2 | 1300, 3450 |
| XhoI | 1 | 2860, |
| PstI | 2 | 3820, 4200 |
| PvuII | 1 | 4120 |
| PvuI | 1 | 4950 |

Clone pPG 4.0 is illustrated in detail in FIG. 2a. The clone is an EcoRI-HindIII fragment of chromosomal DNA which is about 4 kilobase pairs in length. Referring to the 5' end of the clone as the origin, the following restriction data was obtained for pPG 4.0:

| Restriction Enzyme | Cleavage Sites | Distance From Origin (bp) |
|---|---|---|
| HindIII | 3 | 400, 600, 1840 |
| PstI | 1 | 850 |
| BamHI | 2 | 1960, 1970 |
| SalI | 1 | 2620 |
| BglII | 2 | 1040, 2700 |
| KpnI | 2 | 500, 2730 |
| XbaI | 1 | 3330 |
| StuI | 1 | 3880 |
| NdeI | 1 | 420 |
| HincII | 2 | 870; 2430 |
| SstI | 1 | 1200 |
| BclI | 2 | 1710, 4080 |
| AsuII | 2 | 1900, 2300 |
| EcoRV | 1 | 1930 |
| PvuII | 1 | 4120 |

Clone pPG 4.8 is illustrated in detail in FIG. 3a. The clone is a 4.8 kilobase pair BamHI-EcoRI fragment of *Pichia pastoris* chromosomal DNA with the following additional restriction sites:

| Restriction Enzyme | Cleavage Sites | Distance From Origin (bp) |
|---|---|---|
| ClaI | 1 | 410 |
| KpnI | 3 | 500, 3890, 4280 |
| PvuI | 1 | 1120 |
| SalI | 1 | 2900 |
| PvuII | 1 | 4135 |
| EcoRV | 2 | 3690, 3890 |
| BglII | 1 | 4500 |

| Restriction Enzyme | Cleavage Sites | Distance From Origin (bp) |
|---|---|---|
| XmaI | 1 | 4800 |

The genomic clones pPG 6.0, pPG 4.0 and pPG 4.8 were manipulated by insertion into unique restriction sites on the *E. coli* plasmid pBR322. Clone pPG 6.0, which is a HindIII fragment, was conveniently cloned into the HindIII site of pBR322. Clone pPG 4.0 was cloned into the EcoRI-PvuII sites of pBR322 and clone pPG 4.8 was cloned into the EcoRI-BamHI sites of pBR322. (See Example VI). *E. coli* strains transformed with these plasmids have been deposited with the Northern Regional Research Center, Peoria, Ill., to insure free access to the public upon issuance of a patent on this application. The deposited strains have been given the following accession numbers:

| Genomic Class | Laboratory Designation | Accession No. |
|---|---|---|
| pPG 6.0 | LE392-pPG 6.0 | NRRL B-15867 |
| pPG 4.0 | LE392-pPG 4.0 | NRRL B-15868 |
| pPG 4.8 | LE392-pPG 4.8 | NRRL B-15869 |

Figure 7:
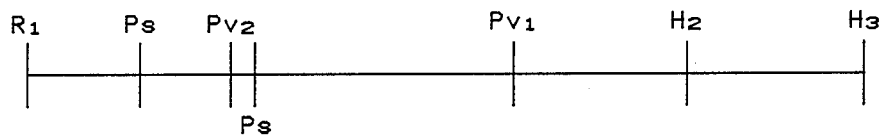
FIG. 7 is a restriction map of a sequence of DNA obtained from the 3' end of the p76 structural gene.
Figure 8:
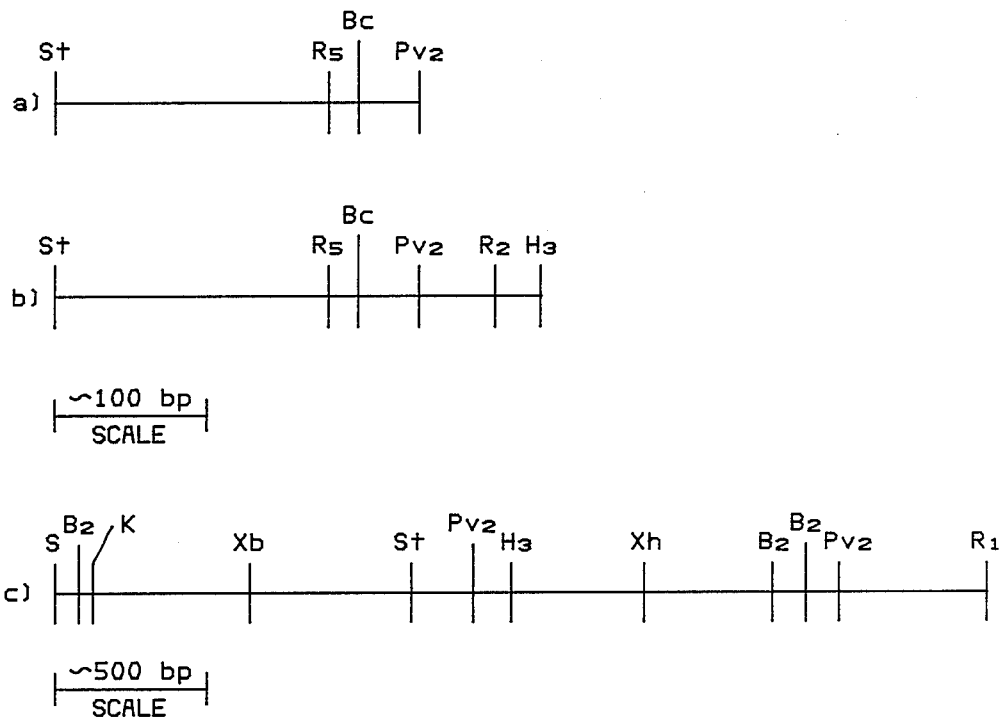
FIG. 8 provides restriction maps of sequences of DNA obtained from the 3' end of the p72 (alcohol oxidase) structural gene.
Figure 9:
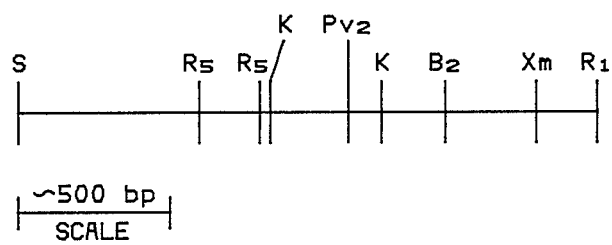
FIG. 9 is a restriction map of a sequence of DNA obtained from the 3' end of the p40 structural gene.

FIGS. 7, 8 and 9 provide restriction map data for the 3' regulatory regions of the polypeptides p76, p72 (alcohol oxidase) and p40, respectively. The 3' regulatory regions are useful in controlling the polyadenylation, termination of transcription and termination of translation of messenger RNA which is coded for by preceding nucleotide sequences. Thus the 3' regulatory region from the polypeptide p76 gene, a 2.7 kilobase pair EcoR1-HindIII fragment illustrated in FIG. 7, is useful in controlling the polyadenylation as well as termination of transcription and termination of translation of the mRNA which codes for polypeptide p76, or any other mRNA derived from a gene inserted upstream of the 3' regulatory region. The 0.2 kilobase pair StuI-PvuII fragment from the p72 gene detailed in FIG. 8a, the 0.3 kilobase pair StuI-HindIII fragment from the p72 gene detailed in FIG. 8b, the 3.2 kilobase pair SalI-EcoRI fragment from the p72 gene detailed in FIG. 8c, and the 1.9 kilobase pair PvuII-EcoRI fragment from the p40 gene detailed in FIG. 9 have similar utility, both with respect to the structural genes with which they are associated in the wild type *Pichia pastoris* and any foreign (i.e. heterologous) genes which may be inserted upstream of these 3' regulatory regions.

Since the alcohol oxidase gene in pPG4.0 terminates within a few hundred base pairs of the AO gene transcription termination site, the additional 3' sequence detailed in FIG. 8c was obtained as follows. The first step was to digest Pichia chromosomal DNA with EcoRI and SalI and hybridize the digested DNA with a 2.0 kbp $^{32}$P-labelled BamHI-HindIII fragment from the AO gene by the Southern blot method. Among the Pichia EcoRI-SalI digestion fragments which hybridized with the AO gene probe was a 3.2 kbp fragment which encodes the 3' portion of the AO gene and sequences flanking the 3' terminus of the gene.

The 3' AO gene fragment was then cloned by recovering EcoRI-SalI-cut Pichia DNA fragments of about 3.2 kbp by gel elution and inserting the fragments into EcoRI and SalI-digested pBR322. Finally a recombinant plasmid pPG3.2, which contains the 3' gene fragment was identified by colony hybridization using the labelled AO gene fragment as probe. An *E. coli* strain transformed with plasmid pPG3.2 has been deposited with the Northern Regional Research Center, Peoria, Ill., to insure free access to the public upon issuance of a patent on this application. The deposited strain has been assigned accession number NRRL B-15999. FIG. 8c shows a restriction endonuclease cleavage site map of the Pichia DNA fragment from pPG3.2. The fragment contains about 1.5 kbp encoding the 3' portion of the AO (from SalI to HindIII) and about 1.7 kbp of sequence 3' of the AO gene.

Characterization of cDNA Clones

Figure 12:
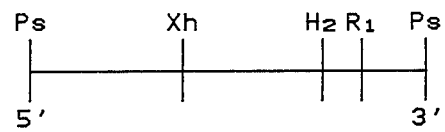
FIG. 12 is a restriction map of the protein p76 cDNA.
Figure 13:
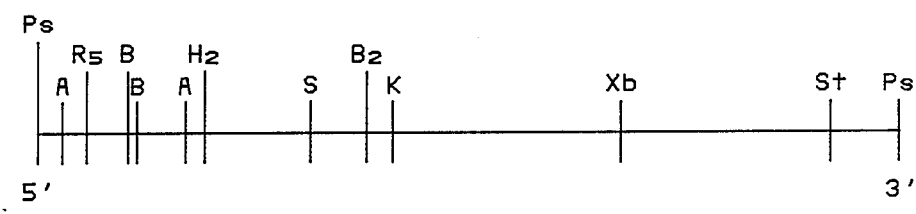
FIG. 13 is a restriction map of the protein p72 (alcohol oxidase) cDNA.
Figure 14:
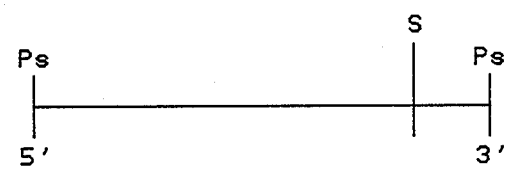
FIG. 14 is a restriction map of the protein p40 cDNA.

The cDNA clones for the regulatable genes from *Pichia pastoris* have also been characterized by restriction mapping. In FIG. 12, the p76 cDNA, a 1.1 kilobase pair fragment is detailed. Referring to the 5' end of the DNA sequence as the origin, restriction enzyme XhoI cleaves p76 cDNA about 500 base pairs from the origin, HincII cleaves about 950 base pairs from the origin and EcoRI cleaves p76 cDNA about 1050–1100 base pairs from the origin. The cDNA clone shown in FIG. 12, as well as the cDNA clones shown in FIGS. 13 and 14 are all shown with PstI termini. These are artificially created restriction sites produced by G-C tailing of the initially obtained complementary DNA to facilitate cloning of the DNA fragments into pBR322. Based on Northern hybridization studies and the size of the polypeptide product, it is estimated that the cDNA clone pPC 15.0 is an incomplete copy of p76 mRNA, representing only about half of the total messenger RNA sequence.

In FIG. 13, a composite restriction map for p72 (alcohol oxidase) cDNA, constructed by overlap of clones pPC 8.3 and pPC 8.0, is presented. As above, the 5' end of the DNA sequence is referred to as the origin. Thus, treating alcohol oxidase cDNA with a variety of restriction enzymes gives the following size fragments:

| Restriction Enzyme | Cleavage Sites | Distance From Origin (bp) |
|---|---|---|
| AsuII | 2 | 20, 420 |
| EcoRV | 1 | 50 |
| BamHI | 2 | 80, 90 |
| HincII | 1 | 550 |
| SalI | 1 | 820 |
| BglII | 1 | 820 |
| KpnI | 1 | 850 |
| XbaI | 1 | 1450 |
| RsaI | 1 | 1760 |
| StuI | 1 | 2000 |

Restriction enzyme mapping of the 3' end of the alcohol oxidase gene in clones pPC 8.0 and pPC 8.3 revealed that cDNA clone pPC 8.3 is missing approximately 250 nucleotides of the alcohol oxidase mRNA sequence (FIG. 2). The sequences present at the 3' end of the alcohol oxidase mRNA are present in cDNA clone pPC 8.0 which overlaps pPC 8.3 by approximately 500 nucleotides.

FIG. 14 presents a restriction map for the cDNA of polypeptide p40, a 1.2 kilobase pair fragment. Referring to the 5' end of the cDNA clone as the origin, clone pPC 6.7 is cleaved by SalI (and HincII) about 1000 bases from the origin.

Each of the cDNA fragments have been cloned into pBR322, which is then transformed into *E. coli*. The transformed strains have been deposited with the Northern Regional Research Center in Peoria, Ill. to insure free access to the public upon issuance of this application as a patent. The deposited strains have been assigned the following accession numbers:

| cDNA clone | Laboratory Description | Accession No. |
|---|---|---|
| pPC 15.0 | LE392-pPC 15.0 | NRRL B-15870 |
| pPC 8.3 | LE392-pPC 8.3 | NRRL B-15871 |
| pPC 8.0 | MM294-pPC 8.0 | NRRL B-15873 |
| pPC 6.7 | LE392-pPC 6.7 | NRRL B-15872 |

Each of the above-described cDNA clones are useful as probes for the identification and isolation of chromosomal DNA encoding the production of polypeptides unique to the growth of yeast on methanol as a carbon and energy source. Hence as already described, these clones were used to identify *P. pastoris* chromosomal DNA fragments containing the regulatory regions and structural coding information for the unique polypeptides which are observed when *P. pastoris* is grown on methanol. In a similar fashion, these cDNA clones have utility as probes for the identification and isolation of analogous genes from other methanol assimilating yeasts such as, for example *Torulopsis molischiana, Hansenula capsulatum, H. nonfermantens* and the like (See Example XVII).

Detailed Analysis of the Alcohol Oxidase Gene

The 5' regulatory region of clone pPG 4.0 was further characterized by determining the nucleotide sequence of the clone upstream (5') of the point where the structural information for p72 (alcohol oxidase) is encoded. The first 250 nucleotides prior to the mRNA translation start site (ATG codon) are believed to be:

| | | | |
|---|---|---|---|
| 5'-ATGCTTCCAA | GATTCTGGTG | GGAATACTGC | TGATAGCCTA |
| ACGTTCATGA | TCAAAATTTA | ACTGTTCTAA | CCCCTACTTG |
| GACAGGCAAT | ATATAAACAG | AAGGAAGCTG | CCCTGTCTTA |
| AACCTTTTTT | TTTATCATCA | TTATTAGCTT | ACTTTCATAA |
| TTGCGACTGG | TTCCAATTGA | CAAGCTTTTG | ATTTTAACGA |
| CTTTTAACGA | CAACTTGAGA | AGATCAAAAA | ACAACTAATT |
| ATTCGAAACG-3'. | | | |

Sequence C

The promoter function of clone pPG 4.0 is believed to be contained within this sequence of nucleotide bases.

In order to more fully describe this novel DNA fragment, an additional 301 nucleotides further upstream of the sequence detailed in Sequence C above have been determined. Thus, the first 551 nucleotides prior to the mRNA translation start site are believed to be:

| | | | |
|---|---|---|---|
| 5'-AATGGCCCAAA | ACTGACAGTTT | AAACGCTGTC | TTGGAACCTA |
| ATATGACAAA | AGCGTGATCT | CATCCAAGAT | GAACTAAGTT |
| TGGTTCGTTG | AAATCCTAAC | GGCCAGTTGG | TCAAAAAGAA |
| ACTTCCAAAA | GTCGCCATAC | CGTTTGTCTT | GTTTGGTATT |
| GATTGACGAA | TGCTCAAAAA | TAATCTCATT | AATGCTTAGC |
| GCAGTCTCTC | TATCGCTTCT | GAACCCGGTG | GCACCTGTGC |
| CGAAACGCAA | ATGGGGAAAC | AACCCGCTTT | TTGGATGATT |
| ATGCATTGTC | TCCACATTGT | ATGCTTCCAA | GATTCTGGTG |
| GGAATACTGC | TGATAGCCTA | ACGTTCATGA | TCAAAATTTA |
| ACTGTTCTAA | CCCCTACTTG | GACAGGCAAT | ATATAAACAG |
| AAGGAAGCTG | CCCTGTCTTA | AACCTTTTTT | TTTATCATCA |
| TTATTAGCTT | ACTTTCATAA | TTGCGACTGG | TTCCAATTGA |
| CAAGCTTTTG | ATTTTAACGA | CTTTTAACGA | CAACTTGAGA |
| AGATCAAAAA | ACAACTAATT | ATTCGAAACG-3'. | |

Sequence D

The additional nucleotides contained in Sequence D (compared to Sequence C) are believed to impart, by an unknown mechanism, additional regulatory functions to the promoter region contained within Sequence C. It should be recognized that Sequence D represents only partial DNA sequencing for the 1.1 kbp DNA fragment shown in Examples XIV and XV to be capable of controlling gene expression in yeast. It may be that additional control functions are encoded in the portion of the 1.1 kbp DNA fragment not detailed in Sequence D.

In order to further describe this novel 1.1 kbp DNA fragment, additional nucleotide sequencing was carried out to fully delineate the nucleotide sequence of the entire 1.1 kbp DNA fragment shown in Examples XIV and XV to be capable of controlling gene expression in yeast. The nucleotide sequence is set forth as Sequence D':

| | | | |
|---|---|---|---|
| | | 5'-AGATCTAA | CATCCAAAGA |
| CGAAAGGTTG | AATGAAACCT | TTTTGCCATC | CGACATCCAC |
| AGGTCCATTC | TCACACATAA | GTGCCAAACG | CAACAGGAGG |
| GGATACACTA | GCAGCAGACG | TTGCAAACGC | AGGACTCATC |
| CTCTTCTCTA | ACACCATTTT | GCATGAAAAC | AGCCAGTTAT |
| GGGCTTGATG | GAGCTCGCTC | ATTCCAATTC | CTTCTATTAG |
| GCTACTAACA | CCATGACTTT | ATTAGCCTGT | CTATCCTGGC |
| CCCCCTGGCG | AGGTCATGTT | TGTTTATTTC | CGAATGCAAC |
| AAGCTCCGCA | TTACACCCGA | ACATCACTCC | AGATGAGGGC |
| TTTCTGAGTG | TGGGGTCAAA | TAGTTTCATG | TTCCCAAATG |
| GCCCAAAACT | GACAGTTTAA | ACGCTGTCTT | GGAACCTAAT |
| ATGACAAAAG | CGTGATCTCA | TCCAAGATGA | ACTAAGTTTG |
| GTTCGTTGAA | ATCCTAACGG | CCAGTTGGTC | AAAAAGAAAC |
| TTCCAAAAGT | CGCCATACCG | TTTGTCTTGT | TTGGTATTGA |

-continued

| | | | |
|---|---|---|---|
| TTGACGAATG | CTCAAAAATA | ATCTCATTAA | TGCTTAGCGC |
| AGTCTCTCTA | TCGCTTCTGA | ACCCGGTGGC | ACCTGTGCCG |
| AAACGCAAAT | GGGGAAACAA | CCCGCTTTTT | GGATGATTAT |
| GCATTGTCCT | CCACATTGTA | TGCTTCCAAG | ATTCTGGTGG |
| GAATACTGCT | GATAGCCTAA | CGTTCATGAT | CAAAATTTAA |
| CTGTTCTAAC | CCCTACTTGG | ACAGGCAATA | TATAAACAGA |
| AGGAAGCTGC | CCTGTCTTAA | ACCTTTTTTT | TTATCATCAT |
| TATTAGCTTA | CTTTCATAAT | TGCGACTGGT | TCCAATTGAC |
| AAGCTTTTGA | TTTTAACGAC | TTTTAACGAC | AACTTGAGAA |
| GATCAAAAAA | CAACTAATTA | TTCGAAACG-3'. | |

Sequence D'

It is recognized by those of skill in the art that additional control functions, relative to Sequence C and D, may be encoded in that portion of Sequence D' which is further upstream (i.e., in the 5' direction) of the nucleotide sequence detailed in Sequences C and D.

To determine where RNA transcription for the alcohol oxidase gene is initiated, the DNA sequences around the 5' end of this gene from the genomic clone pPG 4.0 and the cDNA clone pPC 8.3 were compared. cDNA clone pPC 8.3 contains about 100 nucleotides of an untranslated region 5' to the alcohol oxidase gene. Based upon this sequence, an oligonucleotide of 15 bases (5'-CTTCTCAAGTTGTCG-3'): complementary with respect to nucleotides −29 to −43, where the A of the translation start site (ATG codon) is designated as +1 and the G in the 5' direction is designated as −1, was synthesized (See Example IX) and used as a primer to extend along the alcohol oxidase mRNA to reach the 5' end. The sequence of cDNA obtained from this primer-extension experiment revealed three different transcriptional initiation points for Pichia pastoris alcohol oxidase mRNA. The major transcript begins 114 nucleotides from the translational initiation codon. Two minor alternative transcripts begin 117 and 111 nucleotides upstream (5') from the alcohol oxidase AUG codon.

The 55 nucleotides preceding the start of alcohol oxidase mRNA contain a putative Goldberg-Hogness box (TATAA box). The sequence TATAA occurs at position −40 from the 5' end of the predominant transcript for alcohol oxidase mRNA and therefore 165 nucleotides upstream from the initiation codon for this protein.

The 3' regulatory region of the alcohol oxidase gene was further characterized by determining the nucleotide sequence for about 120 nucleotides downstream of the point where the structural information for p72 (alcohol oxidase) is encoded. The sequence is set forth below as Sequence D":

| | | | |
|---|---|---|---|
| 5'-TCAAGAGGAT | GTCAGAATGC | CATTTGCCTG | AGAGATGCAG |
| GCTTCATTTT | TGATACTTTT | TTATTTGTAA | CCTATATAGT |
| ATAGGATTTT | TTTTGTCAAA | AAAAAAAAAA | AAAAAAAAAA-3' |

Sequence D"

Detailed Analysis of the p76 Gene

The 5' regulatory region of the clone pPG 6.0 was also further characterized by determining the nucleotide sequence of the clone upstream (5') of the point where the structural information for p76 is encoded. The first 622 nucleotides prior to the mRNA translation start site (ATG codon) are believed to be:

| | | | 5'TT |
|---|---|---|---|
| CACCCATACA | ACTATAAACC | TTAGCAATTG | AAATAACCCC |
| AATTCATTGT | TCCGAGTTTA | ATATACTTGC | CCCTATAAGA |
| AACCAAGGGA | TTTCAGCTTC | CTTACCCCAT | GAACAGAATC |
| TTCCATTTAC | CCCCCACTGG | AGAGATCCGC | CCAAACGAAC |
| AGATAATAGA | AAAAAACAAT | TCGGACAAAT | AGAACACTTT |
| CTCAGCCAAT | TAAAGTCATT | CCATGCACTC | CCTTTAGCTG |
| CCGTTCCATC | CCTTTGTTGA | GCAACACCAT | CGTTAGCCAG |
| TACGAAAGAG | GAAACTTAAC | CGATACCTTG | GAGAAATCTA |
| AGGCGCGAAT | GAGTTTAGCC | TAGATATCCT | TAGTGAAGGG |
| TGTCCGATAC | TTCTCCACAT | TCAGTCATAG | ATGGGCAGCT |
| TGTATCATGA | AGAGACGGAA | ACGGGCATAA | GGGTAACCGC |
| CAAATTATAT | AAAGACAACA | TGCCCCAGTT | TAAAGTTTTT |
| CTTTCCTATT | CTTGTATCCT | GAGTGACCGT | TGTGTTTAAT |
| ATAAAAGTT | CGTTTTAACT | TAAGACCAAA | ACCAGTTACA |
| ACAAATTATA | ACCCCTCTAA | ACACTAAAGT | TCACTCTTAT |
| CAAACTATCA | AACATCAAAA-3' | | |

Sequence D'''

The promoter function of clone pPG 6.0 is believed to be contained within this sequence of nucleotide bases, although those of skill in the art recognize that additional regulatory properties may be imparted by sequences further upstream than the sequences presented as Sequence D'''.

The 3' regulatory region of clone pPG 6.0 was further characterized by determining the nucleotide sequence for about 180 nucleotides downstream (3') of the point where the p76 structural information is encoded. The sequence is set forth below as Sequence D'''':

| | | | |
|---|---|---|---|
| 5'-GTCAGCAGTG | TTTCCTGCCA | AAGCCATCAA | GAGGACGTAC |

-continued

| | | | |
|---|---|---|---|
| ATGCTCTCAT | TTTTTGGTTT | TCTATGTCCG | ACGGGGTTCG |
| TAAACTGGCT | TCCTCCTTTT | CCTTTCCTGT | TGCATTTTAT |
| TTGGTCAAAC | AAAACTAGGG | TCTTTTCCTA | AAACCTTATG |
| TCAATGGACC | TACCACATAG-3' | | |

Sequence D''''

Expression in Transformed Yeast

The above-described plasmids of the present invention have utility in yeast strains which can be transformed. Regulation of gene expression in yeast by the novel DNA fragments of the present invention can be accomplished by subjecting the transformed organisms to carbon source starvation. Carbon source starvation after growth on a variety of both catabolite repressing and non-catabolite repressing carbon sources induces expression of the gene product maintained under the control of the regulatory regions of the invention. Another means to achieve expression of the desired gene product in appropriate species of transformed yeast is to grow transformed yeasts on methanol. Yet another means to induce expression of the desired gene product is to grow transformed yeast on media containing non-catabolite repressing carbon sources.

The regulatory regions of this invention are useful for expression in all yeast strains, since the regulatory regions have been shown to be induced under a variety of conditions. Thus, yeasts capable of growth on methanol or on non-catabolite repressing carbon sources can be caused to produce foreign, i.e., heterologous, polypeptides directly; while yeasts capable of growth on catabolite repressing carbon sources can be caused to produce foreign polypeptides by subjecting yeast cells so grown to conditions of carbon source starvation.

Transformed yeast strains which are preferred in the process of the present invention include members of the genera:
Candida,
Kloeckera,
Saccharomyces,
Schizosaccharomyces,
Rhodotorula,
Hansenula,
Torulopsis,
Pichia, and
Kluyveromyces.

Yeasts from these genera are preferred because their safety of handling, growth conditions and the like have been established and are well known to those of skill in the art.

Especially preferred yeast strains for use in one embodiment of the process of the present invention are those yeast strains which are capable of growth on methanol as carbon and energy source. Yeasts known to be capable of growth on methanol include members of the genera:
Candida,
Kloeckera,
Saccharomyces,
Rhodotorula,
Hansenula,
Torulopsis, and
Pichia.

Since the regulatory regions of the present invention are also induced by growth on non-catabolite repressing carbon sources as well as conditions of carbon source starvation, yeast strains which are capable of growth on such non-methanolic substrates as:
glucose,
acetate,
glycerol,
ethanol,
lactose,
galactose,
fructose,
sucrose,
and the like and mixtures of any two or more thereof are also useful in the practice of the invention. By growing the host organism on a suitable non-catabolite repressable non-methanolic carbon source such as, for example, glycerol and galactose, or by growing the host organism on a suitable catabolite repressable carbon source such as, for example, ethanol, glucose and fructose, then subjecting the host organism to carbon source starvation conditions, expression of a gene product under the control of the regulatory regions of the invention can be achieved.

In addition, since the regulatory regions of the invention are responsive to a variety of growth conditions, both in terms of induction and repression of expression, the regulated expression of a gene product under the control of the regulatory regions of the invention can be achieved. Thus, for example, cells can be grown on a carbon source which induces only low levels of foreign gene expression, then switched to methanol which will strongly induce gene expression. Alternatively, regulated gene expression can be achieved by employing mixtures of inducing/repressing feeds such as, for example, methanol-glucose mixtures. As yet another alternative, high expression levels produced by growth on methanol can be reduced as desired by addition to the growth media of a repressing carbon source such as glucose or ethanol. Of course, those of skill in the art recognize that other variations of feed mixtures and order of feed introduction are possible, and afford a great deal of control over the level of gene expression obtained from the invention regulatory regions.

An especially preferred host yeast strain is the mutant Pichia pastoris GS115, which is a mutant defective in the ability to produce histidine, and has thus been designated as having the mutant genotype his4. GS115 is derived from Pichia pastoris NRRL Y-11430 and has been deposited with the Northern Regional Research Center of the United States Department of Agriculture in Peoria, Ill., in order to ensure free access of the host to the public upon issuance of this application as a patent. Pichia pastoris GS115 has been assigned the accession number NRRL Y-15851, as of Aug. 31, 1984. This particular host is useful because it is an auxotrophic mutant deficient in the histidine pathway. Transformation of this host with a vector containing, among other DNA sequences, the HIS4 gene function, allows ready selection for transformed host.

Since the regulatory regions of the present invention have also been demonstrated to be useful for the regulated expression of heterologous gene products in yeast strains of the genus Saccharomyces, for which a large number of auxotrophic mutants are known. Additional preferred host yeast strains include ATCC 24683 (a trp1, ade1, his2, leu1, gal1, ura1, mutant), ATCC 24684 (a trp1, ade1, his7, gal1, ura1 mutant), ATCC 32810 (a trp5, arg4, his5, lys1, ade2, gal2 mutant), ATCC 34182 (an ade3, his, lys, ura mutant), ATCC 34352 (an ura2 mutant), ATCC 34353 (an ura2 mutant), ATCC 38523 (an arg1, thr1 mutant), ATCC 38626 (a leu2, his4 mutant), ATCC 38660 (a his4, leu2, thr4 mutant), ATCC 42243 (an ura3 mutant), ATCC 42336 (an ade1, his4, thr4 mutant), ATCC 42403 (an arg4, lys7 mutant), ATCC 42404 (an ade1, his4, leu2 mutant), ATCC 42564 (an ura1, his6 mutant), ATCC 42596 (a his4, leu2, lys1 mutant), ATCC 42957 (a his4, leu2, thr4, trp5 mutant), ATCC 42950 (an ade mutant), ATCC 42951 (an ade, leu mutant), ATCC 44069 (an ura1 mutant), ATCC 44070 (a leu2, his4 mutant), ATCC 44222 (a his4 mutant), ATCC 44376 (a his4, ade2 mutant), ATCC 44377 (a his4, leu1 mutant), and the like are readily accessible to those of skill in the art.

It is recognized by those of skill in the art that useful host strains are not limited to auxotrophic mutants. Thus, transformation of prototrophic strains with positive selection markers, such as, for example, antibiotic resistance genes, also provides a useful means for the detection and isolation of transformed strains.

*Escherichia coli* is also a suitable host for the plasmids of the invention. Those of skill in the art recognize that many strains of *E. coli* are suitable hosts. Several strains employed in the present work are summarized below:

| Strain designation | Accession Number |
|---|---|
| MC1061 | None known |
| LE392 | ATCC #33572 |
| MM294 | ATCC #33625 |

*Pichia pastoris* Transformation Procedure

The transformation of *Pichia pastoris* has not been previously described. The experimental procedures for transformation of *Pichia pastoris* are presented in greater detail below (Example XII). In order to develop a transformation system for *P. pastoris*, the auxotrophic mutant GS115 (NRRL Y-15851) was isolated and determined to be defective in the histidine pathway in that the strain has no detectable histidinol dehydrogenase activity.

GS115 (NRRL Y-15851) can be transformed by enzymatic digestion of the cell walls to give spheroplasts; the spheroplasts are then mixed with the transforming DNA and incubated in the presence of calcium ions and polyethylene glycol, then regenerated in selective growth medium deficient in histidine. The transforming DNA includes the HIS4 gene in which the host strain is deficient, thus only transformed cells survive on the selective growth medium employed.

Isolation of *Pichia pastoris* HIS4 Gene

Figure 25:
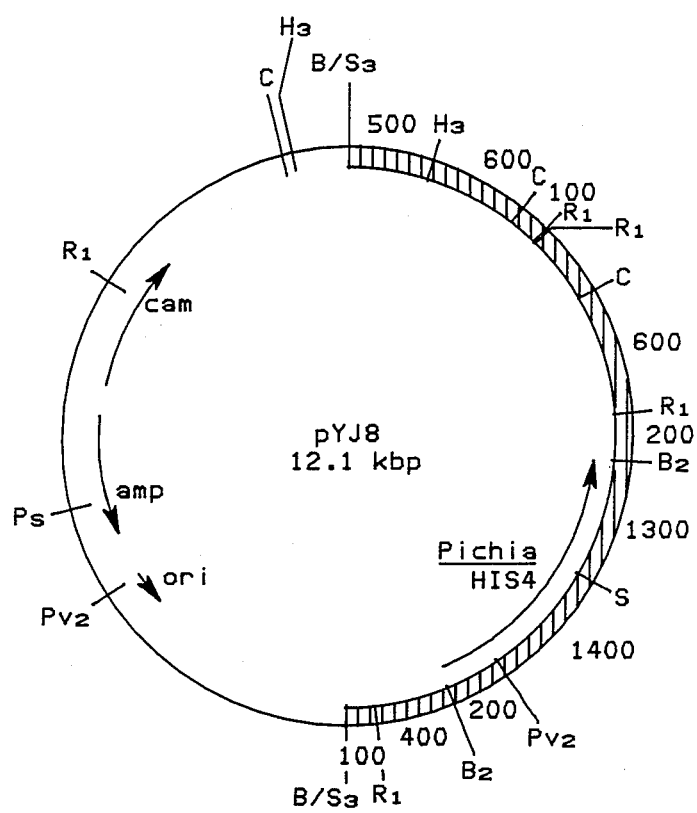
FIG. 25 is a restriction map of plasmid pYJ8.
Figure 33:
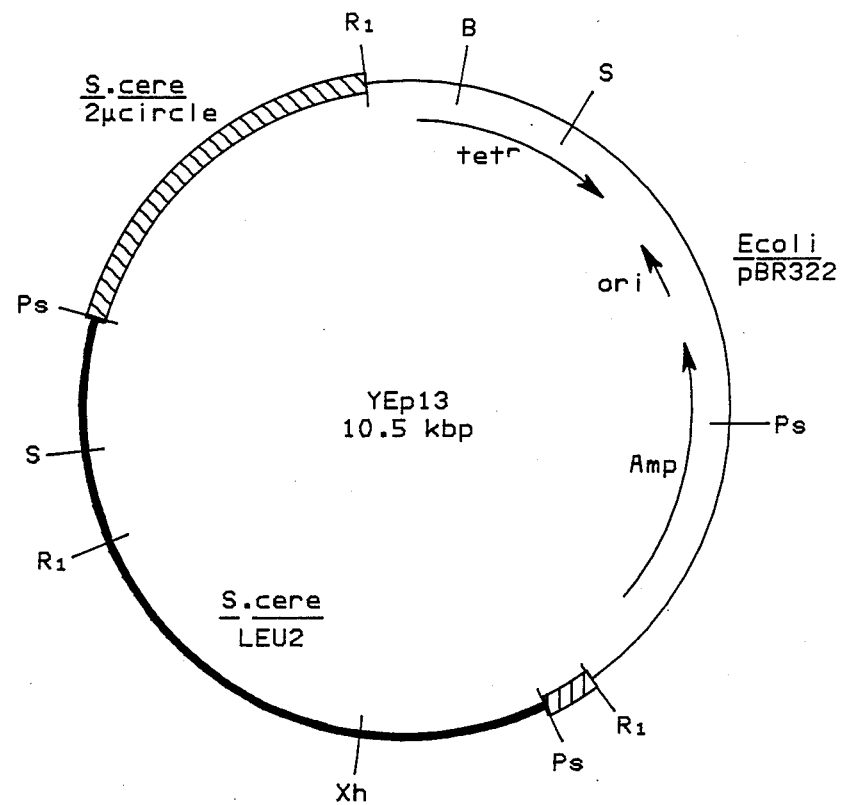
FIG. 33 provides a restriction map of plasmid YEp13.

The HIS4 gene was isolated from the strain *P. pastoris* NRRL Y-11430 by partial digestion of total chromosomal DNA with Sau3A followed by centrifugation through sucrose gradients. (See Example XIII). Fragments of 5 to 20 kbp were cloned into the BamHI cleavage site of the *S. cerevisiae-E. coli* shuttle vector YEp13 (ATCC 37115; FIG. 33) and transformed into *E. coli*. Approximately 50,000 colonies were combined and total plasmid DNA extracted. Spheroplasts of *S. cerevisiae* strain 5799-4D (NRRL Y-15859), a his4ABC mutant, were mixed with about 1 μg of the YEp13 Pichia DNA library by the procedure of Hinnen et al (1978) and allowed to regenerate in a medium deficient in histidine. The transformation resulted in about $1 \times 10^3$ prototrophic yeast colonies from a population of $5 \times 10^7$ total regenerable spheroplasts. A parallel control sample incubated without DNA produced no colonies. Total yeast DNA was extracted from 20 of the His+ colonies and transformed back into *E. coli*. Seventeen of the yeast DNA preparations produced ampicillin resistant colonies. These cloned fragments were further characterized by restriction enzyme sizing and mapping as well as by their ability to cross hybridize with a labelled *S. cerevisiae* HIS4 fragment at low stringency (post hybridization washes in 2×SSC at 55°) by the method described in Example XII, §G. The HIS4-containing plasmids each contained one or more fragments which hybridized to the *S. cerevisiae* HIS4 gene. One such HIS4-containing plasmid was recloned to give a HIS4-containing plasmid designated pYJ8 and is shown in FIG. 25. Plasmid pYJ8 contains pBR325 sequences, including chloramphenicol and ampicillin resistance genes, as well as the Pichia HIS4 gene.

The ARG4 gene was isolated from *P. pastoris* NRRL Y-11430 employing an analogous protocol and the Arg− *S. cerevisiae* strain S2072A (a arg4 leu2 trp1 gal2; obtained from the Yeast Genetic Stock Center, Berkely, Calif.).

Those of skill in the art recognize that other marker genes from Pichia can similarly be isolated employing appropriately deficient *S. cervisiae* strains.

Isolation of *Pichia pastoria* Autonomous Replication Sequences

Another useful component of the vectors of the present invention are Pichia-derived autonomous replication sequences (PARS), which enhance both the transformation frequency of GS115 (NRRL Y-15851) and the maintenance of plasmid as a stable extrachromosomal element.

Figure 26:
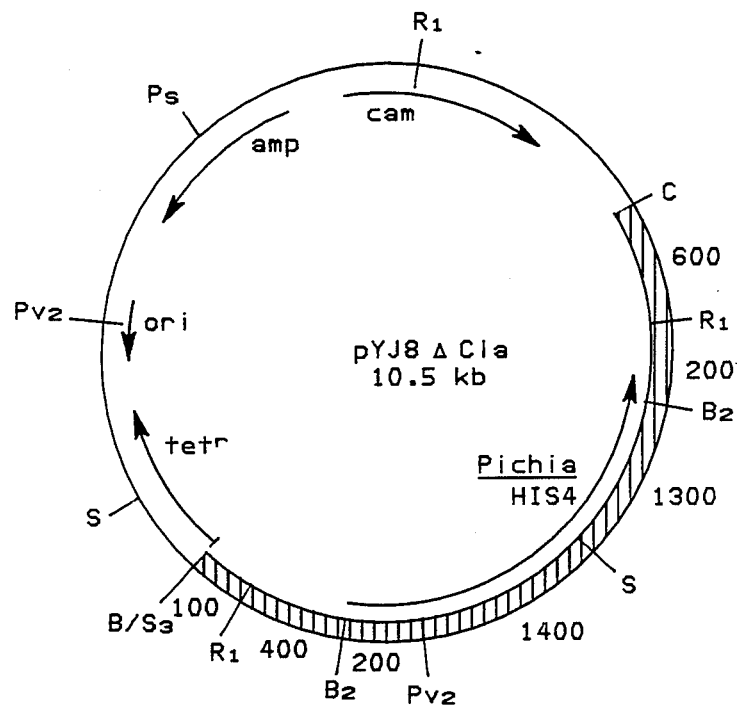
FIG. 26 is a restriction map of plasmid pYJ8∆Cla.

To search for Pichia ARSs, DNA from *Pichia pastoris* GS115 (NRRL Y-15851) was partially digested with TaqI and 5 to 10 kbp fragments were isolated and cloned into the unique ClaI site of pYJ8ΔCla. (See FIG. 26). Plasmid DNA was recovered from about 10,000 His+ Pichia colonies and used to transform *E. coli*. Plasmids from about 10,000 ampicillin resistant colonies were isolated and then transformed back into GS115. Forty of the His+ yeast colonies from this sublibrary transformation were separately streaked onto selective medium and grown in separate cultures in selective medium. Total yeast DNA was extracted from each of these 40 cultures and transformed into *E. coli*. Two plasmids, pYA63 (PARS1) and pYA90 (PARS2) whose yeast DNA preparations produced the most ampicillin resistant *E. coli* colonies, were selected for further analysis. Both of these plasmids transformed *Pichia pastoris* GS115 (NNRL Y-15851) at a very high frequency and each contained an insert of foreign DNA.

As a measure the ability of the ARSs to maintain plasmids as autonomous elements in Pichia, cultures of yeast cells which had been transformed with each plasmid were grown in selective medium and periodically sampled. The state of the plasmid sequences in the cells was determined by Southern hybridization of unrestricted yeast DNAs to radioactively labeled pBR325. Plasmids pYA63 and pYA90 were maintained in Pichia for at least 10 generations in the selective medium (but had integrated by 50 generations).

Figure 27:
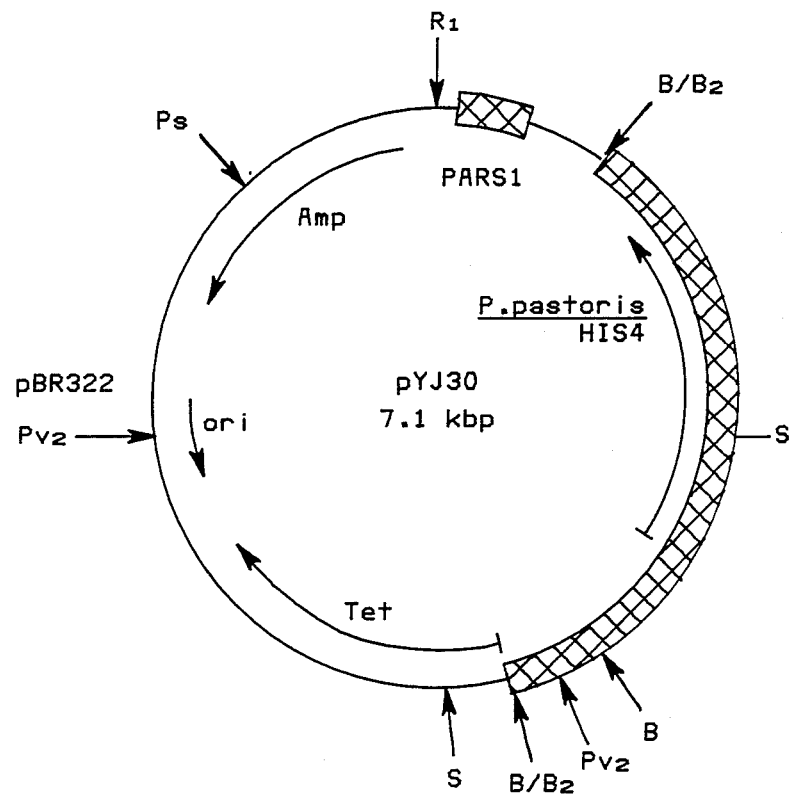
FIG. 27 is a restriction map of plasmid pYJ30.
Figure 34:
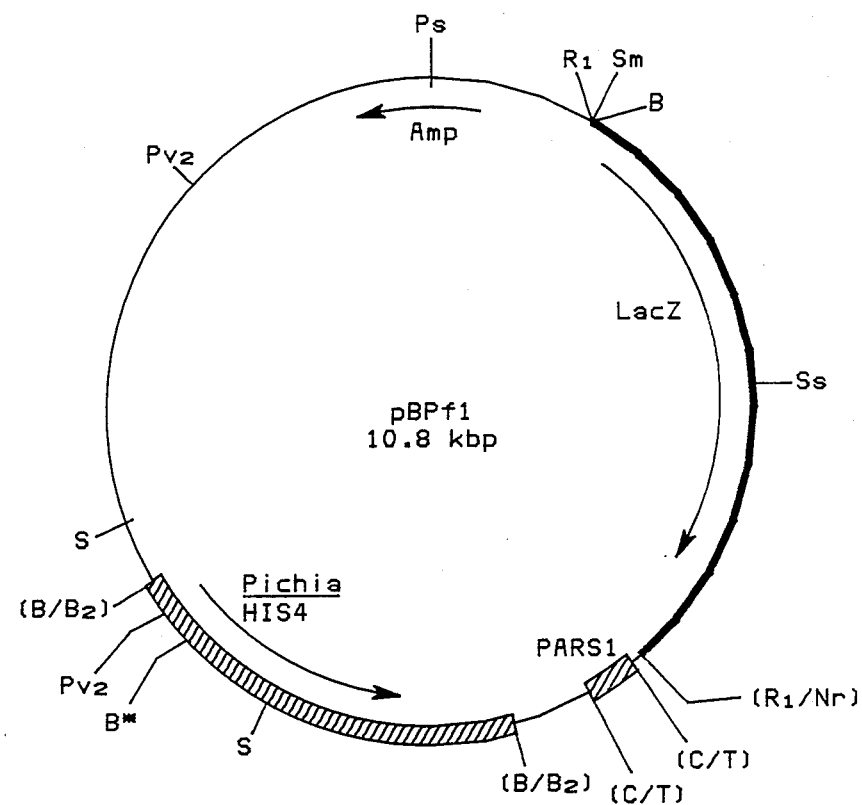
FIG. 34 is a restriction map of pBPf1.

One of the putative Pichia autonomous replication sequences (PARS1) was cloned into several other Pichia vectors to examine its ability to maintain the transforming DNA as an autonomous element. Plasmids pYJ30 (FIG. 27) and pBPf1 (FIG. 34) were still present as autonomous elements after 20 generations of growth on selective media (His−) and were present in multicopies per cell. Southern blot analysis of cells transformed with pYJ30 indicate about 10 copies per cell.

To determine if plasmids pSAOH5 (see FIG. 18) and pT76H4 (See FIG. 22b), which contain PARS1 contributed by pYJ30 and pBPf1, respectively, display similar stability to the plasmids from which they were derived. Cells containing these vectors were grown under selective conditions for about 50 generations under selective conditions (His−) in the presence of glucose. The cells were then shifted to non-selective conditions (His+) and the loss of prototrophy was monitored. The stability of these plasmids was comparable to the stability of pYJ30, including the rapid loss of His protrotrophy upon shift to non-selective media.

Thus, it is believed that experiments carried out with plasmids containing the autonomous replication sequence, PARS1, provide results of gene expression from autonomous plasmid DNA.

Novel β-Galactosidase Gene Containing Constructs

In order to demonstrate the ability of the regulatory regions of the present invention to control the production of protein products, novel DNA constructs were prepared. Thus the E. coli lacZ gene was placed in several plasmids under the control of the regulatory regions of the genes encoding polypeptide p72 (alcohol oxidase) or p76. The preparation of plasmids pSAOH1, pSAOH5, pSAOH10, pTAFH.85, pT76H1, pT76H2, pT76H3, and pT76H4 is described in Example XIV.

Although the introduction of the regulatory region-β-galactosidase gene fusions of the invention into host yeast cells is described herein employing plasmids as the vehicle for introduction, those of skill in the art recognize that it is not necessary for the regulatory region-structural gene construct to be introduced into the cell via a plasmid. Hence, any molecule capable of being maintained in yeast can be employed. Therefore, the regulatory region-structural gene constructs of the invention can be manipulated via vectors other than plasmids. Alternatively, the regulatory region-structural gene construct can be integrated into the chromosome of the host yeast cell.

Those of skill in the art also recognize that the scope of the present invention is not limited to the production of β-galactosidase under the regulation of the regulatory regions disclosed herein. The variety of polypeptides which can be produced under the regulation of the regulatory regions of the invention is limited only by the imagination of the reader. Many procedures exist for the preparation of DNA sequences which code for desired polypeptides. For example, oligonucleotides of various lengths can be synthesized by known procedures. Several such oligonucleotides can be assembled, in consequence of the specific base pairing properties thereof, into longer, double-stranded molecules. The component oligonucleotides of this double-stranded molecule can be joined (ligated) by the enzyme DNA ligase. Alternatively, DNA molecules having the desired coding sequence can be synthesized by use of the enzyme reverse transcriptase, using messenger RNA related to the desired polypeptide as a template for the action of reverse transcriptase. Yet another possibility is the cloning of genomic DNA fragments and observing whether direct expression of the desired product occurs.

The DNA sequence which codes for the desired polypeptide can be modified for preparation of the regulatory region-structural gene construct by a variety of procedures. For example, the ends of the DNA prepared as described above can be ligated with the enzyme DNA ligase to short double-stranded DNA molecules which contain the nucleotide sequence recognized by specific restriction endonucleases, so called linker molecules. Digestion of these molecules with a specific restriction endonuclease following the ligation will generate termini corresponding to the specified restriction endonuclease recognition site at the ends of the prepared DNA sequence.

Figure 15:
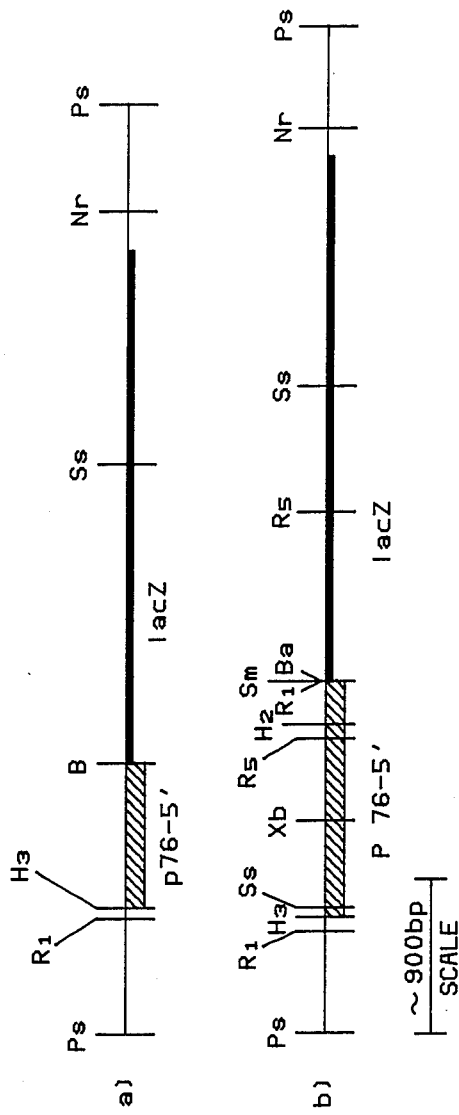
FIG. 15 provides restriction maps of two novel p76 regulatory region-lacZ DNA constructs of the invention.
Figure 16:
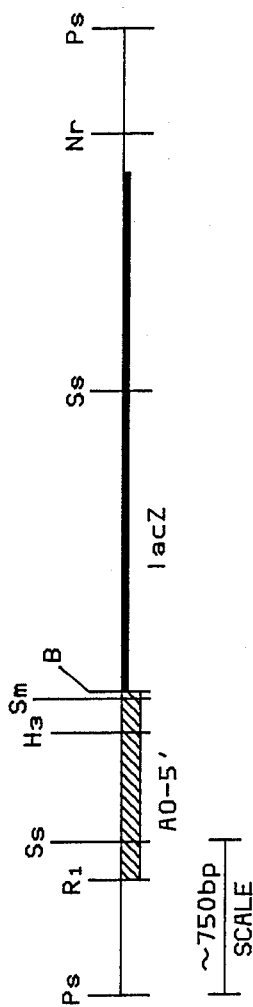
FIG. 16 is a restriction map of a novel p72 (alcohol oxidase) regulatory region-lacZ DNA construct of the invention.

Three specific regulatory region-β-galactosidase gene constructs prepared in the course of this work are described in terms of restriction mapping data presented in FIGS. 15 and 16. The restriction map presented in FIG. 15a describes a construct comprising a 0.85 kilobase pair HindIII-BamHI portion derived from the 5' regulatory region of pPG 6.0 and the lacZ gene from E. coli (the 3.6 kilobase pair BamHI-NruI fragment shown). This same construct is present in each of the plasmids pTAFH,85, pT76H1 and pT76 H2, to be described in greater detail below. (See Example XIV). The restriction map presented in FIG. 15b describes a construct comprising a 1.3 kilobase pair HindIII-EcoRI portion derived from the 5' regulatory region of pPG 6.0 and the lacZ gene from E. coli. This same construct is present in each of the plasmids pT76U1, pT76H3 and pT6H4, to be described in greater detail below (see Example XIV).

FIG. 16 is a restriction map of a construct comprising a 1.1 kilobase pair EcoRI-BamHI fragment derived from a portion of the 5' regulatory region of pPG 4.0 and the lacZ gene from E. coli. This construct is present in each of the plasmids pSAOH1, PSAOH5 and pSAOH10, to be described in greater detail below. (See example XIV).

Figure 17:
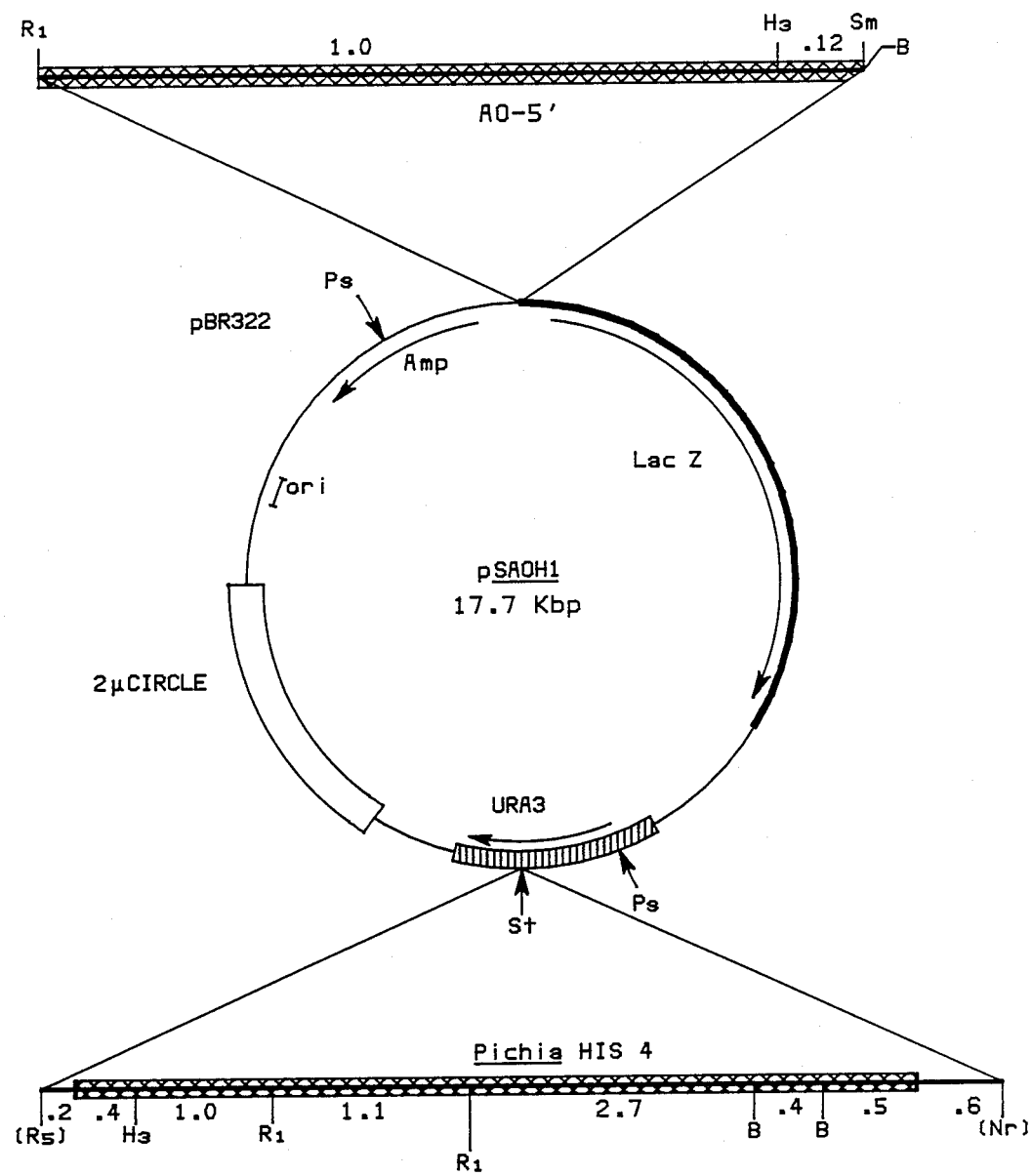
FIG. 17 is a restriction map of plasmid pSAOH 1.

Plasmid pSAOH1 is illustrated schematically in FIG. 17. In addition to containing the regulatory region-β-galactosidase gene fusion detained in FIG. 16, the plasmid is shown to contain:

(a) pBR322 sequences, including the Amp$^R$ gene;
(b) Pichia pastoris HIS4 gene;
(c) S. cerevisiae 2μ circle DNA; and
(d) the interrupted URA3 gene from S. cerevisiae.

The plasmid therefore has the capability to transform and replicate in E. coli hosts and yeast hosts. Selectable markers are present for manipulation of the DNA in either E. coli or yeast hosts.

Figure 18:
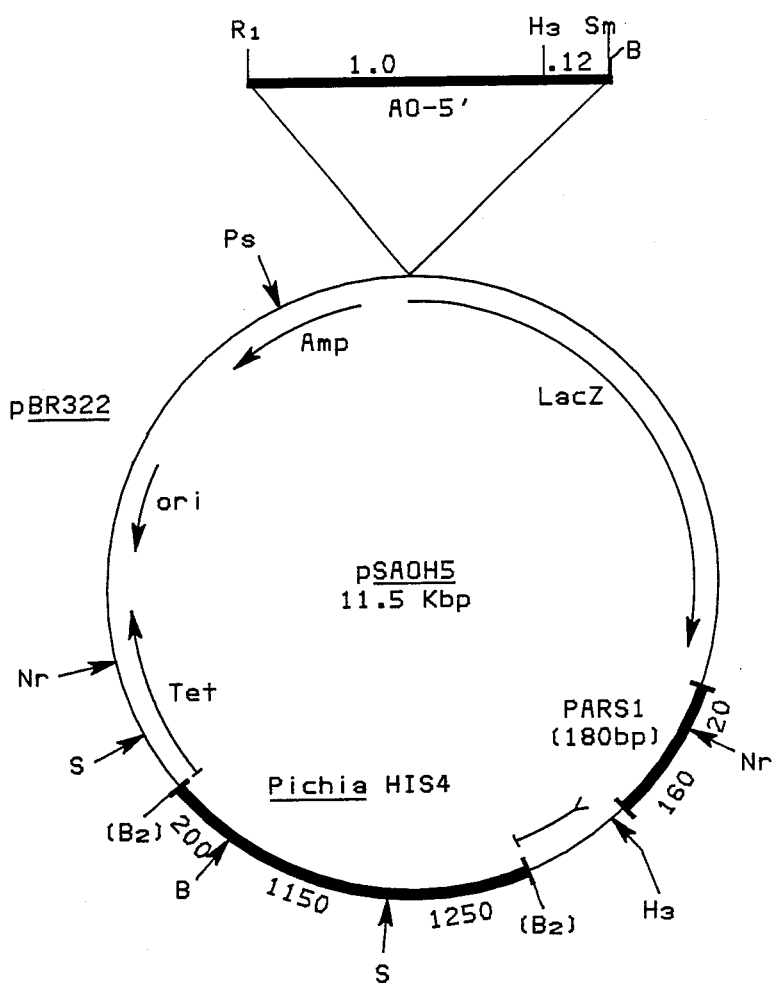
FIG. 18 is a restriction map of plasmid pSAOH 5.

Plasmid pSAOH5 is illustrated schematically in FIG. 18. The plasmid is similar to pSAOH1 described above, except the S. cerevisiae 2μ circle DNA and some of the Pichia pastoris HIS4 gene flanking DNA has been deleted while a Pichia pastoris autonomously replicating sequence (PARS1 from pYA63) has been added.

Figure 19:
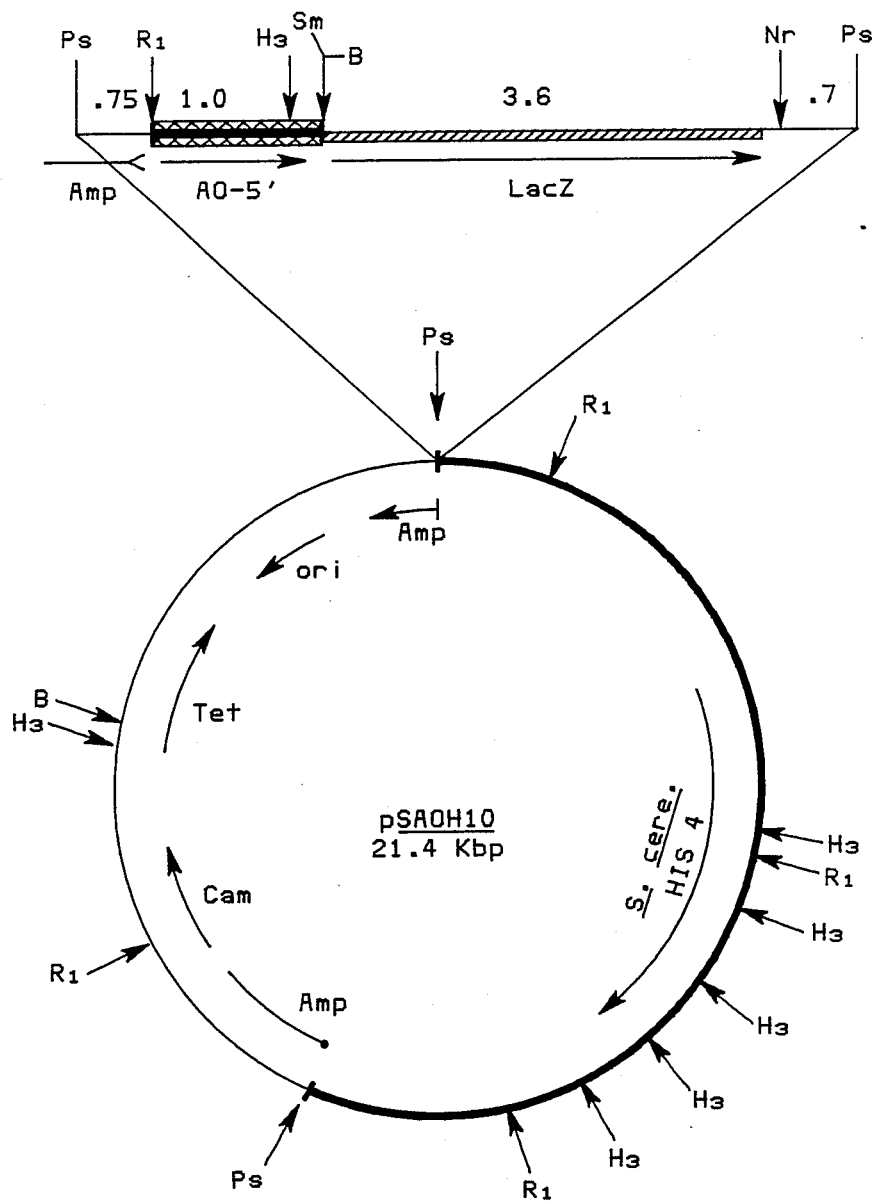
FIG. 19 is a restriction map of plasmid pSAOH 10.

Plasmid pSAOH10 is illustrated schematically in FIG. 19. The plasmid contains:

(a) regulatory region-β- galactosidase gene fusion;
(b) pBR325 sequences, including genes conferring tetracycline resistance, chloramphenicol resistance and ampicillin resistance ($tet^R$, $cam^R$ and $amp^R$, respectively); and (c) S. cerevisiae HIS4 gene (obtained from plasmid pYA2 as described below).

Plasmids pTAFH.85, pT76H1 and pT76H2 are analogous to the above three described plasmids, except the regulatory region-β-galactosidase gene fusion employed was that described in FIG. 15a (instead of the fusion described in FIG. 16).

Plasmids pT76H3 and pT76H4 are analogous to pSAOH1 and pSAOH5, respectively, except the regulatory region-β-galactosidase gene fusion employed was that described in FIG. 15b (instead of the fusion described in FIG. 16).

Figure 20:
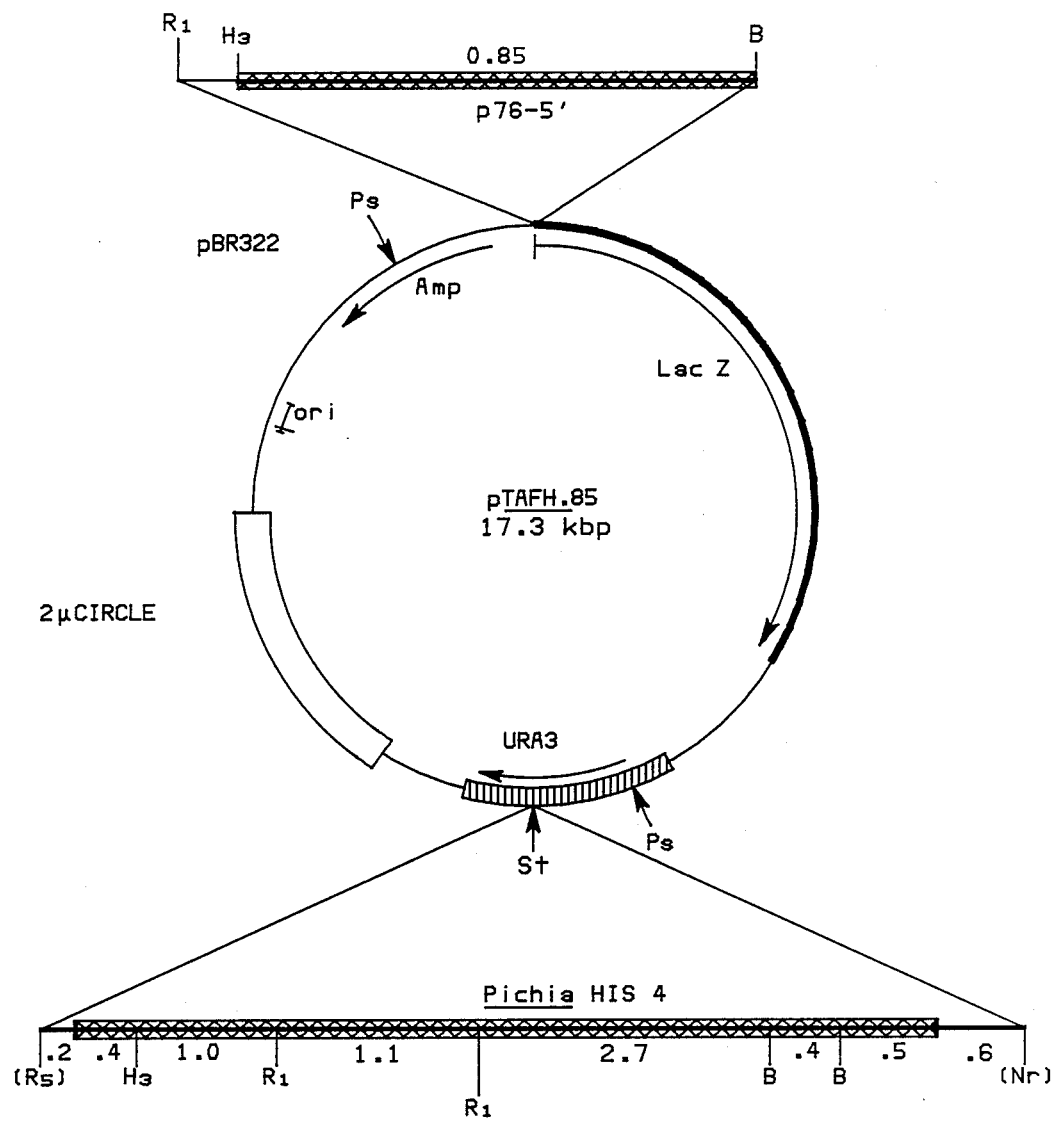
FIG. 20 is a restriction map of plasmid pTAFH.85.

Plasmid pTAFH.85 is illustrated schematically in FIG. 20 and comprises:

(a) the regulatory region-β-galactosidase gene fusion shown in FIG. 15a;
(b) pBR322 sequences, including the $amp^R$ gene;
(c) Pichia pastoris HIS4 gene;
(d) S. cerevisiae 2μ circle DNA; and
(e) the interrupted URA3 gene from S. cerevisiae.

Figure 21:
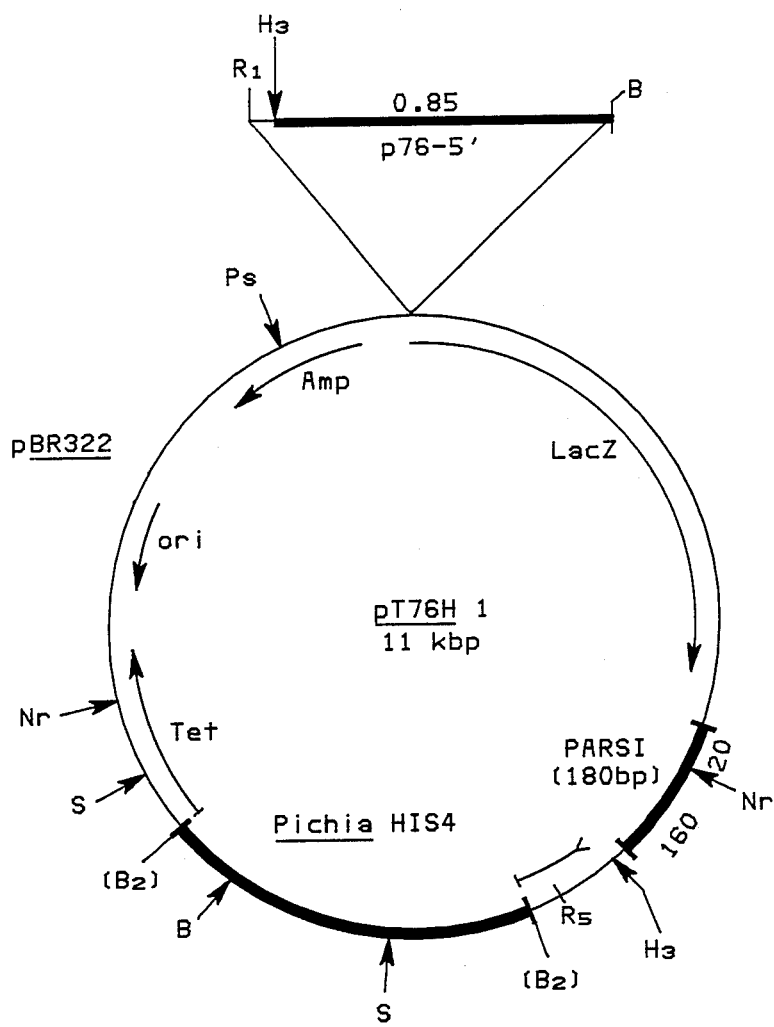
FIG. 21 is a restriction map of plasmid pT76H 1.

Plasmid pT76H1 is illustrated schematically in FIG. 21 and comprises:

(a) the regulatory region-β-galactosidase gene fusion shown in FIG. 15a;
(b) pBR322 sequences, including the $amp^R$ gene; and
(c) Pichia pastoris HIS4 gene and autonomously replicating sequence (PARS1).

Figure 22:
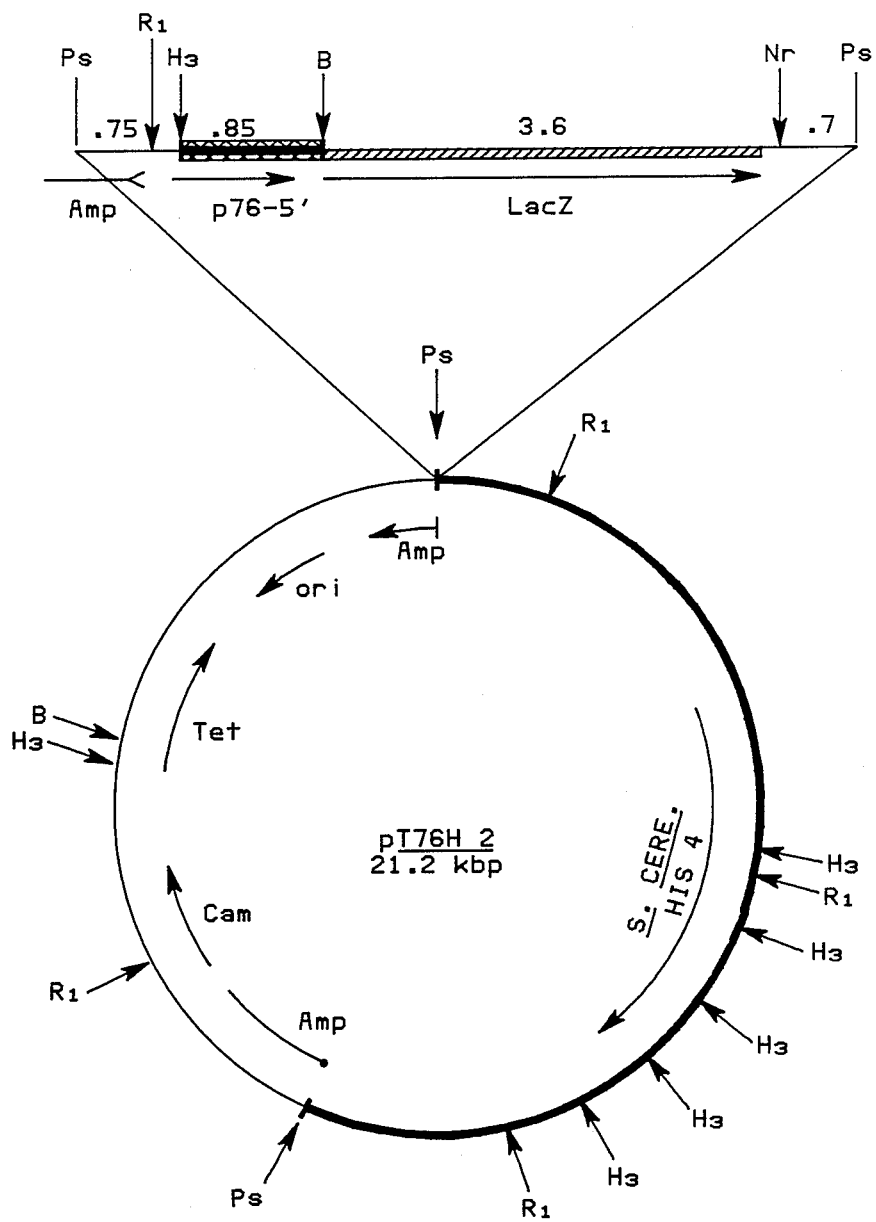
FIG. 22 is a restriction map of plasmid pT76H 2.

Plasmid pT76H2 is illustrated schematically in FIG. 22 and comprises:

(a) the regulatory region-β-galactosidase gene fusion shown in FIG. 15a;
(b) pBR325 sequences, including genes conferring tetracycline resistance, chloramphenicol resistance and ampicillin resistance; and
(c) S. cerevisiae HIS4 gene.

Figure 22A:
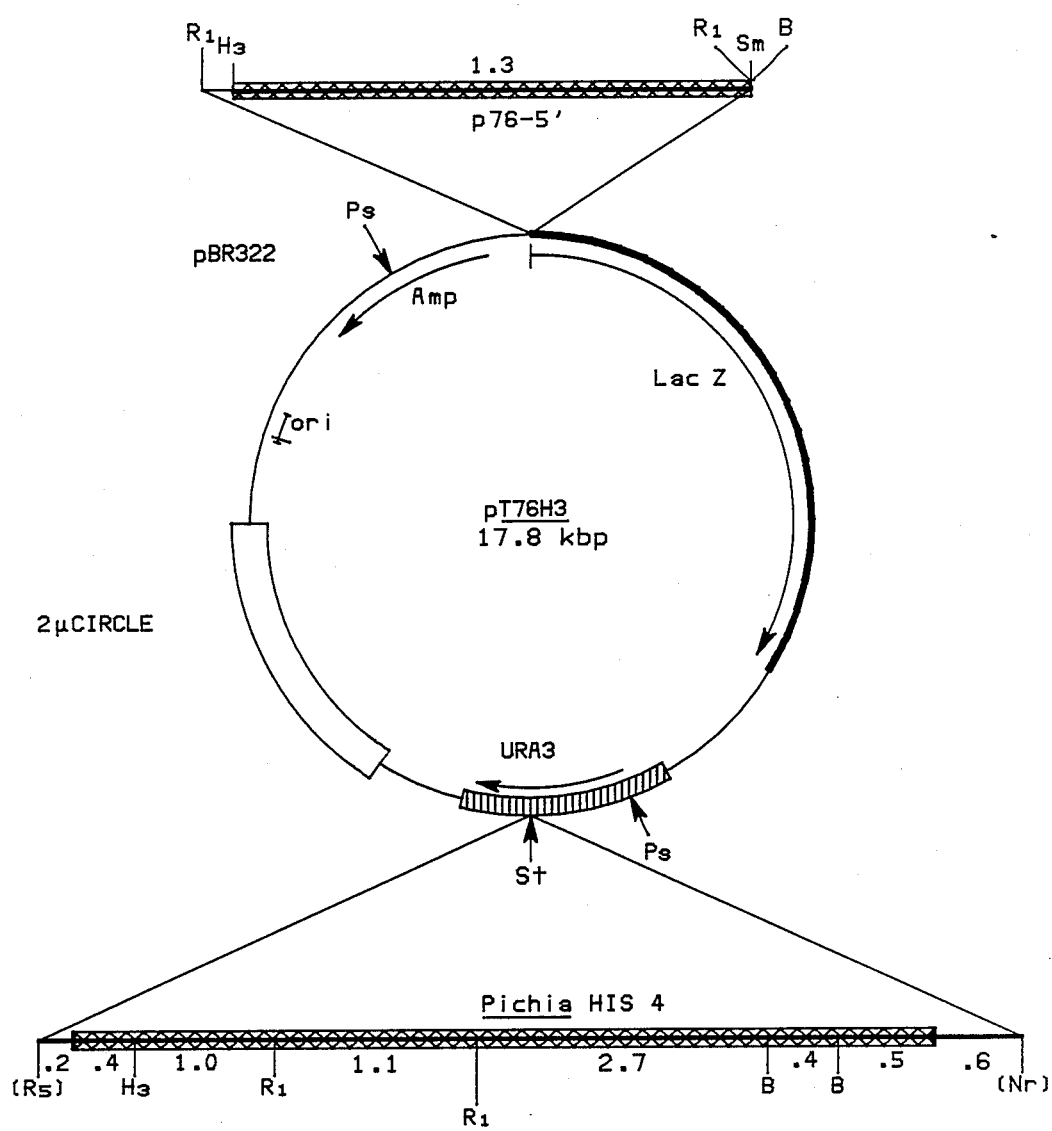
FIG. 22a is a restriction map of plasmid pT76H3.

Plasmid pT76H3 is illustrated schematically in FIG. 22a and comprises:

(a) the regulatory region-β-galactosidase gene fusion shown in FIG. 15b;
(b) pBR322 sequences, including the $amp^R$ gene;
(c) P. pastoris HIS4 gene;
(d) S. cerevisiae 2μ circle DNA; and
(e) the interrupted URA3 gene from S. cerevisiae.

Figure 22B:
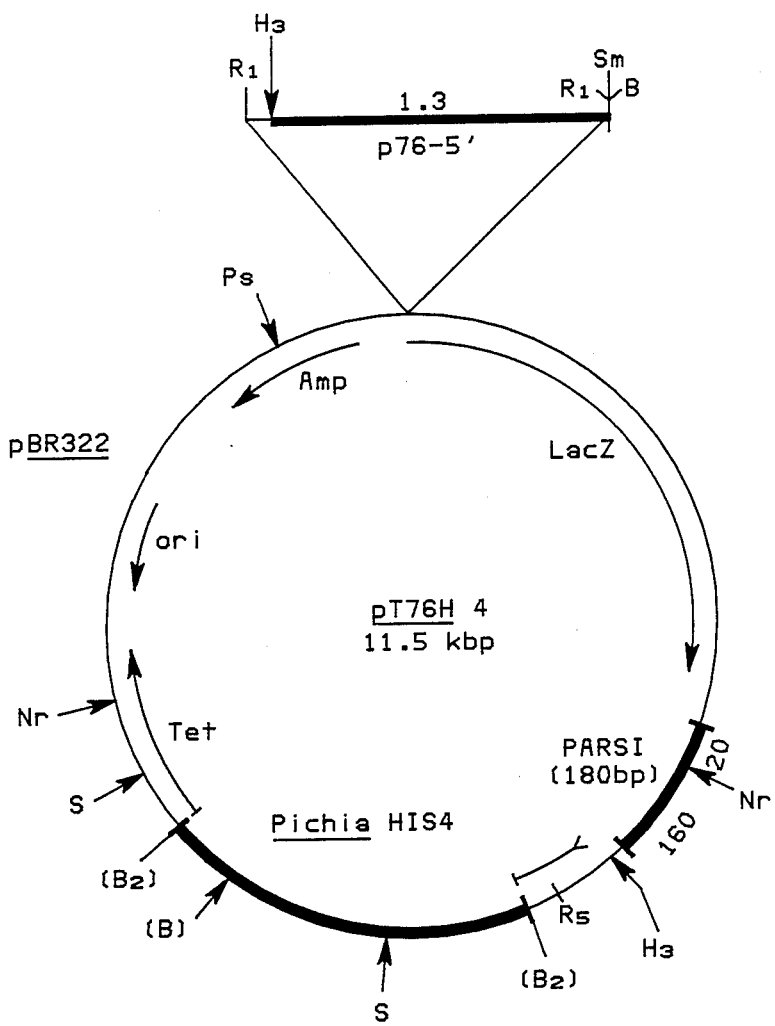
FIG. 22b is a restriction map of plasmid pT76H4.

Plasmid pT76H4 is illustrated schematically in FIG. 22b and comprises:

(a) the regulatory region-β-galactosidase gene fusion shown in FIG. 15b;
(b) pBR322 sequences, including the $amp^R$ gene;
(c) Pichia pastoris HIS4 gene; and
(d) Pichia pastoris autonomous replication sequence (PARS1).

Expression of β-Galactosidase in Yeast

Pichia pastoris GS115 (NRRL Y-15851) was transformed with the novel β-galactosidase gene-containing constructs described above. Several of the resulting transformed yeast strains have been deposited with the Northern Regional Research Center of the United States Department of Agriculture and assigned deposit accession numbers as follows:

| Host | Plasmid | Accession Number of Transformed Strain |
|---|---|---|
| GS115 | pSAOH1 | NRRL Y-15852 |
| GS115 | pSAOH5 | NRRL Y-15853 |
| GS115 | pSAOH10 | NRRL Y-15854 |
| GS115 | pTAFH.85 | NRRL Y-15855 |
| GS115 | pT76H1 | NRRL Y-15856 |
| GS115 | pT76H2 | NRRL Y-15857 |

The novel β-galactosidase gene-containing constructs were also used to transform E. coli. Transformed bacterial strains have also been deposited with the Northern Regional Research Center in Peoria, Ill. to insure availability to the public upon issuance of this application as a patent. The transformed strains have been assigned the following accession numbers:

| Host | Plasmid | Accession Number of Transformed Strain |
|---|---|---|
| MC1061 | pSAOH1 | NRRL B-15861 |
| MC1061 | pSAOH5 | NRRL B-15862 |
| MC1061 | pSAOH10 | NRRL B-15863 |
| MC1061 | pTAFH.85 | NRRL B-15864 |
| MC1061 | pT76H1 | NRRL B-15865 |
| MC1061 | pT76H2 | NRRL B-15866 |
| MC1061 | pTAO13 | NRRL B-15875 |
| MC1061 | pT76H3 | NRRL B-18000 |
| MC1061 | pT76H4 | NRRL B-18001 |
| MC1061 | pT76U1 | NRRI B-18002 |

Pichia pastoris GS115(NRRL Y-15851) transformed with each of the first eight plasmids described above which contain the alcohol oxidase and p76 regulatory region-lacZ gene fusions of the invention were grown to stationary phase on minimal medium supplemented with biotin plus glucose as carbon source. Once cells reached stationary phase, they were shifted to minimal medium supplemented with biotin plus methanol as carbon source. After cells had grown for about 3-5 generations at 30° C., they were shifted to fresh minimal medium supplemented with biotin and grown on glucose or methanol as carbon source. At distinct time points, culture samples were withdrawn and analyzed for the presence of β-galactosidase and alcohol oxidase by methods detailed in Examples VII and XV.

It was found that cells grown on glucose as carbon source produced no detectable levels of β-galactosidase or alcohol oxidase, while cells grown on methanol as sole carbon source expressed significant levels of both alcohol oxidase and β-galactosidase. It was also found that the glucose grown cells, when subjected to conditions of carbon source starvation, also expressed measurable quantities of alcohol oxidase as well as β-galactosidase. Thus, it is clear that the regulatory regions of the invention are responsive to both the presence of methanol as well as conditions of carbon source starvation.

As verification that the regulatory regions of the invention are responsive to growth on non-catabolite repressing carbon sources as well as conditions of carbon source starvation, a plasmid containing the alcohol oxidase regulatory region, pTAO13; and a plasmid containing the p76 regulatory region, pT76U1, was used to transform a non-methanol utilizing strain of yeast, Saccharomyces cerevisiae. One of the transformed strains employed, having the laboratory designation of SEY2102-pTAO13 has been deposited with the Northern Regional Research Center in Peoria, Ill. to insure access to the public upon granting of a patent on this application. The transformed strain has been assigned accession number NRRL Y-15858. *Saccharomyces cerevisiae* NRRL Y-15858 and SEY2102-pT76U1 were grown up on glucose, fructose, ethanol, glycerol and galactose for about five generations then subjected to conditions of carbon source starvation. The usual assay for β-galactosidase (See Example XV) after five generations indicated that glycerol and galactose grown cells produced large amounts of β-galactosidase while glucose and fructose grown cells produced essentially no β-galactosidase. When β-galactosidase was measured after 6 hours under carbon source starvation, the production of moderate quantities of β-galactosidase by the transformed organisms grown on glucose and fructose as well as substantial quantities of β-galactosidase produced by glycerol and galactose grown cells was observed. Thus, the regulatory regions of the invention are capable of controlling the production of protein products in genetically very diverse yeast hosts and are not limited to utilization in methanol utilizing strains.

EXAMPLES

The buffers and solutions employed in the following examples have the compositions given below:

| | |
|---|---|
| 1$\underline{M}$ Tris buffer | 121.1 g Tris base in 800 mL of H$_2$O; adjust pH to the desired value by adding concentrated (35%) aqueous HCl; allow solution to cool to room temperature before final pH adjustment, dilute to a final volume of 1L. |
| S-buffer | 1.5 $\underline{M}$ sorbitol in 0.04 $\underline{M}$ sodium phosphate buffer at pH 6.6. |
| PK buffer | 0.14 $\underline{M}$ NaCl 1% Sodium dodecylsulfate (SDS) 0.01 $\underline{M}$ EDTA in 0.05 $\underline{M}$ (pH 8.4) Tris buffer |
| ETS buffer | 10 m$\underline{M}$ EDTA 0.2% SDS in 0.01 $\underline{M}$ (pH 7.4) Tris buffer |
| TE buffer | 1.0 m$\underline{M}$ EDTA in 0.01 $\underline{M}$ (pH 7.4) Tris buffer |
| SSC | 0.15 $\underline{M}$ NaCl 15 m$\underline{M}$ sodium citrate adjusted to pH 7.0 with NaOH |
| TAE | 40 m$\underline{M}$ acetic acid 5 m$\underline{M}$ EDTA in 0.02 $\underline{M}$ (pH 8.3) Tris buffer |
| PBS (Phosphate buffered saline) | 10 m$\underline{M}$ sodium phosphate (pH 7.0) 0.15 $\underline{M}$ NaCl |
| Laemmli Loading Buffer | 62.5 m$\underline{M}$ Tris-HCl (pH 6.8) 2% SDS 10% glycerol 5% 2-mercaptoethanol 0.01% bromphenol blue |
| RIPA Buffer | 1% NP40 (Sigma) 1% sodium deoxycholate 0.1% SDS in PBS |
| 20xSSPE | 20 m$\underline{M}$ EDTA 0.16 $\underline{M}$ NaOH 0.2 $\underline{M}$ NaH$_2$PO$_4$ · H$_2$O 3.6 $\underline{M}$ NaCl adjusted pH to 7.0 with NaOH |
| Denhardts' Solution (50x) | 5 g Ficoll 5 g polyvinylpyrrolidone 5 g Bovine serum albumin (BSA; Pentax Fraction V) brought to a total volume of 500 mL with water |
| Prehybridization buffer | 5x SSPE 5x Denhardt's solution 50% deionized formamide 0.2% SDS 200 μg/mL sheared and denatured herring sperm DNA |
| LB (Luria-Bertani) Medium | 5 g Bacto-tryptone 5 g Bacto-yeast extract 2.5 g NaCl in 1 L of water, adjusted to pH 7.5 with NaOH |
| YPD Medium | 1% Bacto-yeast extract 2% Bacto-peptone 2% Dextrose |
| SD Medium | 6.75 g yeast nitrogen base without amino acids (DIFCO) 2% Dextrose in 1 L of water |
| SED | 1 $\underline{M}$ Sorbitol 25 m$\underline{M}$ EDTA 50 m$\underline{M}$ DTT |
| SCE Buffer | 9.1 g Sorbitol 1.47 g Sodium citrate 0.168 g EDTA 50 mL H$_2$O pH to 5.8 with HCl |
| CaS | 1 $\underline{M}$ Sorbitol 10 m$\underline{M}$ CaCl$_2$ filter sterilize |
| PEG Solution | 20% polyethylene glycol-3350 10 m$\underline{M}$ CaCl$_2$ 10 m$\underline{M}$ Tris-HCl (pH 7.4) filter sterilize |
| SOS | 1 $\underline{M}$ Sorbitol 0.3x YPD medium 10 m$\underline{M}$ CaCl$_2$ |
| Formamide dye mix | 0.1% xylene cylenol FF 0.2% bromphenol blue 10 m$\underline{M}$ EDTA 95% deionized formamide |
| Top gel | 76.8 gm urea 24 mL acrylamide stock 8 mL 10x TBE bring to final volume of 160 mL |
| Acrylamide stock | 38 gm acrylamide 2 gm bis(N,N—methylenebisacrylamide) add water to total volume of 100 mL |
| Bottom gel | 14.4 gm urea 3.0 gm sucrose 7.5 mL 10x TBE 4.5 mL acrylamide stock 0.3 mL bromphenol blue solution (0.01 g/mL) add water to give total volume of 30 mL |
| Prehybridization Buffer for hybridization selection | 50% formamide 0.75% $\underline{M}$ NaCl 0.1 $\underline{M}$ TRIS, pH 7.4 0.008 $\underline{M}$ EDTA 0.5% SDS 200 μg/mL rabbit liver tRNAs (Sigma) |
| 0.5 $\underline{M}$ NETS Buffer | 0.5 $\underline{M}$ NaCl 10 m$\underline{M}$ EDTA 10 m$\underline{M}$ TRIS, pH 7.4 0.2% SDS |
| 10X RT Buffer | 500 m$\underline{M}$ NaCl 340 m$\underline{M}$ TRIS, pH 8.3 60 m$\underline{M}$ MgCl$_2$ 50 m$\underline{M}$ DTT (dithiothreitol) |
| dil RT | 4 μL H$_2$O 1 μL 10X RT Buffer 5 μL reverse transcriptase, 15 U/μL (Life Sciences, Inc.) |
| dideoxy: dd ATP dd CTP dd GTP dd TTP | 0.49 m$\underline{M}$ 0.1165 m$\underline{M}$ 0.369 m$\underline{M}$ 0.82 m$\underline{M}$ |
| dNTP mix | 0.625 m$\underline{M}$ dGTP 0.625 m$\underline{M}$ dATP 0.625 m$\underline{M}$ TTP |
| Chase | 1.125 m$\underline{M}$ dATP 1.125 m$\underline{M}$ dCTP |

-continued 1.125 mM dGTP
1.125 mM TTP
in 1X RT buffer

Unless otherwise specified, the above solutions represent the basic (1×) concentration employed. Throughout the examples, where the different concentration levels are employed, that fact is indicated by referring to the solution as a multiple of the basic (1×) concentration.

The following abbreviations are used throughout the examples, with the following meaning:

| | | |
|---|---|---|
| EDTA | | ethylenediamine tetraacetic acid |
| TEMED | | N,N,N',N'—tetramethylenediamine |
| DTT | | dithiothreitol |
| BSA | | bovine serum albumin |
| EtBr | | ethidium bromide |
| Ci | | Curie |
| dATP | | deoxyadenosine triphosphate |
| dGTP | | deoxyguanosine triphosphate |
| TTP | | thymidine triphosphate |
| dCTP | | deoxycytidine triphosphate |
| dXTP | | "generic" deoxy triphosphate nucleotide |
| oligo(dT)12-18 | Source: | Collaborative Research, Inc. |
| Zymolyase 60,000 | Source: | Miles Laboratories |

Several procedures carried out on a routine basis follow a standard protocol which will be detailed here.

Centrifugation is carried out for a period of time and at a spin rate sufficient to provide a clear supernatant. Generally, centrifugation of yeast cells is carried out at at least 1500 g for at least 5 minutes.

Nucleic acid extractions with phenol/chloroform/isoamyl alcohol involve contacting the nucleic acid containing solution with and equal volume of a 50:48:2 ratio by volume mixture of phenol, chloroform and isoamyl alcohol, respectively. Extractions with chloroform/isoamyl alcohol involve contacting the solution to be treated with an equal volume of 48:2 ratio by volume mixture of chloroform and isoamyl alcohol.

When gels, filters, etc. are described as being washed or soaked in a specified solution, the entire gel, filter, or the like was immersed in an appropriate vessel (pan, dish, vial, etc.) in order to contact the entire surface of the gel, filter, or the like with the solution of interest.

Ethanol precipitation of nucleic acids involves first adjusting the salt content of the nucleic acid-containing solution, then contacting the solution with two volumes of cold ethanol.

EXAMPLE I

Growth and Preparation of Yeast Cells

*Pichia pastoris* NRRL Y-11430 was grown under carbon limited conditions in continuous culture at 30° C. with either methanol or ethanol as sole carbon source in IM1 salts minimal medium as described by Wegner in U.S. Pat. No. 4,414,329. IM1 minimal media contains, per liter of media, 36 mM KH$_2$PO$_4$, 23 mM (NH$_4$)$_2$SO$_4$, 2 mM MgSO$_4$, 6.7 mM KCl, 0.7 mM CaCl$_2$, 0.2 μM CUSO$_4$·5 H$_2$O, 1.25 μM KI, 4.5 μM MnSO$_4$, 2 μM Na$_2$MoO$_4$, 0.75 μM H$_3$BO$_3$, 17.5 μM ZnSO$_4$, 44.5 μM FeCl$_2$ and 1.6 μM biotin. The cells grown on methanol were grown up to a cell density of 140 g/L (dry weight) with a retention time of about 12 hours. The cells grown on ethanol were grown up to a cell density of 90 g/L with a retention time of about 11.5 hours. When methanol or ethanol were fed into the fermenter, feed stocks containing concentrations of 20% and 45% alcohol, respectively, were used.

Ten grams of fermenter grown *Pichia pastoris* cells were collected by centrifugation and resuspended at approximately 10$^8$ cells/mL in 0.1 M Tris (pH 8.0) containing 1% 2-mercaptoethanol. These cells were incubated for 5 to 10 minutes at 37° C. and collected by centrifugation. The pellet was washed once with 30 mL of S-buffer and resuspended in 5 mL of S-buffer per gram of cells. Zymolyase (Miles Biochemicals) was added to the cell suspension to give a final concentration of 500 μg/mL. The cells were incubated at 37° C. for 20 minutes and then centrifuged; supernatant discarded and the cell pellet collected. This pellet was frozen in liquid nitrogen and stored at −70° C. for later use.

EXAMPLE II

Isolation of Yeast RNA

Total cell RNA was prepared by pulverizing the frozen pellet prepared as described in Example I with a mortar and pestle and further disrupting the frozen pellet for about 2–5 minutes in a Waring Blender in the presence of liquid nitrogen. The pulverized pellet was added to PK buffer at a concentration of 7.5 mL per gram of cells. Proteinase K (Boehringer Mannheim) was added to the resuspended pellet to give a final concentration of 400 μg/mL, and the suspension was incubated at room temperature for 10 minutes. This mixture was extracted with phenol/chloroform/isoamyl alcohol followed by a chloroform/isomayl alcohol extraction. Nucleic acids were precipitated by adjusting the solution to be 0.25 M NaCl and adding ethanol. The pellet was resuspended in a minimum volume of ETC buffer, i.e. that volume of buffer sufficient to dissolve the nucleic acids; generally about 100 μg up to about 1 mg of DNA per mL of solution. This solution was re-extracted with phenol/chloroform/isoamyl alcohol, then chloroform/isoamyl alcohol and finally precipitated with ethanol.

The nucleic acids were redissolved in a minimum volume of TE buffer. The RNA present in this solution was enriched either by centrifugation through a 4 mL CsCl cushion (1 g CsCl/mL, 1 mM EDTA, in 10 mM Tris (pH 7.4) buffer, or by precipitation by making the solution 2 M LiCl, maintaining at 4–8° C. overnight and collected by centrifugation. The poly A+ RNA was selected from the solution by affinity chromatography on oligo(dT)cellulose columns. Generally, 0.25 gm of oligo (dT) cellulose, type 3 (Collaborative Research) was prepared for chromatography per 5 to 10 mg of total RNA. 0.25 g of oligo (dT) cellulose was slurried in 2 mL of ETC buffer and poured into a small, siliconized glass column. This oligo (dT) cellulose column was washed by layering 10 mL of 0.1 M NaOH over the oligo (dT) cellulose and allowing the wash solution to flow through the oligo (dT) cellulose matrix. The oligo (dT) cellulose was then washed in the same manner with 10 mL of ETC buffer and washed a final time with 10 mL of 0.5 M NETS buffer.

Total RNA (5 to 10 mg) was resuspended in ETC buffer at a concentration not greater than about 10 mg/mL, placed in a 65° C. water bath for 2 minutes and then placed immediately on ice. The RNA solution was then allowed to warm to room temperature and a stock solution of 5 M NaCl was added to give a final salt concentration in the RNA solution of 0.5 M Nacl. The resulting RNA solution was layered onto the prepared oligo (dT) cellulose column and allowed to slowly flow through the column at a rate of about 1 drop/5 seconds. The material flowing out of the column bottom was collected in a tube and relayered onto the top of the column. The material collected from the column bottom was relayered on top a second time, resulting in the RNA solution being passed through the oligo (dT) cellulose column a total of three times. After the last pass through the column, the material was collected and labelled as the poly A—, i.e., non-poly A RNA. The column was then washed with 30 mL of 0.5 M NETS and finally the poly A+ RNA was eluted from the column by loading 5 mL of ETC buffer onto the column and allowing this buffer to flow through slowly, collecting the poly A+ RNA fraction in the 5 mL fraction flowing from the bottom of the column. Assuming that there was no NaCl in the poly A+ RNA fraction, the NaCl concentration of this fraction was adjusted to 0.25 M NaCl and RNA precipitated with ethanol.

EXAMPLE III

Construction of cDNA Library

Complementary DNA (cDNA) clones were synthesized as follows. Ten $\mu$g of poly A+ RNA prepared as described in Example II was resuspended in 7 $\mu$L H$_2$O and brought to a final concentration of 2.7 mM CH$_3$HgOH, then incubated at room temperature for 5 minutes. The first strand of cDNA was synthesized at 42° C. for 15 minutes in 50 $\mu$L of a solution containing 50 mM Tris, (pH 8.3) at 42° C., 10 mM Mgcl$_2$, 30 mM 2-mercaptoethanol, 70 mM KCl, 500 $\mu$M each of dATP, dGTP, and TTP, 200 $\mu$M dCTP, 25 $\mu$g/mL oligo(dT), 60 $\mu$g/mL actinomycin D, 25 units RNasin (Biotec, Inc.), 25 $\mu$Ci $\alpha$-$^{32}$P dCTP (32.5 pmoles), and 120 units of reverse transcriptase (Life Sciences Inc.). This reaction mix was incubated at 37° C. for an additional 15 minutes. The reaction was terminated by the addition of 2 $\mu$L of 0.5 M EDTA and 0.5 $\mu$L 20% SDS. The reaction was adjusted to 0.3 M NaOH and incubated at 65° C. for 30 minutes. The reaction mix was then neutralized by the addition of 10 $\mu$L of 1 M Tris, (pH 7.4) and adjusting the reaction mix to 0.21 M HCl. The reaction mix was phenol/chloroform/isoamyl alcohol extracted, then chloroform/isoamyl alcohol extracted and finally chromatographed over a Sephadex G50 column in TE buffer. The radioactive single-stranded cDNA was pooled into one fraction and concentrated to 100 $\mu$L either by butanol extraction or evaporation by centrifugation under vacuum. The single stranded cDNA was ethanol precipitated from the concentrated solution, cDNA collected by centrifugation and resuspended in 100 $\mu$L of water.

The aqueous single-stranded cDNA solution was adjusted to 2.5 M ammonium acetate, ethanol precipitated, collected by centrifugation and resuspended in 20 $\mu$L of water. This single stranded DNA solution was brought to a final volume of 50 $\mu$L with 50 mM potassium phosphate buffer (pH 7.4) containing 5 mM MgCl$_2$, 1 mM 2-mercaptoethanol, 250 $\mu$M each of dATP, dGTP, and TTP, 125 $\mu$M dCTP, 25 $\mu$Ci-$\alpha$-$^{32}$P-dCTP (32.5 pmoles), and 8 units of Klenow fragment DNA PolI (New England Biolabs). The resulting reaction mixture was incubated at 37° for one hour in order to synthesize the complementary second DNA strand to the single stranded cDNA. The reaction was terminated by the addition of 2 $\mu$L of 0.5 M EDTA. The double stranded cDNA was phenol/chloroform/isoamyl alcohol extracted, chloroform/isoamyl alcohol extracted and chromatographed over a Sephadex G50 column in TE buffer. The double stranded cDNA fractions were pooled and the pool was concentrated and precipitated as described for the single-stranded cDNA.

After the final ethanol precipitation and the collection of the double stranded cDNA by centrifugation, the pellet was resuspended in 20.25 $\mu$L of water, then brought to a final volume of 50 $\mu$L with 50 mM Tris, (pH 8.3 at 42° C.), containing 10 mM MgCl$_2$, 30 mM 2-mercaptoethanol, 70 mM KCl, 500 $\mu$M of dXTP, and 150 units of reverse transcriptase. The resulting solution was incubated at 42° C. for 15 minutes in order to insure completion of the synthesis of the second strand of cDNA. The reaction was terminated by the addition of 2 $\mu$L of 0.5 M EDTA and concentrated and precipitated as described for the single stranded cDNA reaction.

The double stranded cDNA pellet was resuspended in 42 $\mu$L of H$_2$O and the solution brought to a final volume of 47 $\mu$L by the addition of 5 $\mu$L of a stock solution containing 2.8 M NaCl, 200 mM NaOAc and 45 mM ZnSO$_4$, then adjusted to a pH of 4.5 at 22° with HCl. In order to digest the hairpin loop, three separate reactions were done with three different concentrations of S$_1$ nuclease (Sigma). One unit, 10 unit, 10 units or 100 units of S$_1$ nuclease were added to bring the reaction volume to 50 $\mu$L, and the reaction incubated at 22° C. for 30 minutes. The reaction was terminated by the addition of 2 $\mu$L of 0.5 M EDTA and 2.67 $\mu$L of 2 M Tris base. Six $\mu$g of rabbit liver tRNA were added as a carrier, and the reaction mixture was concentrated and precipitated as described above except the DNA pellets were resuspended in TE buffer rather than water. After the final precipitation, the pellet was resuspended in 20 $\mu$L of TE buffer and brought to a final volume of 50 $\mu$L in terminal transferase buffer (BRL) containing 10 pmoles of $\alpha$-$^{32}$P-dCTP, 2 $\mu$m dCTP and 21 units of terminal transferase (Ratliff Biochem). The resulting solution was incubated at 37° C. for 30 minutes in order to add poly d(C) tail to the 3'—OH end of the double-stranded cDNA. The reaction was terminated by the addition of 5 $\mu$L of 0.5 M EDTA, extracted, chromatographed, and stored as an ethanol precipitate.

The double stranded, d(C) tailed cDNA was either reannealed directly to poly d(G) tailed pBR322 opened at the PstI site or first size fractionated on a Sepharose CL4B-200 column (25 82L fractions). For the unfractionated library, 150 ng of double-stranded poly d(C) tailed cDNA were annealed in 180 $\mu$L of 10 mM Tris, (pH 7.4) which is 0.1 M in NaCl and 1 mM in EDTA to 900 ng of d(G) tailed pBR322 opened at the PstI site. Each 25 $\mu$L fraction of the fractionated library was annealed to 125 ng of poly d(G) tailed pBR322 in a 50 $\mu$L final volume of the same annealing mixture described above. The annealing reactions were incubated at 65° C. for 3 minutes, then 42° C. for 2 hours and allowed to cool slowly to room temperature.

The annealed cDNA library was transformed into competent *E. coli* LE392 (ATCC 33572) prepared as follows: An inoculum of LE392 was grown overnight at 37° C. in 2x LB media. Five mL of this overnight culture was inoculated into 200 mL of fresh 2x LB media and grown to an OD$_{600}$ of 0.2–0.3 at 37° C. This culture was placed on ice for 10 minutes and the cells were then collected by centrifugation at 4° C. The cell pellet was resuspended in 80 mL of ice cold 0.1 M CaCl$_2$ and incubated for 25 minutes at 4° C. The cells were collected by centrifugation at 4° C., the cell pellet resuspended in 2mL of ice cold 0.1 M CaCl$_2$ and incubated for at least 2 hours at 4° C. prior to use. Then 200 μL of competent cells per 50 μL of annealing mix were used for the transformation. The competent cells and the DNA were combined and incubated at about 4° C. for ten minutes, followed by an incubation at 37° C. for 5 minutes and finally placed on ice for 10 minutes. An equal volume of 2X LB media was added to the transformation mix and incubated at 37° C. for 45 minutes. The transformed cells were plated at 250 μL/plate on 150 mm 2x LB plates containing 15 μg/mL of tetracycline. The plates were incubated at 37° C. for 24 hours and stored at 4° C.

Replica filters were prepared by stamping nitrocellulose filters onto an original filter used to lift the colonies off of the plate. These replica filters were incubated on 2x LB-Tet (15 μg/mL of tetracycline) plates. The colonies on the filters were prepared for probing by transferring the filters to 2x LB-Tet plates containing 200 μg/mL of chloramphenicol, incubating the filters at 37° C. for at least 12 hours, then lysing the colonies by floating the filters on an aqueous pool which is 1.5 M NaCl and 0.5 M NaOH for 10 minutes. The filters were then neutralized by floating them on an aqueous pool which is 1.5 M NaCL and 0.5 M Tris, (pH 7.4) for 15 minutes and repeating this neutralization again. The filters were then air dried and finally dried under vacuum for 2 hours at 70° C.

EXAMPLE IV

Colony Hybridization

The vacuum dried nitrocellulose filters containing the cDNA library (prepared as described in the previous example) were prehyridized at 42° C. for 5 hours in prehybridization buffer. The filters were removed from the prehybridization buffer and lightly rubbed with a gloved hand in 5x SSPE in order to remove cell debris. The filters were placed in hydridization buffer (same as prehybridization buffer except 1x Denhardt's). Either $^{32}$P-labelled single-strand cDNA (10$^6$ cpm/mL) or end-labeled poly A+ RNA was hybridized to the filters for 17 hours at 42° C. After hybridization, the filters were washed briefly in 2x SSSPE at 22° C., followed by two washes at 65° C. in 0.1x SSPE, 10 minutes each.

End-labeling of poly A+ mRNA was performed by adding 2 μg of poly A+ mRNA to a volume of 50 μL containing 50 M Tris, (pH 9.5) heating to 100° C. for three minutes, and rapidly chilling on ice. This RNA solution was diluted to a final volume of 200 μL and adjusted to 50 mM Tris, (pH 9.5) 10 mM MgCl$_2$, 5 mM DDT and 50 pmoles of $^{32}$P-α-ATP. Ten units of T$_4$ polynucleotide kinase (Boehringer Mannheim) was added and the mixture incubated at 37° C. for one hour. The kinasing reaction was terminated by the addition of 10 μL of 0.5 M EDTA, extracted with phenol/chloroform/isomyl alcohol and chromatographed through Sephadex G50 to remove the unincorporated radioactive label.

EXAMPLE V

Northern Hybridizations

Two to five μg of poly A+ mRNA were heated at 65° C. for 5 minutes in 10 mM sodium phosphate buffer (pH 7.4) containing 50% formamide, 2.2 M formaldehyde, and 0.5 mM EDTA. The resulting solution was cooled to room temperature and an appropriate amount (generally about 0.2 volumes based on the volume of sample treated) of 5x sample buffer (0.5% SDS, 0.025% bromophenol blue, 25% glycerol, 25 mM EDTA) was added. The samples were loaded on a 1.5% agarose gel prepared in 10 mM sodium phosphate buffer (pH 7.4) containing 1.1 M formaldehyde, and electrophoresed in the same buffer. The gel was stained with acridine orange (33 μg/mL) in 10 mM sodium phosphate buffer (pH 7.4), destained by soaking the gel in the same buffer for 10 minutes, soaked in 10x SSPE for at least 10 minutes, and the RNA transferred to nitrocellulose as described in Example VI.

EXAMPLE VI

Isolation of Genomic DNA and Clones

Pichia genomic DNA was isolated using the method described in Example II for Pichia RNA isolation. The nucleic acid pellet was resuspended in a minimum volume TE buffer, and incubated with 20 μg/mL RNase A for 30 minutes at 37° C. The solution was brought to 0.14 M NaCl and treated with proteinase K at 200 μg/mL for 15 minutes at 22° C. The resulting solution was first extracted with phenol/chloroform/isoamyl alcohol and then with chloroform/isoamyl alcohol and finally ethanol precipitated. The precipitated DNA was resuspended in a minimum volume of TE buffer, and centrifuged in order to clear the DNA solution.

Ten μg of Pichia genomic DNA prepared as described in the previous paragraph was digested with various restriction enzymes (BRL) and electrophoresed on a 1% agarose gel containing TAE. The DNA fragments in the gel were denatured by soaking the gel in 1.5 M NaCl, 0.5 M NaOH for 20 minutes. The gel was neutralized by soaking in 1.5 M NaCl, 0.5 M Tris, (pH 7.4) for 20 minutes. Prior to transfer, the gel was soaked in 10x SSPE for at least 5 minutes. A sheet of nitrocellulose was cut to the size of the gel, wetted in water and soaked briefly in 10x SSPE. This filter was laid on top of the gel which in turn had been placed on a piece of parafilm. A sheet of Whatman filter paper and a stack of paper towels were placed on top of the nitrocellulose in order to draw the DNA out of the gel and transfer it to the nitrocellulose. A weight was placed on the stack to facilitate transfer. The DNA was allowed to transfer in this manner for at least 3 hours. After the transfer, the filter was soaked in 5x SSPE briefly, air dried, and dried under vacuum at 70° C. for 2 hours. Complementary genomic fragments were identified by hybridization to nick-translated cDNA clones pPC 8.0, pPC 6.4 and pPC 15.0 using the same prehybridization, hybridization, and washing buffers described in Example IV.

200 ng of the cDNA clones were nick-translated for 90 minutes at 14° C. in 30 μL of a solution containing 50 mM Tris-HCl (pH 7.4), 10 mM MgSO$_4$, 100 μM DTT, 50 μg/mL BSA, 20 μM each of dGTP, TTP and dATP, 31.25 pmoles $^{32}$P-α-dCTP (3200 Ci/mmol, NEN), 2 units *E. coli* DNA PolI (BRL), and 0.02 ng DNaseI. The reaction was terminated by the addition of 1 μL of 0.5 M EDTA and 1 μL of 20% SDS. The labelled DNA solution was brought to a final concentration of 0.3 M NaOH and placed in boiling water for 3 minutes. This mixture was chromatographed on a Sephadex G50 column. The labelled DNA fractions were pooled, the specific activity determined and the probe used in hydridization experiments.

Genomic fragments which hybridized to the cDNA probes were isolated by digesting 200 μg of Pichia genomic DNA with various restriction enzymes (BRL) and electrophoresing the digest on a 1% agarose gel in TAE buffer. The appropriate sized band was sliced from the agarose gel, the DNA electroeluted, passed through an Elutip column (Schleicher and Schuell) and ethanol precipitated.

The electroeluted fragments were resuspended in water and 200 ng fragments were ligated to 500 ng of pBR322 which was cleaved at the appropriate restriction site and dephosphorylated when necessary. The ligation reaction was carried out in 300 μL of 66 mM Tris, (pH 7.4) containing 6.6 mM MgCl$_2$, 10 mM DTT, 0.4 mM ATP, 25 μg/mL BSA, and 40–80 units of T4 DNA ligase, then incubated at 4° C. for 24 hours. The ligation mix was transformed directly into competent LE392 *E. coli* cells. The cells were made competent and the transformation done as described in Example III. A series of three transformations were done with 10, 40, and 100 ng of pBR322 (plus insert), each transformation in 100 μL of competent cells. The cells were plated as described in Example III except the antibiotic selection was 50 μg/mL of ampicillin. The clones were transferred to nitrocellulose, replicated and prepared for hybridization as described in Example III. The filters were probed with the appropriate nick-translated cDNA fragment. Streak-purified colonies which were positive in the hybridization were used to prepare additional plasmid, as follows.

The plasmid bearing LE392 *E. coli* was grown to an OD$_{600}$ of 1.0 in 1x LB media containing 50 μg/mL of ampicillin and amplified overnight by the addition of chloramphenicol to a final concentration of 200 μg/mL. The cells were washed in 0.8% NaCl, 20 mM Tris, (pH 8.0) 20 mM EDTA, then lysozome treated in 25% sucrose, 50 mM Tris, (pH 7.4) and 20 mM EDTA with 450 μg/mL lysozome. Lysis was achieved by adding 5 M NaCl to a final concentration of 2.0 M followed by the addition of an equal volume of 0.2% Triton X-100 and 40 mM EDTA. The preparation was cleared by spinning at 20,000 RPM for 45 minutes. The supernatant was then phenol/chloroform/isoamyl alcohol extracted, chloroform/isoamyl alcohol extracted and EtOH precipitated. The pellet was resuspended in TE buffer, RNase A treated, phenol/chloroform/isoamyl alcohol extracted and chloroform/isoamyl alcohol extracted. Solid CsCl was added to give a final concentration of 800 μg/mL plus EtBr was added to give a final concentration of 1 mg/mL. The resulting solution was spun in a Vti 50 rotor at 49,000 RPM for 18–20 hours at 20° C.

The plasmid band was visualized by UV fluorescence and drawn from the tube using a needle and syringe. The plasmid solution was n-butanol extracted four times and ethanol precipitated at −20° C. The ethanol precipitation was repeated at least twice to remove all of the CsCl. The plasmid was stored at −20° C. as an ethanol precipitate.

EXAMPLE VII

Purification of Alcohol Oxidase

Protein samples from *Pichia pastoris* cells grown on methanol as described in Example I were prepared by lysis of yeast cells, followed by a clearing spin to remove cell debris, as follows: A portion of the fermenter effluent was removed and adjusted to pH 7.5 with ammonion hydroxide, and was homogenzied on a Dyno-Mill Model KDL using a 0.6 liter vessel in a continuous operation at 30° C. using belt combination #3 and a flow of 20–30 mL/hr. The beads in the mill were lead free glass beads with a diameter of 0.3–0.5 mm. The resulting homogenate was centrifuged at 5° C. and 20,000Xg for 30 minutes to yield a cell-free supernatant.

Six 130 mL portions of the cell-free supernatant were placed in cellulose acetate dialysis bags and dialyzed at 5° C. against about 8 liters of distilled water. After 4 days, the aqueous phase of each bag is decanted. The solids remaining in the bags consisted of two types of solid. The thin upper white layer was carefully removed and discarded. The bottom solid was brown-yellow and was crystalline alcohol oxidase. The portion of the crystalline alcohol oxidase was dissolved in distilled water (about 10 times the volume of the solid) and an assay by the dye-peroxidase method showed an activity of 94 EU/mL The specific activity of the alcohol oxidase was 10.4 EU/mg of protein.

The crystalline precipitate resulting from the above-described dialysis was dialyzed against 0.05 M potassium phosphate buffer (pH 7.5), and applied to a 2x 200 cm Sepachryl 200 (Pharmacia) column equilibrated with the same buffer. Fractions of 3.5 mL were collected at a flow rate of 10 mL/hr and assayed for alcohol oxidase activity.

The alcohol oxidase activity for reaction with methanol was determined by the following assay procedure (dye-peroxidase method). A dye-buffer mixture was prepared by mixing 0.1 mL of an o-dianisidine solution (1 weight % o-dianisidine in water) with 12 mL of aerated 0.1 M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity (μ mole/min/mL or Enzyme Units/mL)} = \frac{\Delta A}{\min} \times 11.5$$

wherein 11.5 is a factor based on a standard curve prepared with known aliquots of H$_2$O$_2$ and ΔA is the change in absorbance during the experimental interval.

A total of 0.1 μg of total protein from each fraction was also assayed for alcohol oxidase content by gel electrophoresis with SDS-polyacrylamide (12%).

EXAMPLE VIII

DNA and Protein Sequencing

Determination of DNA sequences was performed by the dideoxy chain elongation method using bacteriophage M13 (Sanger et al, 1980) or by the chemical modification method (Maxam and Gilbert, 1980). The DNA fragments corresponding to the 5' end of the alcohol oxidase gene were inserted into the M13mp8 and M13mp9 vectors or end-labelled for the chemical modification method using restriction enzyme sites available in this region.

The 710bp HindIII/SalI fragment from pPG 4.0 was end-labelled for Maxam-Gilbert sequencing by first digesting 33 μg of the plasmid with HindIII. The reaction mixture was phenol/chloroform/isoamyl alcohol extracted, chloroform/isoamyl alcohol extracted and ethanol precipitated. The DNA was collected by centrifugation and resuspended in 31 μL of water. 100 μCi of $^{32}$P-α-dCTP (3200 Ci/mmol) and 2 units of Klenow fragment DNA PolI was added to the reaction mixture to give a final volume of 50 μL containing 400 μM dATP, 400 μM dGTP, 50 mM Tris, (pH 7.4), 10 mM MgSO$_4$, and 1 mM DTT. The reaction mixture was incubated at 37° C. for 1 hour and stopped by the addition of 2 μL of 0.5 M EDTA. The mixture was then phenol/chloroform/isoamyl alcohol extracted, chloroform/isoamyl alcohol extracted, chromatographed on a Sephadex G-50 column, and the labelled nucleic acid fractions pooled and ethanol precipitated. After centrifugation, the DNA pellet was resuspended in water and digested with SalI. The digest was electrophoresed on a 1% agarose gel in TAE buffer, and the 710 bp band was cut from the gel, the DNA electroeluted, butanol extracted, and ethanol precipitated. The fragment was resuspended in 100 μL of TE buffer, adjusted to 2.5 M ammonium acetate and then ethanol precipitated. The resulting DNA fragment was resuspended in TE buffer at a concentration of 50,000 cpm/μL.

The four base modification reactions were performed as follows: (a) the G (guanine) reaction was incubated for 8 minutes at 22° C. and contained 1 μL (50,000 CPM) of the labelled DNA fragment, 4 μL of water, 200 μL of 50 mM sodium cacodylate, pH 8.0, 1 mM EDTA (DMS buffer) and 1 μL dimethyl sulfate. The reaction was terminated by the addition of 50 μL of DMS stop buffer containing 1.5 M sodium acetate, (pH 7.0), 1 M 2-mercaptoethanol and 100 μg/mL tRNA, then ethanol (750 μL) was added and the reaction mixture was held at −70° C. for at least 15 minutes. (b) the G/A (guanine/adenine) reaction was incubated for 10 minutes at 22° C. and contained 2 μL (100,000 cpm) of the labelled DNA fragment, 8 μL of water and 30 μL of formic acid. The reaction was terminated by the addition of 200 μL of Hz stop buffer (0.3 M sodium acetate, pH 5.5, 0.1 M EDTA and 25 μg/mL tRNA), then ethanol (750 μL) was added and the reaction mixture held at −70° C. for at least 15 minutes. (c) the T/C (thymine/cystosine) reaction was incubated for 10 minutes at 22° C. and contained 2 μL (100,000 cpm) of the labelled DNA fragment, 18 μL of water and 30 μL of hydrazine. The reaction was terminated as described in (b) above. (d) the C (cytosine) reaction was incubated for 10 minutes at 22° C. and contained 1 μL (50,000 cpm) of the labelled DNA fragment, 4 μL of water, 15 μL of 5 M NaCl, and 30 μL of hydrazine. The reaction was terminated as described in (b) above.

The DNA pellets were collected by centrifugation, resuspended in 250 μL of 0.3 M sodium acetate, pH 5.5 and ethanol precipitated with 750 μL of 95% ethanol. The pellets were collected by centrifugation, dried under vacuum for 5 minutes, and the DNA cleaved by resuspending the pellets in 100 μL of a 1 to 10 (v/v) dilution of piperdine. The cleavage reaction was incubated at 90° C. for 30 minutes and terminated by the addition of 500 μL of 98% ethanol, 60 mM sodium acetate (pH 5.5) and 10 μg/mL tRNA. The reaction mixture was placed in a dry-ice/ethanol bath (about −70° C.) for about 5 minutes and the DNA fragments were collected by centrifugation. The fragments were resuspended in 50 μL of 0.3 M sodium acetate (pH 5.5) and then ethanol precipitated with 100 μL of 95% ethanol. This ethanol precipitation was repeated, the pellets were washed with 95% ethanol and evaporated under vacuum during centrifugation. The pellet was resuspended in 10 μL of 80% formamide, 10 mM NaOH, 1 mM EDTA, 0.1% xylene cyanol and 0.1% bromphenol blue. Two to three μL were electrophoresed on a 10 % 0.4 mm thick polyacrylamide gel in TBE buffer.

The amino acid sequence of alcohol oxidase was determined by Sequemat, Inc. (Watertown, Mass.) using 2 mg of purified alcohol oxidase from *Pichia pastoris*. The first 18 amino acids of the mature protein were determined to be;

Ala—Ile—Pro—Glu—Glu—Phe—Asp—Ile—Leu—
—Val—Leu—Gly—Gly—Gly—Ser—Gly—Ser.

EXAMPLE IX

Determination of Alcohol Oxidase Transcriptional Initiation Site

To determine where the start of the mRNA for alcohol oxidase was located, a primer extension experiment was performed using a synthetic oligonucleotide copies from the DNA sequences of the 5' end of the alcohol oxidase gene as primer and 10 μg of poly A+ *Pichia pastoris* mRNA as template. Ten μg of *Pichia pastoris* poly A+ mRNA was combined with 3 ng. of primer (5'-CTT CTC AAG TTG TCG-3') in a final volume of 9.3 μL which was 43 mM NaCl, 29.2 mM Tris (pH 8.3), 5.2 mM MgCl$_2$ and 4.3 mM DTT. The nucleic acids were denatured at 70° C. for 5 minutes and reannealled by allowing to slowly cool to 22° C. The reannealling mix was added to a tube containing 4 μL of dNTP mix 0.8 μL RT buffer, and 1 μL $^{32}$P-α-dCTP (800 Ci/mmol). Three μL of this mixture was added to 1 μL of each respective ddNTP. The final 3 μL in the mixture was added to 1 μL of water. The reactions were started by the addition of 1 μL of dil RT and incubated at 42° C. for 15 minutes. The reactions were chased with 3 μL of Chase RT at 42° C. for 15 minutes. The reactions were stopped by the addition of 7.5 μL formamide dye mix and 4–5 μL were electrophoresed on a 0.4 mm thick gradient gel in 1x TBE. After electrophoresis the gel was fixed in 10% acetic acid with 10% methanol for 20 minutes. The gel was dried under vacuum and used to expose an XAR x-ray film.

The gradient gel was prepared as follows: 300 μL of 10% ammonium persulphate and 14 μL of TEMED were added to 30 mL of top gel; 75 μL of 10% ammonium persulfate and 3.5 μL TEMED were added to 7 mL of bottom gel, 6 mL of top gel were drawn up into a pipet and then 6 mL of bottom gel were drawn into the same pipet. The gel was poured between the gel plates followed by 22 mL of top gel.

EXAMPLE X mRNA Hybridization-Selection And In Vitro Translations

Positive hybridization-translation experiments were performed by linearizing twenty μg of cloned Pichia genomic DNA (prepared as described in Example VI) by digestion with various restriction endonucleases. This DNA was denatured by making the solution 0.3 M NaOH and incubating at 65° C. for 10 minutes. The denatured DNA-containing solution was quickly chilled on ice and neutralized by adjusting to 0.5 M Tris•HCl (pH 7.4). An equal volume of 20x SSPE was added to the denatured DNA immediately prior to binding the DNA to the nitrocellulose filters. Prior to applying the DNA to the nitrocellulose filters (Schleicher and Schuell BA83, 9 mm dia.), the filters were prepared by wetting with H₂O, boiling for 10 minutes and rinsing three times in 10x SSPE. Ten µg of DNA was then bound to each filter by applying the DNA to the filter, air drying and finally drying the filters under vacuum at 70° C. for 2 hours.

Prior to prehybridization, the filters with the bound DNA were placed in 1 mL of sterile water and heated for one minute at 100° C., cooled on ice, rinsed by vortexing in 1 mL of sterile water and rinsed with 1 mL of prehybridization buffer. The filters were prehybridized in 1 mL of prehybridization buffer, then 40 µg (2µg/mL ETC) of poly A+ mRNA was added directly to the prehybridization buffer. The hybridization mixture was heated at 65° C. for 10 minutes and then incubated at 42° C. for 24 hours.

Following the hydridization, filters were washed briefly 2 times 1x SSPE which contained 0.5% SDS at 22° C., 7 times in 1x SSPE which contained 0.5% SDS at 50° C. for 5 minutes each, 3 times in 0.1x SSPE at 50° C. for 5 minutes each, and once in 0.1x SSPE at 65° C. for 10 minutes. The RNA was eluted from the filters by boiling for 1 minute in 300 µL of H₂O containing 15 µg of rabbit liver tRNA. The eluted RNA was quickly frozen in a dry-ice ethanol bath. The RNA mixture was allowed to warm to room temperature and the filters removed. The RNA mixture was then precipitated by adjusting the medium to 2.5 M ammonium acetate and precipitating with ethanol 2 times, and finally resuspended in 100 µL of H₂O before being lyophilized.

Translations were performed according to standard techniques known by those of skill in the art, such as for example, instructions provided by New England Nuclear in vitro rabbit reticulocyte lysate translation kits. Protein products were electrophoresed on 8% polyacrylamide gels containing a 4.5% stacking gel.

EXAMPLE XI

Antisera Preparations and Immunoprecipitations

Antisera raised in rabbits against an extract from *Pichia pastoris* cells containing both p72 (alcohol oxidase) and p76 polypeptides were prepared using standard protocols. Extracts were dialyzed against PBS before injections. Over a course of 8 weeks, each rabbit received 3 injections each of which consisted of 1 mg of total protein in a volume of 0.1 mL with 0.2 mL of Freunds complete adjuvant. Injections were intradermally delivered to 6-10 sites in the rabbit. At the end of eight weeks, the rabbits were bled, and their sera tested against purified *Pichia pastoris* alcohol oxidase by the Ouchterlony double diffusion procedure.

Purified rabbit anti-p72 (alcohol oxidase) and anti-p76 protein antibodies were prepared by affinity chromatography of whole antisera through a CNBr coupled p72 (alcohol oxidase)-p76 Sepharose 4B column (Pharmacia). One gram of CNBr activated gel was prepared by hydrating the gel for 15 minutes in 200 mL of 1 mM HCl followed by 3x 50 mL washes in coupling buffer (0.1 M sodium carbonate (pH 8) and 0.5 M NaCl). Five mL of a 6 mg/mL solution of p72-p76 in coupling buffer was added to the gel and gently agitated overnight at 4° C. Unbound protein was removed by washing 3x 50 mL with coupling buffer. The remaining active groups were eliminated by a 2-hour incubation in 1 M ethanolamine (pH 8). Non-covalently bound material was removed from the gel by a 50 mL wash with 2 M sodium thiocyanate in PBS. Prior to chromatography of the antisera, the gel was finally washed with 3x 50 mL of PBS. Five mL of clarified anti p72-p76 antisera were mixed with the gel and incubated with gentle agitation for 2 hours at 4° C. The antisera-gel mixture was then pipetted into a 1x 8 cm column and washed with 150 mL of PBS. Purified antibody was eluted from the column with 6 mL of 2 M sodium thiocynate in PBS. After elution from the gel, the purified antibody was dialyzed extensively against PBS which contained 0.02% sodium azide.

The affinity-purified antisera was added to an in vitro translation mix in PBS, 1% NP40 and incubated overnight at 4° C. The antibody-antigen complex was precipitated with Pansorbin (Calbiochem) on ice for 2.5 hours. Pansorbin was prepared by washing in RIPA buffer. Pansorbin precipitates were washed 4 times in RIPA buffer and dissolved in Laemmli loading buffer before electrophoresis.

EXAMPLE XII

*Pichia pastoris* Transformation Procedure

A. Cell Growth

1. Inoculate a colony of *Pichia pastoris* GS115 (NRRL Y-15851) into about 10 mL of YPD medium and shake culture at 30° C. for 12-20 hrs.
2. After about 12-20 hrs., dilute cells to an OD$_{600}$ of about 0.01-0.1 and maintain cells in log growth phase in YPD medium at 30° C. for about 6-8 hrs.
3. After about 6-8 hrs, inoculate 100 mL of YPD medium with 0.5 mL of the seed culture at an OD$_{600}$ of about 0.1 (or equivalent amount). Shake at 30° C. for abour 12-20 hrs.
4. Harvest culture when OD$_{600}$ is about 0.2-0.3 (after approximately 16-20 hrs) by centrifugation at 1500 g for 5 minutes.

B. Preparation of Spheroplasts

1. Wash cells once in 10 mL of sterile water. (All centrifugations for steps 1-5 are at 1500 g for 5 minutes.)
2. Wash cells once in 10 mL of freshly prepared SED.
3. Wash cells twice in 10 mL of sterile 1 M Sorbitol
4. Resuspend cells in 10 mL SCE buffer.
5. Add 5-10 µL of 4 mg/mL Zymolyase 60,000 (Miles Laboratories). Incubate cells at 30° C. for about 30-60 minutes.

Since the preparation of spheroplasts is a critical step in the transformation procedure, one should monitor spheroplast formation as follows: add 100 µL aliquots of cells to 900 µL of 5% SDS and 900 µL of 1 M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1 M Sorbitol by centrifugation at 1000 g for 5-10 minutes. (The time and speed for centrifugation may vary; centrifuge enough to pellet spheroplasts but not so much that they rupture from the force.)
7. Wash cells once in 10 mL of sterile CaS.
8. Resuspend cells in total of 0.6 mL of CaS.

C. Transformation

1. Add DNA samples (up to 20 µL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)
2. Add 100 μL of spheroplasts to each DNA sample and incubate at room temperature for about 20 minutes.
3. Add 1 mL of PEG solution to each sample and incubate at room temperature for about 15 minutes.
4. Centrifuge samples at 1000 g for 5-10 minutes and decant PEG solution.
5. Resuspend samples in 150 μL of SOS and incubate for 30 minutes at room temperature.
6. Add 850 μL of sterile 1 M Sorbitol and plate aliquots of samples as described below.

D. Regeneration of Spheroplasts
1. Recipe for Regeneration Agar Medium;
   a. Agar-Sorbitol- 9 g Bacto-agar, 54.6 g Sorbitol, 240 mL H$_2$O, autoclave.
   b. 10X Glucose- 20 g Dextrose, 100 mL H$_2$O, autoclave.
   c. 10X SC- 6.75 g Yeast Nitrogen Base without amino acids, 100 mL H$_2$O, autoclave, (Add any desired amino acid or nucleic acid up to a concentration of 200 μg/mL before or after autoclaving.)
   d. Add 30 mL of 10X Glucose and 30 mL of 10X SC to 240 mL of the melted Agar-Sorbitol solution. Add 0.6 mL of 0.2 mg/mL biotin and any other desired amino acid or nucleic acid to a concentration of 20 μg/mL. Hold melted Regeneration Agar at 55°-60° C.
2. Plating of Transformation Samples:
   Pour bottom agar layer of 10 mL Regeneration Agar per plate at least 30 minutes before transformation samples are ready. Distribute 10 mL aliquots of Regeneration Agar to tubes in a 45°-50° C. bath during the period that transformation samples are in SOS. Add aliquots of transformation samples described above to tubes with Regeneration Agar and pour onto bottom agar layer of plates. Add a quantity of each sample to 10 mL aliquots of melted Regeneration Agar held at 45°-50° C. and pour each onto plates containing a solid 10 mL bottom agar layer of Regenation Agar.
3. Determination of Quality of Spheroplast Preparation:
   Remove 10 μL of one sample and dilute 100 times by addition to 990 μL of 1 M Sorbitol. Remove 10 μL of the 100 fold dilution and dilute an additional 100 times by addition to a second 990 μL aliquot of 1 M Sorbitol. Spread plate 100 μL of both dilutions of YPD agar medium to determine the concentration of unspheroplasted whole cells remaining in the preparation. Add 100 μL of each dilution to 10 mL of Regeneration Agar supplemented with 40 μg/mL histidine to determine total regeneratable spheroplasts. Good values for a transformation experiment are $1-3 \times 10^7$ total regeneratable spheroplasts/mL and about $1 \times 10^3$ whole cells/mL.
4. Incubate plates at 30° C. for 3-5 days.

EXAMPLE XIII

Isolation of *Pichia Pastoris* HIS4 Gene And Autonomous Replication Sequences

A. Strains
The strains employed include:
(a) *Pichia pastoris* strain NRRL Y-11430;
(b) *Pichia pastoris* GS115 (his4; NRRL Y-15851);
(c) *S. cerevisiae* strain 5799-4D (a his4-260 his4-39; NRRL Y-15859); and
(d) *E. coli* strain 848 (F$^-$ met thi gal T$_1^R$ φ80$^S$ hsdR$^-$ hsdM$^+$).

Figure 23:
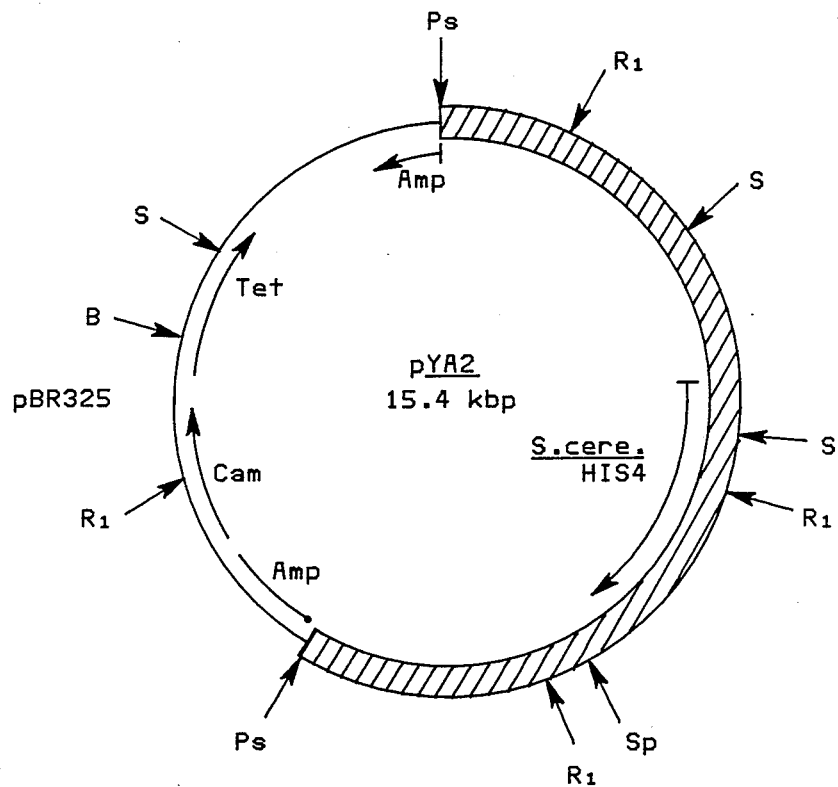
FIG. 23 is a restriction map of plasmid pYA2.
Figure 24:
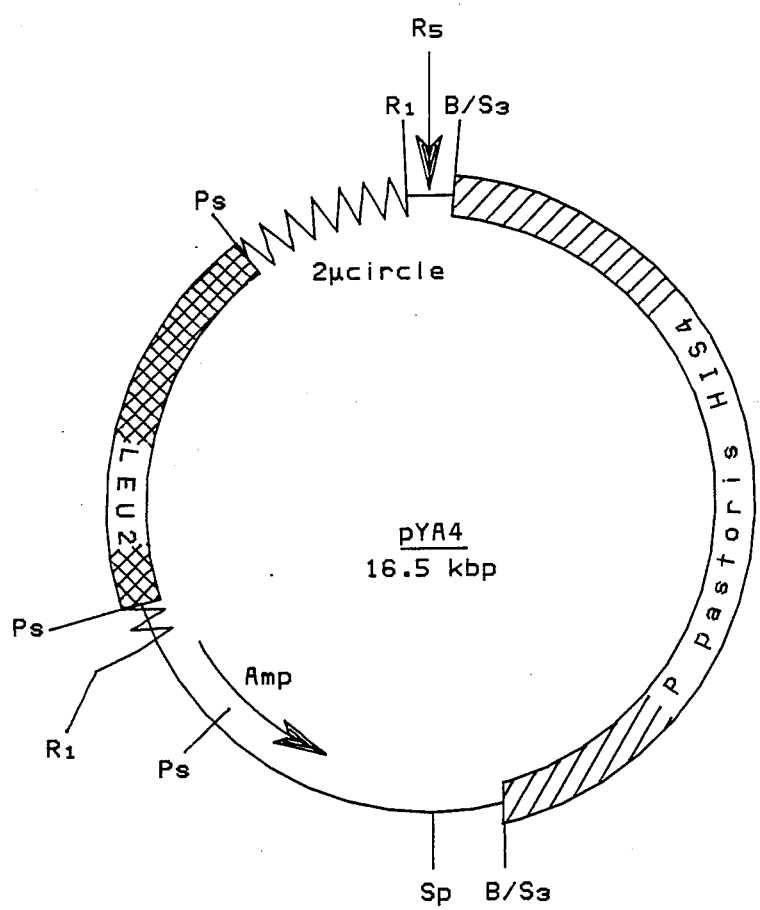
FIG. 24 is a restriction map of plasmid pYA4.

B. Plasmids
pYA2 (see FIG. 23; consists of the *S. cerevisiae* HIS4 gene on a 9.3 kbp PstI fragment inserted at the PstI site of pBR325) was the source of the *S. cerevisiae* HIS4 gene fragments and has been deposited in an *E. coli* host and is available to the public as NRRL B-15874.
YEp13 is available from the American Type Culture Collection and has been assigned accession number ATCC 37115.

C. Media
*Pichia pastoris* has grown in YPD (rich) or IMG (minimal) media. IMG, a minimal medium, consists of the following:
1. IM$_1$ Salts at a final concentration of 36.7 mM KH$_2$PO$_4$, 22.7 mM (NH$_4$)$_2$SO$_4$, 2.0 mM MgSO$_4$·7H$_2$O, 6.7 mM KCl, 0.7 mM CaCl$_2$·2H$_2$O, prepared as a 10x stock solution and autoclaved;
2. Trace Salts at a final concentration of 0.2 μM CuSO$_4$·5H$_2$O, 1.25 μM KI, 4.5 μM MnSO$_4$·H$_2$O, 2.0 μM NaMoO$_4$·2H$_2$O, 0.75 μM H$_3$BO$_3$, 17.5 μM ZnSO$_4$·7H$_2$O, 44.5 μM FeCl$_3$·6H$_2$O, prepared as a 400x stock solution and filter sterilized;
3. 0.4 μg/mL biotin; and
4. 2% dextrose.

*E. coli* was cultured in either LB medium or 2B medium (0.2% NH$_4$PO$_4$, 1.2% Na$_2$HPO$_4$, 0.013% MgSO$_4$·7H$_2$O, 0.074% CaCl$_2$·2H$_2$O, 1 μg/mL thiamine and 0.4% dextrose) supplemented with 100 μg/mL tryptophan, and 0.2% Casamino acids.

D. DNA Isolation
1. Large Scale Preparations of Yeast DNA
Both *Pichia pastoris* and *S. cerevisiae* DNA preparations were carried out by growing yeast cells in 100 mL of minimal medium until A$_{600}$ equals 1-2 and then harvesting the cells by centrifugation at 2,000 g for 5 minutes. The cells were washed once in H$_2$O, once in SED, once in 1 M sorbitol and then suspended in 5 mL of 0.1 M Tris-HCl (pH 7.0) which is 1 M in sorbitol. The cells were mixed with 50-100 μL of a 4 mg/mL solution of Zymolase 60,000 (Miles Laboratories) and incubated at 30° C. for 1 hour to digest the cell walls. The spheroplast preparation was then centrifuged at 1000 g for 5-10 minutes and suspended in Lysis buffer (0.1% SDS, 10 mM Tris-HCl, (pH 7.4), 5 mM EDTA and 50 mM NaCl). Proteinase K (Boeringer Mannheim) and RNase A (Sigma) were each added to 100 μg/mL and the mixtures incubated at 37° C. for 30 minutes. DNA was deproteinized by gently mixing the preparation with an equal volume of chloroform containing isoamyl alcohol (24:1, v/v) and the phases were separated by centrifugation at 12,000 g for 20 minutes. The upper (aqueous) phase was drawn off into a fresh tube and extracted with an equal volume of phenol/chloroform/isoamyl alcohol. The phases were separated as before and the top phase placed in a tube containing 2-3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

2. Small Scale Yeast DNA Preparations
Five mL of yeast cultures in minimal medium were grown until A$_{600}$ equals 1-5 and harvested by centrifugation at 2,000 g for 5 minutes. Cells were suspended in 1 mL of SED and transferred to a 1.5 mL microfuge tube, washed once in 1 M sorbitol and resuspended in 0.5 mL of 0.1 M Tris-HCl (pH 7.4) which is 1 M sorbitol Zymolyase 60,000 (10 μL of a 4 mg/mL solution) was added and the cells were incubated for 30–60 minutes at 30° C. Cells were then centrifuged for 1 minute, suspended in the Lysis buffer and incubated at 65°–70° C. After 15 minutes the samples were mixed with 100 μL of 5 M potassium acetate, held in an ice bath for 5 minutes and centrifuged for 5 minutes. The supernatants were decanted into a fresh microfuge tube containing 1 mL of 100% ethanol, mixed and centrifuged for 10 seconds. Finally, the DNA pellets were air dried for 10–15 minutes and dissolved in 50 μL of TE buffer.

3. Large Scale *E. coli* DNA Isolations

E. coli cultures for large scale (0.5–1 L) plasmid preparations were grown at 37° C. with shaking in 2B medium supplemented as described above and with the appropriate antibiotic. For cells which contained pBR322 derived plasmids, cultures were grown to an $A_{550}$ of about 0.7 at which time sufficient chloramphenicol was added to give a concentration of 100 μg/mL and cells harvested approximately 15 hours later. Strains which contained pBR325 derived plasmids were inoculated into the supplemented 2B medium at a starting $A_{550}$ of about 0.01–0.05 and incubated with shaking at 37° C. for 20–24 hours before harvesting.

4. Small Scale *E. coli* DNA Preparations

For small scale rapid plasmid isolations, 2 mL cultures in the supplemented 2B medium with antibiotic were grown overnight at 37° C. with shaking and harvested by centrifugation in 1.5 mL microfuge tubes. Plasmids from all preparations were isolated by the alkaline lysis method described by Birnboim and Doly (1979).

E. Restriction DNA and Fragment Isolation

Restriction enzymes were obtained from New England Biolabs and Bethesda Research Laboratories and digestions were performed by routine techniques. Restriction mappings were carried out by comparing parallel digestions of plasmids with and without insert DNA. Restriction fragments were purified by electroelution from agarose gels into Whatman 3 MM paper strips backed by dialysis tubing. The fragments were recovered from the paper and tubing by 3–4 washings with 0.1–0.2 mL volumes of a solution which contained 0.1 M NaCl, 50 mM Tris-HCl (pH 8.0) and 1 mM EDTA. Finally, the fragments were extracted with phenol/chloroform/isoamyl alcohol, precipitated with ethanol and redissolved in a small volume of TE buffer.

F. *P. pastoris* Library Construction in *E. Coli*

For the *Pichia pastoris* DNA-YEp13 library construction, 100 μg of YEp13 was digested to completion with BamHI and treated with calf intestinal alkaline phosphatase to remove the terminal 5′ phosphate from the DNA. A 100 μg aliquot of wild type *Pichia pastoris* DNA from *Pichia pastoris* NRRL Y-11430) was partially digested with 10 units of Sau3A I by incubation for 5 minutes at 37° C. in a total volume of 1 mL. Fragments of 5 to 10 kb were size selected by centrifugation through 5–20% sucrose gradients. One μg of the vector and 2 μg of the Pichia Sau3A I fragments were mixed with 20 units of T4 DNA ligase (Bethesda Research Laboratories) in a total volume of 200 μL and incubated overnight at 4° C. The ligated DNAs were transformed into *E. coli* by adding the entire ligation reaction mix to 2 mL of competent *E. coli* 848 cells and incubating at 0° C. The mixture was warmed to 37° C. for 5 minutes after which time 40 mL of LB medium was added and the 37° C. incubation continued for another 1 hour. Ampicillin was then added to give a total concentration of 100 μg/mL and the incubation continued for a second hour. Finally, the cells were centrifuged for 10 minutes at 3,000 g, resuspended in 1 mL of fresh LB medium and spread in equal aliquots on 10 LB agar plates containing 100 μg/mL of ampicillin. The approximately 50,000 colonies which resulted were scraped from the plates and a portion of the cells was inoculated into 500 mL of the supplemented 2B medium at a starting $A_{550}$ of about 0.1. The culture was grown and plasmid was extracted as described above. Of the colonies which were pooled for the library, 96 out of 100 tested were tetracycline sensitive and 7 out of 10 examined contained plasmids with insert DNA.

For the *Pichia pastoris* DNA-pYJ8ΔCla library construction, 50 μg of pYJ8ΔCla was digested to completion with ClaI and treated with calf intestinal alkaline phosphatase to remove the terminal 5′ phosphate from the DNA. A 100 μg aliquot of DNA from *Pichia pastoris* NRRL Y-15851 was partially digested with 20 units of TaqI by incubation for 5 minutes at 65° C. in a total volume of 1 mL. Fragments of 5 to 10 kbp were size selected by electroelution from a 0.5% agarose gel (See Example II, Section E). One μg of the vector and 2 μg of the Pichia TaqI fragments were mixed with 20 units of T4 DNA ligase (Bethesda Research Laboratories) in a total volume of 200 μL and incubated overnight at 4° C. The ligated DNAs were transformed into *E. coli* by adding the entire ligation reaction mix to 2 mL of competent *E. coli* 848 cells and incubating for 15 minutes at 0° C. The mixture was warmed to 37° C. for 5 minutes after which time 40 mL of LB medium was added and the 37° C. incubation continued for another 1 hour. Ampicillin was then added to give a total concentration of 100 μg/mL and the incubation continued for a second hour. Finally, the cells were centrifuged for 10 minutes at 3,000 g, resuspended in 1 mL of fresh LB medium and spread in equal aliquots on 10 LB agar plates containing 100 μg/mL of ampicillin. The approximately 10,000 colonies which resulted were scraped from the plates and a portion of the cells was inoculated into 500 mL of the supplemented 2B medium at a starting $A_{550}$ of about 0.1. The culture was grown and plasmid was extracted as described above.

G. Southern Hybridizations

For transfer of large or supercoiled DNA molecules to nitrocellulose, DNA was first partially hydrolyzed by soaking agarose gels in 0.25 M HCl for 10 minutes prior to alkali denaturation. The hybridization of labelled fragments from the *S. cerevisiae* HIS4 gene to *Pichia pastoris* DNA was performed in the presence of 50% formamide, 6x SSC, 5x Denhardt's, 0.1% SDS, 1 mM EDTA, and 100 μg/mL denatured herring sperm DNA at 42° C. Post-hybridization washes were in 1x SSC, 1 mM EDTA, 0.1% SDS and 1.0% sodium pyrophosphate at 65° C. DNA was $^{32}$P-labelled as described in Example IV.

H. DNA Sequencing

DNA sequencing was by the dideoxynucleotide chain termination method of Sanger et al (1980).

I. Yeast Transformations

*S. cerevisiae* transformations were carried out by the spheroplast generation method of Hinnen et al (1978).

*Pichia pastoris* transformations were performed following the procedure described above.

J. Analysis of *Pichia pastoris* Transformants

The ability of each plasmid to be maintained as an autonomous element in *Pichia pastoris* cells was determined as follows: A transformant colony was picked from the regeneration agar plate and streaked onto an SD medium agar plate and inoculated into liquid IMG medium. The SD plate was incubated at 30° C. for 3 days after which time a single colony was picked from this plate, streaked onto a second SD plate and inoculated into a second flask of IMG medium. This process was repeated a third time. The 3 IMG cultures were grown at 30° C. with shaking to an $A_{600}$ of about 1-2 and then harvested by centrifugation. DNA from the yeast cultures was extracted as described above, electrophoresed at 30 Volts and 30 mAmps for 10-15 hours into 0.8% agarose gels, transferred to nitrocellulose and hybridized to $^{32}$P-labelled pBR322 or pBR325 as described above. As controls, a sample containing 10 ng of plasmid isolated from E. coli and a sample containing 1-2 μg of untransformed Pichia pastoris GS115 DNA were electrophoresed in parallel with the experimental samples.

K. Isolation of Pichia DNA Sequences

DNA fragments which contained the Pichia HIS4 gene were isolated from a Pichia DNA library by their ability to complement S. cerevisiae his4 strains. The library was composed of 5-20 kb Sau3AI partial digestion fragments of wild type Pichia DNA inserted into the BamHI site of the S. cerevisiae-E. coli shuttle vector YEp13. Spheroplasts of S. cerevisiae NRRL Y-15859 (5799-4D; a his4ABC− strain) were generated by the technique of Hinnen et al (1978), mixed with the Pichia DNA library and allowed to regenerate in a medium deficient in histidine. The transformation resulted in about $1 \times 10^3$ prototrophic yeast colonies from a population of $5 \times 10^7$ total regeneratable spheroplasts. Total yeast DNA was extracted from 20 of the His+ colonies and transformed into E.coli. Seventeen of the yeast DNA preparations produced ampicillin resistant colonies and each contained plasmid comprised of YEp13 plus insert DNA. To confirm that the His+ transforming plasmids contained the Pichia HIS4 gene and not a DNA fragment with suppressor activity, restriction digests of the plasmids were hybridized to a labelled DNA fragment containing a large portion of the S. cerevisiae HIS4 gene and washed at low stringency. Each of the plasmids which complemented the his4 S. cerevisiae strains contained sequences which hybridized to the S. cerevisiae HIS4 gene.

To search for DNA fragments which contain Pichia ARS activity, DNA from Pichia pastoris GS115 (NRRL Y-15851) was partially digested with TaqI and 5 to 10 kbp fragments were isolated and cloned into the unique ClaI site of pYJ8ΔCla. (See FIG. 26). Plasmid DNA was recovered from about 10,000 His+ Pichia colonies and used to transform E. coli. Plasmids from about 10,000 ampicillin resistant colonies were isolated and then transformed back into GS115. Forty of the His+ yeast colonies from the sublibrary transformation were separately streaked onto selective medium and grown in separate cultures in selective medium. Total yeast DNA was extracted from each of these 40 cultures and transformed into E. coli. Two plasmids, pYA63 (PARS1) and pYA90 (PARS2) whose yeast DNA preparations produced the most ampicillin resistant E. coli colonies, were selected for further analysis. Both of these plasmids transformed Pichia pastoris GS115 (NRRL Y-15851) at a very high frequency and each contained an insert of foreign DNA.

EXAMPLE XIV

Construction Of Regulatory Region-lacZ Gene Fusions

A. p72 (Alcohol Oxidase) Regulatory Region Constructs

Plasmid pPG 4.0, a pBR322 vector which contains the 4 kilobase pair EcoRI-PvuII genomic DNA fragment from Pichia pastoris was cut with PstI, treated with S1 nuclease to produce blunt ends where cleavage occurred, then cut with BamHI to give a 1.12 kbp DNA fragment which contains the alcohol oxidase regulatory region and the coding information for the first 15 amino acids of alcohol oxidase. This 1.12 kbp DNA fragment has the following nucleotide sequence:

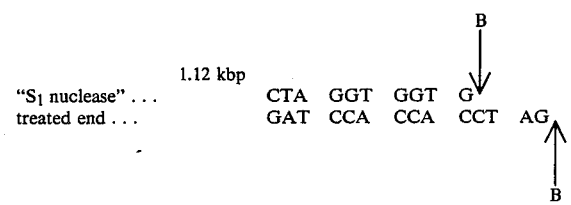

Figure 29:
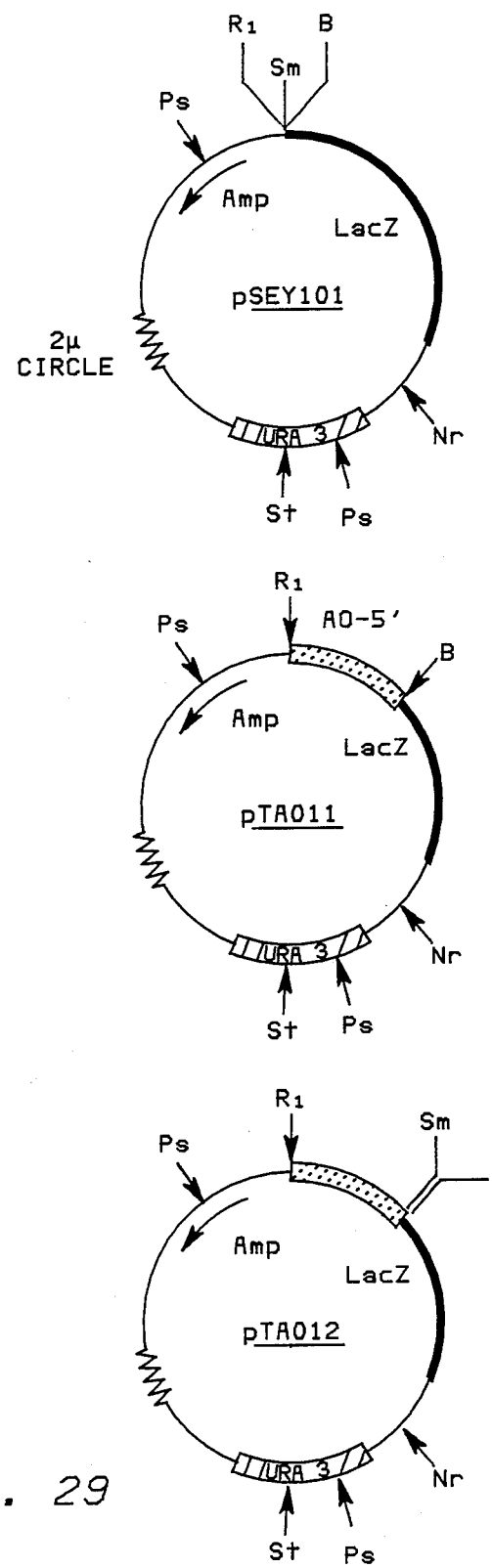
FIG. 29 provides a restriction map of plasmid pTAO 12 and shows how the plasmid was derived.

This 1.12 kbp was ligated into the EcoRI/SmaI/BamHI linker (cleaved with BamHI and SmaI) of the E. coli-S. cerevisiae shuttle vector pSEY101, Douglas et al (1984). Vector pSEY101 contains the E. coli lacZ gene and a polylinker with the following nucleotide sequence:

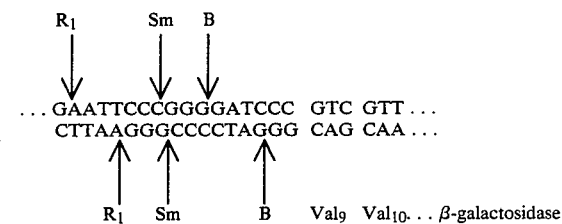

to give hybrid plasmid pTA011 (See FIG. 29).

Since the regulatory region-lacZ gene fusion of pTA011 is out of phase with respect to production of β-galactosidase as shown in Sequence E:

Sequence E

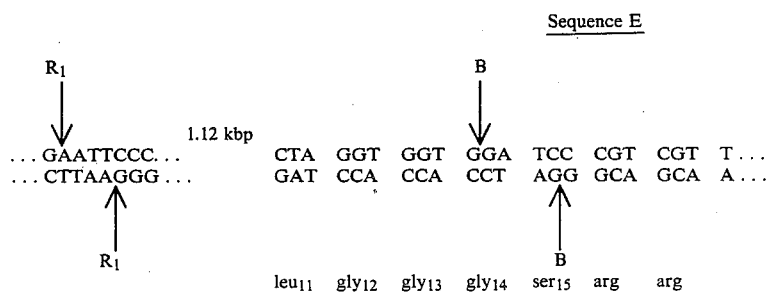

Vector pTA011 is cleaved at the unique BamHI site and the following SmaI linker inserted:

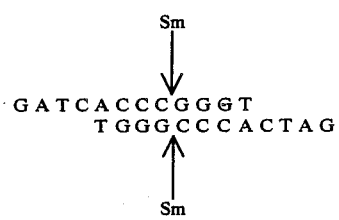

```
        Sm
        ↓
  GATCACCCGGGT
      TGGGCCCACTAG
              ↑
              Sm
``` thus producing hybrid vector pTA012, which has the following nucleotide sequence with respect to the regulatory region-lacZ fusion:

Sequence F

Figure 30:
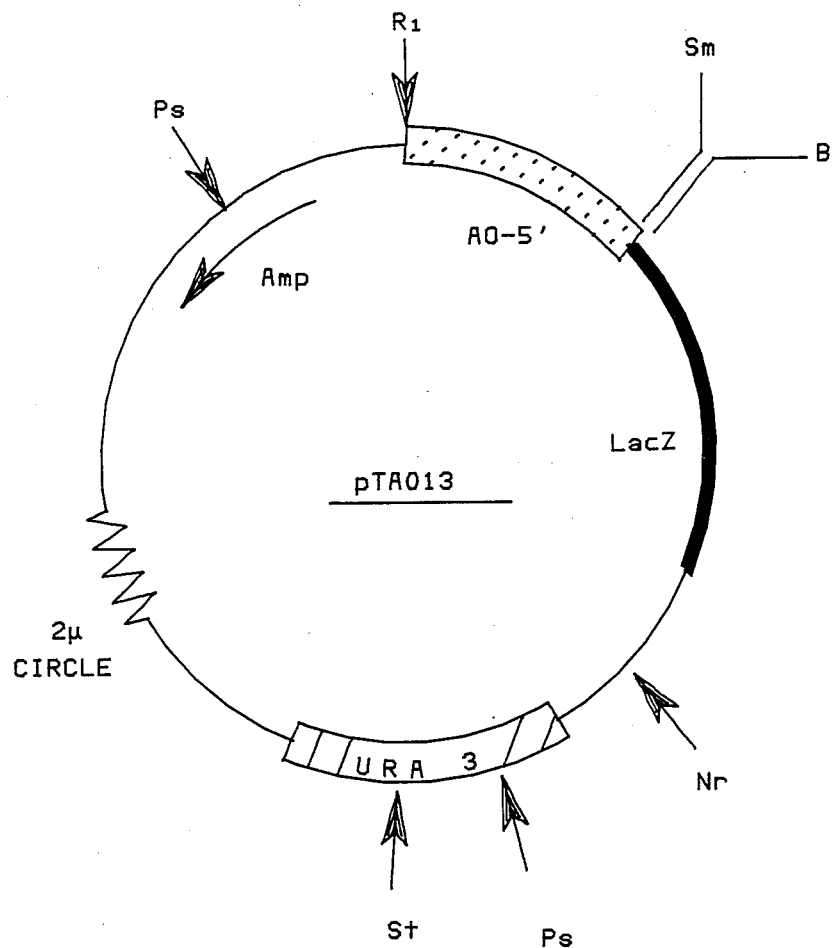
FIG. 30 is a restriction map of plasmid pTAO13.

```
R₁
↓       1.12 kbp                                        Sm
                                                        ↓
...GAATTCCC.......CTA GGT GGT GGA TCA CCC   GGG TGA TCC CGT CGT...
...CTTAAGGG.......GAT CCA CCA CCT AGT GGG   CCC ACT AGG GCA GCA...
↑                                           ↑
R₁                                          Sm
        leu₁₁ gly₁₂ gly₁₃ gly₁₄ ser₁₅ pro   stop ser arg arg
``` and thus, the regulatory region-lacZ fusion of pTA012 is still out of phase with respect to the LacZ reading frame. In order to bring the N-terminal coding information for the alcohol oxidase structural gene into an open reading frame with the structural lacZ gene, pTA012 was treated with EcoRI-SmaI and the resulting DNA fragment ligated into pSEY101 which had similarly been treated with EcoRI and SmaI thus producing hybrid vector pTA013 (See FIG. 30 and the nucleotide sequence below:

Regulatory region—lacZ gene fusions were prepared as follows with the p76 regulatory region.

1. Using the Entire 5' Portion of pPG 6.0

Figure 28:
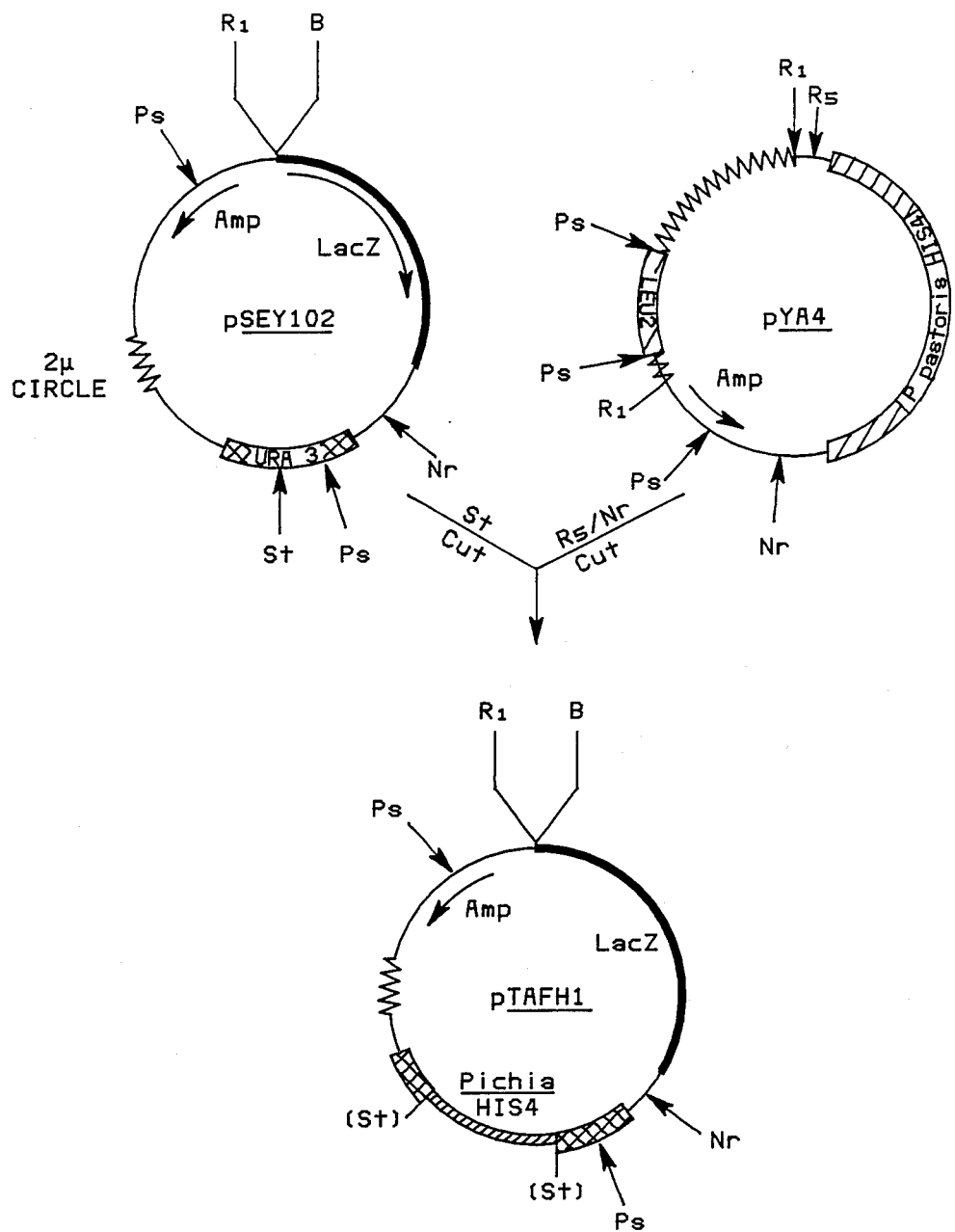
FIG. 28 provides a restriction map of plasmid pTAFH 1 and shows how the plasmid was derived.
Figure 30A:
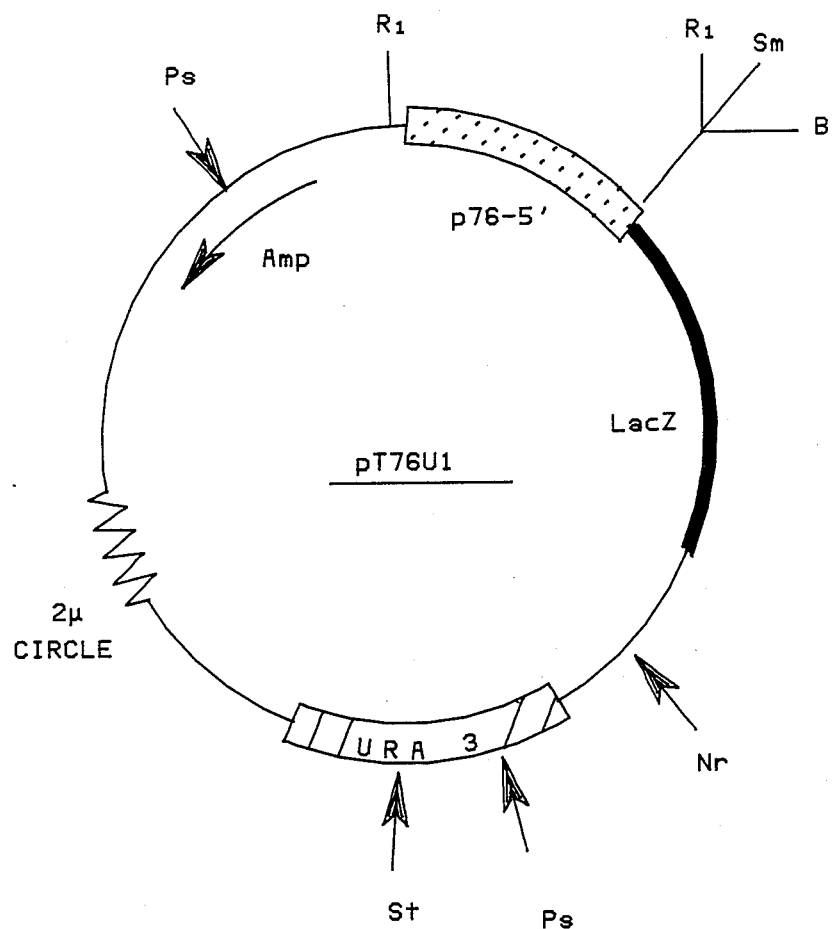
FIG. 30a is a restriction map of plasmid pT76U1.

The 1.35 Kb pair EcoRI fragment of pPG 6.0 was cloned into the unique EcoRI site of pSEY101, an *E. coli-S. cerevisiae* shuttle vector, giving plasmid pT76U1 (see FIG. 30a). Vector pT76U1 was then cleaved with PstI-NruI, and the larger DNA fragment ligated with the HIS4 gene-containing fragment of shuttle vector pTAFH1 (FIG. 28) as described above to give pT76H3; or with the EcoRI-end filled in PstI-EcoRI fragment of shuttle vector pBPf1 (see FIG. 34) to give pT76H4.

2. Using a Bal31 Digest of 5'-pPG 6.0

Figure 31:
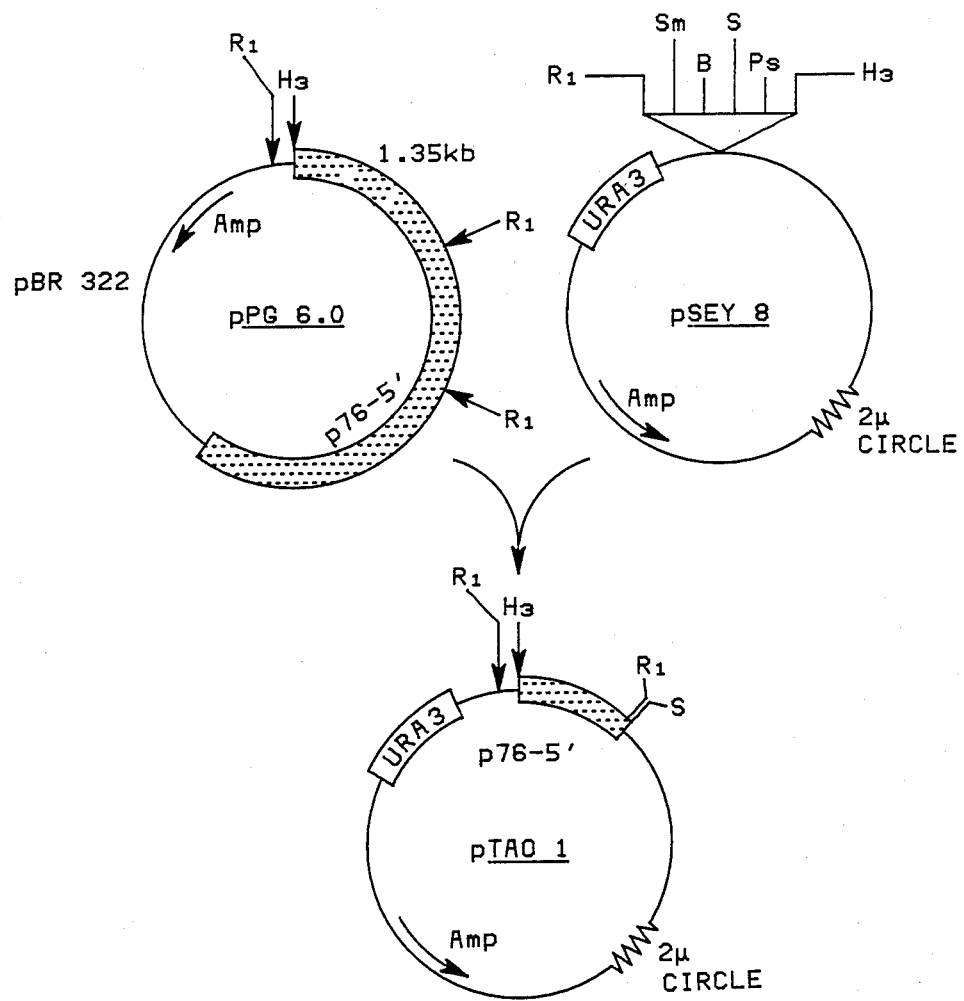
FIG. 31 provides a restriction map of plasmid pTAO1 and shows how the plasmid was derived.

A 1.35 kb pair EcoRI fragment of pPG 6.0 was cloned into the unique EcoRI site of pSEY8, an *E. coli-S.cerevisiae* shuttle vector, which also has a unique SalI site adjacent to the EcoRI site into which the Pichia DNA was inserted, thus giving plasmid pTA01 (See FIG. 31). The plasmid pTA01 was cleaved with SalI, treated with Bal31 exonuclease to produce blunt-ended fragments of polypeptide p76 regulatory region of various lengths. The blunt-ended fragments were freed from the remainder of plasmid pSEY8 by cleavage with EcoRI. The resulting DNA fragments were cloned into the EcoRI-SmaI linker of pSEY101 to give, Sequence G

```
R₁
↓       1.12 kbp                                  Sm      B
                                                  ↓       ↓
...GAATTCCC.......CTA GGT GGT GGA TCA CCC   GGG   GAT CCC GTC GTT...
...CTTAAGGG.......GAT CCC CCC CCT AGT GGG   CCC   CTA GGG CAG CAA...
↑                                           ↑         ↑
R₁                                          Sm        B
        leu₁₁ gly₁₂ gly₁₃ gly₁₄ ser₁₅ pro   gly  asp pro val₉ val₁₀...β-gal
```

The vector pTA013 was then used to transform *S. cerevisiae* SEY2102 for further studies described below in Example XV.

Vector pTA013 was then cleaved with PstI or PstI-NruI and the regulatory region-lacZ fusion contained in the cleaved fragment ligated with the HIS4 gene-containing fragment of shuttle vectors pTAFH1 (See FIG. 28), pYJ30 (See FIG. 27) or pYA2 (See FIG. 23) to give, respectively, plasmids pSAOH 1, pSAOH 5 and pSAOH 10.

| pTA013 plus | Resulting Plasmids |
|---|---|
| pTAFH1 | pSAOH1 |
| pYJ30 | pSAOH5 |
| pYA2 | pSAOH10 |

Figure 32:
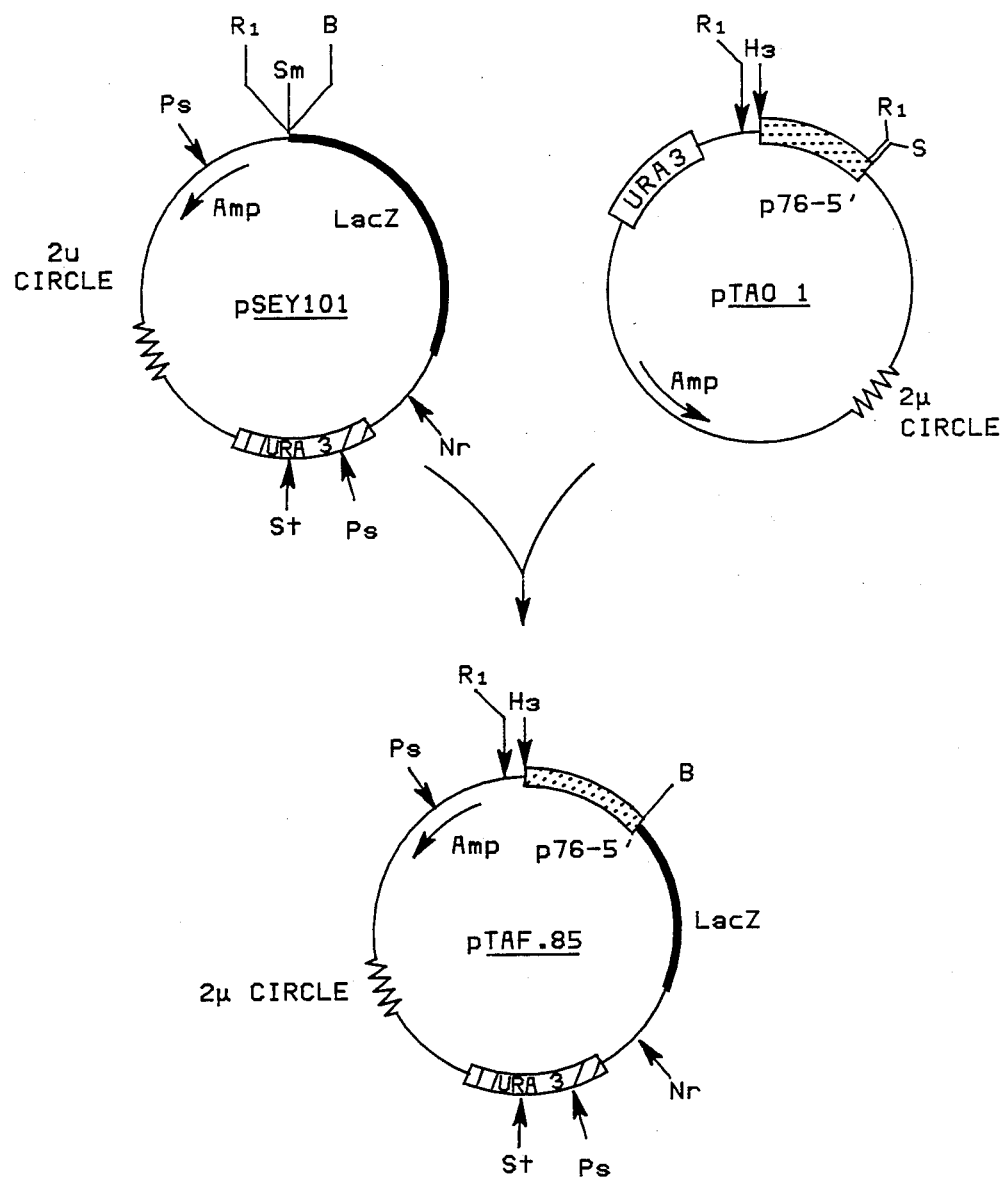
FIG. 32 provides a restriction map of plasmid pTAF.85 and shows how the plasmid was derived.

B. p76 Regulatory Region Constructs among others. plasmid pTAF.85 (see FIG. 32). Plasmid pTAF.85 is analogous to pTA011 shown in FIG. 29, with the p76 regulatory region instead of the p72 (alcohol oxidase) regulatory region.

Vector pTAF.85 was then treated in an analogous fashion as vector pTA013 to give plasmids pTAFH.85, pT76H1 and pT76H2. Thus, the following vectors were cleaved and ligated:

| pTAF.85 plus | Resulting Plasmid |
|---|---|
| pTAFH1 | pTAFH.85 |
| pYJ30 | pT76H1 |
| pYA2 | pT76H2 |

EXAMPLE XV

Regulation of β-Galactosidase Production in *Pichia pastoris*

The production of β-galactosidase by several *Pichia pastoris* GS115 (NRRL Y-15851) transformants grown on different carbon sources and under different conditions was investigated. The transformed strains were grown in minimal medium containing 0.5 μg/mL of biotin and 0.1% glucose at 30° C. until they reached stationary phase. The cells were then collected by centrifugation and transferred to minimal medium containing 0.5 μg/mL of biotin and 0.5% methanol and grown for about 3-5 generations at 30° C. After this initial growth on methanol, cells were collected by centrifugation and transferred to fresh minimal medium containing 0.5 μg/mL of biotin and either 0.1% glucose of 0.3% methanol as carbon source. The cells were then incubated at 30° C. for about 80 hours, with samples being periodically withdrawn to determine the alcohol oxidase and β-galactosidase levels. After about 20-50 hours, the carbon source was depleted and thereafter the cells were maintained under these carbon source starvation conditions. The results are summarized in the Table I.

TABLE I

Maximal levels (incubation time, hrs) of β-galactosidase and alcohol oxidase (Units/0D$_{600}$) in transformants of *Pichia pastoris* NRRL Y-15851

| plasmid | β-galactosidase[a] | | | Alcohol Oxidase[a] | | |
| --- | --- | --- | --- | --- | --- | --- |
| | 1% glucose | glucose starvation | 0.3% methanol | 1% glucose | glucose starvation | 0.3% methanol |
| pSAOH1 | 0 | 660 (20) | 1361 (0) | 0 | 35 | 530 |
| pSAOH5 | 0.1–0.2 | 567 (20) | 1168 (0) | 0 | 60 | 550 |
| pSAOH10 | 0 | 886 (20) | 1559 (0) | 0 | 167 | 425 |
| pTAFH.85 | 0 | 0.17 (80) | 0.5 | 0 | nd | nd |
| pT76H1 | 0 | 3.20 (80) | 0 | 0 | nd | nd |
| pT76H2 | 0 | nd | nd | 0 | nd | nd |
| pT76H3 | 0 | 20 | 781 | 0 | nd | nd |
| pT76H4 | 0.3–0.6 | 40 (80) | 3100 | 0 | nd | nd |

[a]Cells were withdrawn at different timepoints and β-galactosidase and alcohol oxidase activity assays were performed as described in the text.

Alcohol oxidase was determined by the dye-peroxidase method described above (See Example VII) and β-galactosidase was determined as follows:

| β-Galactosidase Assay | | |
| --- | --- | --- |
| A. Solutions required: | | |
| Z-buffer: | | Final concentration |
| Na$_2$HPO$_4$.7H$_2$O | 16.1 g | 0.06 M |
| NaH$_2$PO$_4$ | 5.5 g | 0.04 M |
| KCl | 0.75 g | 0.01 M |
| MgSO$_4$.7H$_2$O | 0.246 g | 0.001 M |
| 2-mercaptoethanol | 2.7 mL | 0.05 M | fill up to 1L;
pH should be 7

O-Nitrophenyl-β-D-galactoside (ONPG):
Dissolve 400 mg ONPG (Sigma N-1127) in 100 mL of distilled water to make a 4 mg/mL ONPG solution.

B. Assay Procedure:
1. Withdraw an aliquot from the culture medium (0.1–0.5 OD$_{600}$ of yeast cells), centrifuge and wash cell pellet with water.
2. Add 1 mL of Z buffer to the cell pellet, 30 μL of CHCl$_3$ and 30 μL of 0.1% SDS, vortex, incubate 5 minutes at 30° C.
3. Start reaction by adding 0.2 mL of ONPG (4 mg/mL), vortex.
4. Stop reaction by adding 0.5 mL of a 1 M Na$_2$CO$_3$ solution at appropriate time points A$_{420}$<1).
5. Read absorbance of supernatant at 420 nm.

C. Calculation of β-galactosidase Activity Units:
1 U=1 nmole of orthonitrophenol (ONP) formed per minute at 30° C. and a pH 7.

1 nmole of ONP has an absorbance at 420 nm (A$_{420}$) of 0.0045 with a 1 cm pathlength; thus, an absorbance of 1 at 420 nm represents 222 nmole OHP/mL, or 378 nmole/1.7 mL since the total volume of supernatant being analyzed is 1.7 mL. Hence, Units expressed in the Tables are calculated:

$$U = \frac{A_{420}}{t(\min)} \times 378$$

The results presented in Table I indicate that a protein foreign to yeast, i.e., β-galactosidase, can be produced in *Pichia pastoris* regulated either by the presence of methanol in the nutrient medium or by carbon source starvation after growth on a catabolite repressing carbon source.

EXAMPLE XVI

Regulation of β-Galactosidase Production in *S. cerevisiae*

*Saccharomyces cerevisiae* SEY2102, a strain requiring uracil, leucine and histidine supplementation for survival, was transformed with plasmids pTA013 and PT76U1. Transformed organisms were readily isolated by selecting for colonies which did not require uracil supplementation for growth. The isolated transformants, have been given the laboratory designation SEY2102-pTA013, and SEY2102-pT76U1, respectively. SEY2102-pTA013 has been deposited with the Northern Regional Research Center in Peoria, Ill. to insure access to the public as of the deposit date of Aug. 31, 1984. This strain has been assigned accession number NRRL Y-15858.

Cells of NRRL Y-15858 and SEY2102-pT76U1 were incubated at 30° C. for about 3-4 generations in minimal medium containing 20 μg/mL of histidine and leucine and 5% glucose. Cells were then shifted, i.e., collected by centrifugation and transferred into YP medium with 3% of the carbon source indicated in Table II and grown for about 5 generations at 30° C. Cells were then incubated for an additional 50 hours under carbon source starvation conditions, and periodically sampled for β-galactosidase. The results are summarized in Table III.

TABLE II

Production of β-Galactosidase by *s. cerevisiae*
β-galactosidase, Units/OD$_{600}$

A. Alcohol oxidase regulatory region (pTA013)

| Carbon Source (3%) | After 5 Generations | Starvation Conditions | | |
|---|---|---|---|---|
| | | 6 hrs. | 20 hrs. | 50 hrs. |
| glucose | 0.2 | 105 | 66 | nd |
| fructose | 0.3 | 30 | 31 | 28 |
| ethanol | 23 | 137 | 115 | 77 |
| glycerol | 640 | 806 | 656 | 788 |
| galactose | 982 | 960 | 651 | 766 |

B. p76 regulatory region (pT76U1)

| Carbon Source (5%) | After 5 Generations | Starvation Conditions | | |
|---|---|---|---|---|
| | | 12 hrs. | 25 hrs. | 30 hrs. |
| glucose | 2.3 | 254 | 815 | 803 |
| glycerol | 470 | nd | nd | nd |

These results indicate that a protein foreign to yeast, i.e., β-galactosidase, can be produced by *Saccharomyces cerevisiae* regulated by the p72 (alcohol oxidase) and p76 regulatory regions under conditions of carbon source starvation when a catabolite repressing carbon source is employed for growth, or by growth of transformed *S. cerevisiae* cells on a relatively non-catabolite repressing carbon source such as glycerol or galactose.

The expression levels of β-galactosidase in *S. cerevisiae* under the control of the regulatory regions of this invention can be compared to the expression levels possible with other *S. cerevisiae* regulated promoters.

| Promoter | Carbon Source | β-galactosidase, Units/OD$_{600}$ |
|---|---|---|
| cytochrome C-lacZ fusion (CYC1) | Raffinose (3%) | 460 |
| galactose permease-lac-Z fusion (GAL2) | Galactose (2%) | 450 |
| Invertase-lacZ fusion (SUC2) | Glucose (0.1%) | 160 |

It is seen that the regulatory region of the invention surprisingly are at least as effective as, or more effective as *S. cerevisiae* promoters than promoters native to *S. cerevisiae*.

EXAMPLE XVII

Southern Hybridizations With Yeast Genomic DNA

Nine different methanol assimilating yeasts and one methanol non-assimilating yeast were grown in minimal media (IM1, See Example 1) plus 0.75% methanol or 1.0% glucose, respectively. Total chromosomal DNA was isolated as described in Example VI, i.e., total nucleic acids were isolated, treated with RNase A, extracted first with phenol/chloroform/isoamyl alcohol, then with chloroform/isoamyl alcohol and finally ethanol precipitated. The precipitated DNA was resuspended in a minimum volume of TE buffer and centrifuged to clean the DNA solution.

Southern hybridization filters were prepared as described in Example VI, i.e., 10 μg of total DNA from various yeast species was digested with excess HindIII, electrophoresed, DNA denatured, the gel neutralized and DNA transferred to nitrocellulose filters. Prehybridization conditions for these filters included treatment with 50% deionized formamide, 6x SSC, 5x Denhardt's, 1 mM EDTA, 0.1% SDS and 100 μg/mL denatured salmon sperm DNA, at 42° C. overnight. The same conditions were used as hybridization medium using $_{32}$P-nick-translated probes at a final concentration of $10^6$ cpm/mL. The probes included the cDNA inserts (PstI fragments) from clones pPC 8.3, pPC 15.0 and pPC 6.7, as well as a 2.7 kbp BglII DNA fragment of the P. pastoris HIS4 gene. Each of these probes were separately used on identical filters for hybridization lasting 24 hours at 42° C. After hybridization the filters were washed twice for 15 minutes at room temperature, and three times at 65° C. for 15 minutes in a solution containing 2x SSC, 1 mM EDTA, 0.1% SDS and 0.1% sodium pyrophosphate. Other washes were tried at lower stringency, i.e., at 55° C. and 42° C., to confirm thy hybridization results. The filters were then autoradiographed for 72 hours. The results of these hybridizations are summarized in Table III.

TABLE III

Hybridization of *P. pastoris* Genes to Various Yeast Chromosomal DNA*

| | | P. pastoris | | | |
|---|---|---|---|---|---|
| | | HIS4 | pPC 8.3 | pPC 15.0 | pPC 6.7 |
| (1) | P. pastoris NRRL Y-11430 | + | + | + | + |
| (2) | P. pastoris NRRL Y-1603 | + | + | + | + |
| (3) | Hansenula capsulatum | + | + | + | + |
| (4) | H. henricii | + | + | + | + |
| (5) | H. nonfermentans | + | + | + | + |
| (6) | H. polyrmorpha | (+) | + | (+) | + |
| (7) | H. wickerhamii | + | + | + | + |
| (8) | Torulopsis molischiana | + | + | + | + |
| (9) | Saccharomyces cerevisiae | (+) | − | − | − |
| (10) | P. pastoris NRRL Y-15851 | + | + | + | + |

*Legend:
+ hybridization
(+) weak hybridization
− no hybridization observed under the conditions employed The results presented in Table III indicate that genes for polypeptides analogous to p76, p72 and p40 are present in virtually all methanol-assimilating yeasts. It is notable that none of these three genes were observed by hybridization of DNA from a methanol non-assimilating yeast, *S. cerevisiae*, while homology between the *P. pastoris* HIS4 gene and the HIS4 gene from *S. cerevisiae* was readily observed.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

BIBLIOGRAPHY

Birnboim and Doly (1979) Nucl. Acids Res. 7, 1513–1523.

M. G. Douglas et al (1984) Proc. Nat. Acad. Sci. U.S. 81, 3983–3987.

Hinnen et al (1978) Proc. Nat. Acad. Sci., USA 75, 1929–1933.

Z. A. Janowicz et al (1985) Nucl. Acids Res. 13, 3043–3062.

A. M. Ledeboer et al (1985) Nucl. Acids Res. 13, 3063–3082.

Maxam and Gilbert (1980) in Methods in Enzymology 65, 499–560.

Southern (1975) J. Mol. Biol. 98 503-517.
Sanger et al (1980) J. Mol. Biol. 143, 161-178.

That which is claimed is:

1. An isolated DNA fragment derived from a yeast of the species *Pichia pastoris* comprising a regulatory region derived from a gene which codes for
   alcohol oxidase
   polypeptide p76 or
   polypeptide p40
wherein said regulatory region is responsive to the presence of methanol in the culture medium with which a host organism for said DNA fragment is in contact and wherein said regulatory region is capable of controlling the transcription of messenger RNA when positioned at the 5' end of the DNA which codes for the production of said messenger RNA.

2. An isolated DNA fragment in accordance with claim 1 wherein said yeast is *Pichia pastoris* NRRL y-11430.

3. An isolated DNA fragment in accordance with claim 1 wherein said regulatory region controls the transcription of messenger RNA which codes for the production of alcohol oxidase.

4. An isolated DNA fragment in accordance with claim 1 wherein said regulatory region controls the transcription of messenger RNA which codes for the production of the polypeptide p76.

5. An isolated DNA fragment in accordance with claim 2 wherein said regulatory region controls the transcription of messenger RNA which codes for the production of the polypeptide p40.

6. An isolated DNA fragment in accordance with claim 3 further comprising the 3' sequence of DNA downstream of the DNA which codes for the production of alcohol oxidase.

7. An isolated DNA fragment in accordance with claim 4 further comprising the 3' sequence of DNA downstream of the DNA which codes for the production of polypeptide p76.

8. An isolated DNA fragment in accordance with claim 5 further comprising the 3' sequence of DNA downstream of the DNA which codes for the production of polypeptide p40.

9. An isolated DNA fragment in accordance with claim 1 wherein said messenger RNA codes for the production of a heterologous polypeptide.

10. An isolated DNA fragment in accordance with claim 3 wherein said fragment is characterized as shown by the restriction map in FIG. 5 of the drawings.

11. An isolated DNA fragment in accordance with claim 10 further comprising an additional fragment selected from the group characterized as shown by the restriction maps in FIG. 8 of the drawings.

12. An isolated DNA fragment in accordance with claim 4 wherein said fragment is selected from the group characterized as shown by the restriction maps in FIG. 4 of the drawings.

13. An isolated DNA fragment in accordance with claim 12 further comprising the additional fragment characterized as shown by the restriction map in FIG. 7 of the drawings.

14. An isolated DNA fragment in accordance with claim 5 wherein said fragment is characterized as shown by the restriction map in FIG. 6 of the drawings.

15. An isolated DNA fragment in accordance with claim 14 further comprising the additional fragment characterized as shown by the restriction map in FIG. 9 of the drawings.

16. An isolated DNA fragment in accordance with claim 3 wherein said fragment has the nucleotide sequence:

| | | | |
|---|---|---|---|
| 5'-ATGCTTCCAA | GATTCTGGTG | GGAATACTGC | TGATAGCCTA |
| ACGTTCATGA | TCAAAATTTA | ACTGTTCTAA | CCCCTACTTG |
| GACAGGCAAT | ATATAAACAG | AAGGAAGCTG | CCCTGTCTTA |
| AACCTTTTTT | TTTATCATCA | TTATTAGCTT | ACTTTCATAA |
| TTGCGACTGG | TTCCAATTGA | CAAGCTTTTG | ATTTTAACGA |
| CTTTTAACGA | CAACTTGAGA | AGATCAAAAA | ACAACTAATT |
| ATTCGAAACG-3' | | | |

17. A DNA fragment in accordance with claim 19 further comprising an additional fragment positioned at the 3' end of the DNA which codes for the production of messenger RNA; wherein said additional fragment is selected from the group characterized by the restriction maps in FIG. 8 of the drawings.

18. An isolated DNA fragment in accordance with claim 3 wherein said fragment has the nucleotide sequence:

| | | | |
|---|---|---|---|
| 5'-AATGGCCCAAA | CTGACAGTTT | AAACGCTGTC | TTGGAACCTA |
| ATATGACAAA | AGCGTGATCT | CATCCAAGAT | GAACTAAGTT |
| TGGTTCGTTG | AAATCCTAAC | GGCCAGTTGG | TCAAAAAGAA |
| ACTTCCAAAA | GTCGGCATAC | CGTTTGTCTT | GTTTGGTATT |
| GATTGACGAA | TGCTCAAAAA | TAATCTCATT | AATGCTTAGC |
| GCAGTCTCTC | TATCGCTTCT | GAACCCGGTG | GCACCTGTGC |
| CGAAACGCAA | ATGGGGAAAC | AACCCGCTTT | TTGGATGATT |
| ATGCATTGTC | TCCACATTGT | ATGCTTCCAA | GATTCTGGTG |
| GGAATACTGC | TGATAGCCTA | ACGTTCATGA | TCAAAATTTA |
| ACTGTTCTAA | CCCCTACTTG | GACAGGCAAT | ATATAAACAG |
| AAGGAAGCTG | CCCTGTCTTA | AACCTTTTTT | TTTATCATCA |
| TTATTAGCTT | ACTTTCATAA | TTGCGACTGG | TTCCAATTGA |
| CAAGCTTTTG | ATTTTAACGA | CTTTTAACGA | CAACTTGAGA |
| AGATCAAAAA | ACAACTAATT | ATTCGAAACG-3'. | |

19. An isolated DNA fragment in accordance with claim 3 wherein said fragment has the nucleotide sequence:

| | |
|---|---|
| 5'- AGATCTAA | CATCCAAAGA |

-continued

| | | | |
|---|---|---|---|
| CGAAAGGTTG | AATGAAACCT | TTTTGCCATC | CGACATCCAC |
| AGGTCCATTC | TCACACATAA | GTGCCAAACG | CAACAGGAGG |
| GGATACACTA | GCAGCAGACG | TTGCAAACGC | AGGACTCATC |
| CTCTTCTCTA | ACACCATTTT | GCATGAAAAC | AGCCAGTTAT |
| GGGCTTGATG | GAGCTCGCTC | ATTCCAATTC | CTTCTATTAG |
| GCTACTAACA | CCATGACTTT | ATTAGCCTGT | CTATCCTGGC |
| CCCCCTGGCG | AGGTCATGTT | TGTTTATTTC | CGAATGCAAC |
| AAGCTCCGCA | TTACACCCGA | ACATCACTCC | AGATGAGGGC |
| TTTCTGAGTG | TGGGGTCAAA | TAGTTTCATG | TTCCCAAATG |
| GCCCAAAACT | GACAGTTTAA | ACGCTGTCTT | GGAACCTAAT |
| ATGACAAAAG | CGTGATCTCA | TCCAAGATGA | ACTAAGTTTG |
| GTTCGTTGAA | ATCCTAACGG | CCAGTTGGTC | AAAAAGAAAC |
| TTCCAAAAGT | CGGCATACCG | TTTGTCTTGT | TTGGTATTGA |
| TTGACGAATG | CTCAAAAATA | ATCTCATTAA | TGCTTAGCGC |
| AGTCTCTCTA | TCGCTTCTGA | ACCCGGTGGC | ACCTGTGCCG |
| AAACGCAAAT | GGGGAAACAA | CCCGCTTTTT | GGATGATTAT |
| GCATTGTCCT | CCACATTGTA | TGCTTCCAAG | ATTCTGGTGG |
| GAATACTGCT | GATAGCCTAA | CGTTCATGAT | CAAAATTTAA |
| CTGTTCTAAC | CCCTACTTGG | ACAGGCAATA | TATAAACAGA |
| AGGAAGCTGC | CCTGTCTTAA | ACCTTTTTTT | TTATCATCAT |
| TATTAGCTTA | CTTTCATAAT | TGCGACTGGT | TCCAATTGAC |
| AAGCTTTTGA | TTTTAACGAC | TTTTAACGAC | AACTTGAGAA |
| GATCAAAAAA | CAACTAATTA | TTCGAAACG-3' | |

20. An isolated DNA fragment in accordance with claim 1 wherein said fragment has the nuclotide sequence:

| | | | |
|---|---|---|---|
| | | | 5'-TT |
| CACCCATACA | ACTATAAACC | TTTAGCAATTG | AAATAACCCC |
| AATTCATTGT | TCCGAGTTTA | ATATACTTGC | CCCTATAAGA |
| AACCAAGGGA | TTTCAGCTTC | CTTACCCCAT | GAACAGAATC |
| TTCCATTTAC | CCCCCACTGG | AGAGATCCGC | CCAAACGAAC |
| AGATAATAGA | AAAAAACAAT | TCGGACACCA | AGAACACTTT |
| CTCAGCCAAT | TAAAGTCATT | CCATGCACTC | CCTTTAGCTG |
| CCGTTCCATC | CCTTTGTTGA | GCAACACCAT | CGTTAGCCAG |
| TACGAAAGAG | GAAACTTAAC | CGATACCTTG | GAGAAATCTA |
| AGGCGCGAAT | GAGTTTAGCC | TAGATATCCT | TAGTGAAGGG |
| TGTCCGATAC | TTCTCCACAT | TCAGTCATAG | ATGGGCAGCT |
| TGTATCATGA | AGAGACGGAA | ACGGGCATAA | GGGTAACCGC |
| CAAATTATAT | AAAGACAACA | TGCCCCAGTT | TAAAGTTTTT |
| CTTTCCTATT | CTTGTATCCT | GAGTGACCGT | TGTGTTTAAT |
| ATAAAAAGTT | CGTTTTAACT | TAAGACCAAA | ACCAGTTACA |
| ACAAATTATA | ACCCCTCTAA | ACACTAAAGT | TCACTCTTAT |
| CAAACTATCA | AACATCAAAA-3' | | |

21. An isolated DNA fragment in accordance with claim 1 further comprising:
a polypeptide coding region; wherein said regulatory region is positioned at the 5' end of said polypeptide coding region.

22. An isolated DNA fragment in accordance with claim 21 wherein said polypeptide code region codes for the production of alcohol oxidase.

23. An isolated DNA fragment in accordance with claim 22 wherein said fragment has the nucleotide sequence:

| | | | | | | | | | | |
|---|---|---|---|---|---|---|---|---|---|---|
| | | | | | 5'-ATG | GCT | ATC | CCC | GAA | GAG | TTT |
| | | | | | 3'-TAC | CGA | TAG | GGG | CTT | CTC | AAA |
| GAT | ATC | CTA | GTT | CTA | GGT | GGT | GGA | TTC | AGT | GGA | TCC |
| CTA | TAG | GAT | CAA | GAT | CCA | CCA | CCT | AGG | TCA | CCT | AGG |
| TGT | ATT | TCC | GGA | AGA | TTG | GCA | AAC | TTG | GAC | CAC | TCC |
| ACA | TAA | AGG | CCT | TCT | AAC | CGT | TTG | AAC | CTG | GTG | AGG |
| TTG | AAA | GTT | GGT | CTT | ATC | GAA | GCA | GGT | GAG | AAC | CAA |
| AAC | TTT | CAA | CCA | GAA | TAG | CTT | CGT | CCA | CTC | TTG | GTT |
| CCT | CAA | CAA | CCC | ATG | GGT | CTA | CCT | TCC | AGG | TAT | TTA |
| GGA | GTT | GTT | GGG | TAC | CCA | GAT | GGA | AGG | TCC | ATA | AAT |
| CCC | AAG | AAA | CAG | AAG | TTG | GAC | TCC | AAG | ACT | GCT | TCC |
| GGG | TTC | TTT | GTC | TTC | AAC | CTG | AGG | TTC | TGA | CGA | AGG |
| TTC | TAC | ACT | TCT | AAC | CCA | TCT | CCT | CAC | TTG | AAT | GGT |
| AAG | ATG | TGA | AGA | TTG | GGT | AGA | GGA | GTG | AAC | TTA | CCA |
| AGA | AGA | GCC | ATC | GTT | CCA | TGT | GCT | AAC | GTC | TTG | GGT |
| TCT | TCT | CGG | TAG | CAA | GGT | ACA | CGA | TTG | CAG | AAC | CCA |
| GGT | GGT | TCT | TCT | ATC | AAC | TTC | ATG | ATG | TAC | ACC | AGA |
| CCA | CCA | AGA | AGA | TAG | TTG | AAG | TAC | TAC | ATG | TGG | TCT |
| GGT | TCT | GCT | TCT | GAT | TCT | GAT | GAC | TTN | CAA | GCC | GAG |
| CCA | AGA | CGA | AGA | CTA | AGA | CTA | CTG | AAN | GTT | CGG | CTC |
| GGC | TCG | AAA | ACA | GAG | GAC | TTG | CTT | CCA | TTG | ATG | AAA |
| CCG | AGC | TTT | TGT | CTC | CTG | AAC | GAA | GGT | AAC | TAC | TTT |
| AAG | ACT | GAG | ACC | TAC | CAA | AGA | GCT | TGN | CAA | CNA | TAC |
| TTC | TGA | CTC | TGG | ATG | GTT | TCT | CGA | ACN | GTT | GNT | ATG |

-continued

| | | | | | | | | | | |
|---|---|---|---|---|---|---|---|---|---|---|
| CCT | GAC | ATT | CAC | GGT | TTC | GAA | GGT | CCA | ATC | AAG | GTT |
| GGA | CTG | TAA | GTG | CCA | AAG | CTT | CCA | GGT | TAG | TTC | CAA |
| TCT | TTC | GGT | AAC | TAC | ACC | TAC | CCA | GTT | TGC | CAG | GAC |
| AGA | AAG | CCA | TTG | ATG | TGG | ATG | GGT | CAA | ACG | GTC | CTG |
| TTC | TTG | AGG | GCT | TCT | GAG | TCC | CAA | GGT | ATT | CCA | TAC |
| AAG | AAC | TCC | CGA | AGA | CTC | AGG | GTT | CCA | TAA | CGT | ATG |
| GTT | GAC | GAT | CTG | GAA | GAC | TTG | GTA | CTG | ACT | CAC | GGT |
| CAA | CTG | CTA | GAC | CTT | CTG | AAC | CAT | GAC | TGA | GTG | CCA |
| GCT | GAA | CAC | TGG | TTG | AAG | TGG | ATC | AAC | AGA | GAC | ACT |
| CGA | CTT | GTG | ACC | AAC | TTC | ACC | TAG | TTG | TCT | CTG | TGA |
| CGT | CGT | TCC | GAC | TCT | GCT | CAT | GCA | TTT | GTC | CAC | TCT |
| GCA | GCA | AGG | CTG | CGA | AGA | GTA | CGT | AAA | CAG | GTG | AGA |
| TCT | ACT | ATG | AGA | AAC | CAC | GAC | AAC | TTG | TAC | TTG | ATC |
| AGA | TGA | TAC | TCT | TTG | GTG | CTG | TTG | AAC | ATG | AAC | TAG |
| TGT | AAC | ACG | AAG | GTC | GAC | AAA | ATT | ATT | GTC | GAA | GAC |
| ACA | TTG | TGC | TTC | CAG | CTG | TTT | TAA | TAA | CAG | CTT | CTG |
| GGA | AGA | GCT | GCT | GCT | GTT | AGA | ACC | GTT | CCA | AGC | AAG |
| CCT | TCT | CGA | CGA | CGA | CAA | TCT | TGG | CAA | GGT | TCG | TTC |
| CCT | TTG | AAC | CCA | AAG | AAG | CCA | AGT | CAC | AAG | ATC | TAC |
| GCA | AAC | TTG | GGT | TTC | TTC | GGT | TCA | GTG | TTC | TAG | ATG |
| CGT | GCT | AGA | AAG | CAA | ATC | TTT | TTG | TCT | TGT | GGT | ACC |
| GCA | CGA | TCT | TTC | GTT | TAG | AAA | AAC | AGA | ACA | CCA | TGG |
| ATC | TCC | TCT | CCA | TTG | GTT | TTG | CAA | AGA | TCC | GGT | TTT |
| TAG | AGG | AGA | GGT | AAC | CAA | AAC | GTT | TCT | AGG | CCA | AAA |
| GGT | GAC | CCA | ATC | AAG | TTG | AGA | GCC | GCT | GGT | GTT | AAG |
| CCA | CTG | GGT | TAG | TTC | AAC | TCT | CGG | CGA | CCA | CAA | TTC |
| CCT | TTG | GTC | AAC | TTG | CCA | GGT | GTC | GGA | AGA | AAC | TTC |
| GGA | AAC | CAG | TTG | AAC | GGT | CCA | CAG | CCT | TCT | TTG | AAG |
| CAA | GAC | CAT | TAT | TGT | TTC | TTC | AGT | CCT | TAC | AGA | ATC |
| GTT | CTG | GTA | ATA | ACA | AAG | AAG | TCA | GGA | ATG | TCT | TAG |
| AAG | CCT | CAG | TAC | GAG | TCT | TTC | GAT | GAC | TTC | GTC | CGT |
| TTC | GCA | GTC | ATG | CTC | AGA | AAG | CTA | CTG | AAG | CAG | GCA |
| GGT | GAT | GCT | GAG | ATT | CAA | AAG | AGA | GTC | GTT | GAC | CAA |
| CCA | CTA | CGA | CTC | TAA | GTT | TTC | TCT | CAG | CAA | CTG | GTT |
| TGG | TAC | GCC | AAT | GGT | ACT | GGT | CCT | CTT | GCC | ACT | AAC |
| ACC | ATG | CGG | TTA | CCA | TGA | CCA | GGA | GAA | CGG | TGA | TTG |
| GGT | ATC | GAA | GCT | GGT | GTC | AAG | TTC | ACA | CCA | GGT |
| CCA | TAG | CTT | CGA | CCA | CAG | TTC | TAG | TCT | GGT | TGT | GGT |
| GAA | GAA | CTC | TCT | CAA | ATG | GAC | GAA | TCC | TTC | CAG | GAG |
| CTT | CTT | GAG | AGA | GTT | TAC | CTG | CTT | AGG | AAG | GTC | CTC |
| GGT | TAC | AGA | GAA | TAC | TTC | GAA | GAC | AAG | CCA | GAC | AAG |
| CCA | ATG | TCT | CTT | ATG | AAG | CTT | CTG | TTC | GGT | CTG | TTC |
| CCA | GTT | ATG | CAC | TAC | TCC | ATC | ATT | GCT | GGT | TTC | TTC |
| GGT | CAA | TAC | GTG | ATG | AGG | TAG | TAA | CGA | CCA | AAG | AAG |
| GGT | GAC | CAC | ACC | AAG | ATT | CCT | CCT | GGA | AAG | TAC | ATG |
| CCA | CTG | GTG | TGG | TTC | TAA | GGA | GGA | CCT | TTC | ATG | TAC |
| ACT | ATG | TTC | CAC | TTC | TTG | GAA | TAC | CCA | TTC | TCC | AGA |
| TGA | TAC | AAG | GTG | AAG | AAC | CTT | ATG | GGT | AAG | AGG | TCT |
| GGT | TCC | ATT | CAC | ATT | ACC | TCC | CCA | GAC | CCA | TAC | GCA |
| CCA | AGG | TAA | GTG | TAA | TGG | AGG | GGT | CTG | GGT | ATG | CGT |
| GCT | CCA | GAC | TTC | GAC | CGA | GGT | TTC | ATG | AAC | GAT | GAA |
| CGA | GGT | CTG | AAG | CTG | GCT | CCA | AAG | TAC | TTG | CTA | CTT |
| AGA | GAC | ATG | GCT | CCT | ATG | GTT | TGG | GCT | TAC | AAG | TCT |
| TCT | CTG | TAC | CGA | GGA | TAC | CAA | ACC | CGA | ATG | TTC | TTC |
| TCT | AGA | GAA | ACC | GCT | AGA | AGA | AGT | GAC | CAC | TTT | GCC |
| AGA | TCT | CTT | TGG | CGA | TCT | TCT | TCA | CTG | GTG | AAA | CGG |
| GGT | GAG | GTC | ACT | TCT | CAC | CAC | CCT | CTG | TTC | CCA | TAC |
| CCA | CTC | CAG | TGA | AGA | GTG | GTG | GGA | GAC | AAG | GGT | ATG |
| TCA | TCC | GAG | GCC | AGA | GCC | TTG | GAA | ATG | GAT | TTG | GAG |
| AGT | AGG | CTC | CGG | TCT | CGG | AAC | CTT | TAC | CTA | AAC | CTC |
| ACC | TCT | AAT | GCC | TAC | GGT | GGA | CCT | TTG | AAC | TTG | TCT |
| TGG | AGA | TTA | CGG | ATG | CCA | CCT | GGA | AAC | TTG | AAC | AGA |
| GCT | GGT | CTT | GCT | CAC | GGT | TCT | TGG | ACT | CAA | CCT | TTG |
| CGA | CCA | GAA | CGA | GTG | CCA | AGA | ACC | TGA | GTT | GGA | AAC |
| AAG | AAG | CCA | ACT | GCA | AAG | AAC | GAA | GGC | CAC | GIT | ACT |
| TTC | TTC | GGT | TGA | CGT | TTC | TTG | CTT | CCG | GTG | CAA | TGA |
| TCG | AAC | CAG | GTC | GAG | CTT | CAT | CCA | GAC | ATC | GAG | TAC |
| AGC | TTG | GTC | CAG | CTC | GAA | GTA | GGT | CTG | TAG | CTC | ATG |
| GAT | GAG | GAG | GAT | GAC | AAG | GCC | ATT | GAG | ACC | TAC | ATT |
| CTA | CTC | CTC | CTA | CTG | TTC | CGG | TAA | CTC | TTG | ATG | TAA |
| CGT | GAG | CAC | ACT | GAG | ACC | ACA | TGG | CAC | TGT | CTG | GGA |
| GCA | CTC | GTG | TGA | CTC | TGG | TGT | ACC | GTG | ACA | CCA | GGT |
| ACC | TGT | TCC | ATC | GGT | CCA | AGA | GAA | GGT | TCC | AAG | ATC |
| TGG | ACA | AGG | TAG | CCA | GGT | TCT | CTT | CCA | AGG | TTC | TAG |
| GTC | AAA | TGG | GGT | GGT | GTT | TIG | GAC | CAC | AGA | TCC | AAC |
| CAG | TTT | ACC | CCA | CCA | CAA | AAC | CTG | GTG | TCT | AGG | TTG |
| GTT | TAC | GGA | GTC | AAG | GGC | TIG | AAG | GTT | GGT | GAC | TTG |
| CAA | ATG | CCT | CAG | TTC | CCG | AAC | TTC | CAA | CCA | CTG | AAC |
| TCC | GTG | TGC | CCA | GAC | AAT | GTT | GGT | TGT | AAC | ACC | TAC |
| AGG | CAC | ACG | GGT | CTG | TTA | CAA | CCA | ACA | TTG | TGG | ATG |
| ACC | ACC | GCT | CTT | TTG | ATC | GGT | GAA | AAG | ACT | GCC | ACT |
| TGG | TGG | CGA | GAA | AAC | TAG | CCA | CTT | TTC | TGA | CGG | TGA |

-continued

| TTG | GTT | GGA | GAA | CAT | TTA | GGA | TAC | TCT | GGT | GAG | GCC |
| AAC | CAA | CCT | CTT | CTA | AAT | CCT | ATG | AGA | CCA | CTC | CGG |
| TTA | GAC | ATG | ACT | GTT | CCT | CAG | TTC | AAG | TTG | GGC | ACT |
| AAT | CTG | TAC | TGA | CAA | GGA | GTC | AAG | TTC | AAC | CCG | TGA |
| TAC | GAG | AAG | ACC | GGT | CTT | GCT | AGA | TTC | TAA-3' | | |
| ATG | CTC | TTC | TGG | CCA | GAA | CGA | TCT | AAG | ATT-5' | | |

24. An isolated DNA fragment in accordance with claim 21 wherein said polypeptide coding region codes for the production of polypeptide p76.

25. An isolated DNA fragment in accordance with claim 21 wherein said polypeptide coding region codes for the production of polypeptide p40.

26. An isolated DNA fragment in accordance with claim 21 wherein said polypeptide coding region codes for the production of a heterologous polypeptide.

27. An isolated DNA fragment in accordance with claim 26 wherein said heterologous polypeptide is β-galactosidase.

28. An isolated DNA fragment in accordance with claim 27 wherein said DNA fragment is selected from the group characterized by the restriction maps in FIG. 15 of the drawings.

29. An isolated DNA fragment in accordance with claim 27 wherein said DNA fragment is characterized by the restriction map in FIG. 16 of the drawings.

30. An isolated DNA fragment in accordance with claim 22 wherein said DNA fragment is characterized by the restriction map in FIG. 2 of the drawings.

31. An isolated DNA fragment in accordance with claim 24 wherein said DNA fragment is characterized by the restriction map in FIG. 10 of the drawings.

32. An isolated DNA fragment in accordance with claim 25 wherein said DNA fragment is characterized by the restriction map in FIG. 11 of the drawings.

33. An isolated DNA fragment in accordance with claim 21 further comprising a 3' sequence of DNA downstream of the polypeptide coding region; wherein said 3' sequence of DNA is capable of controlling the polyadenylation, termination of transcription and termination of translation of messenger RNA coded for by said polypeptide coding region.

34. An isolated DNA fragment in accordance with claim 21 wherein said DNA fragment further comprises one or more additional DNA sequences selected from the group consisting of
bacterial plasmid DNA,
bacteriophage DNA,
yeast plasmid DNA, and
yeast chromosomal DNA.

35. An isolated DNA fragment in accordance with claim 34 wherein said yeast chromosomal DNA comprises an autonomously replicating DNA sequence and a marker gene.

36. An isolated DNA fragment in accordance with claim 33 wherein said DNA fragment further comprises one or more additional DNA sequence selected from the group consisting of
bacterial plasmid DNA,
bacteriophage DNA,
yeast Plasmid DNA, and
yeast chromosomal DNA.

37. An isolated DNA fragment in accordance with claim 36 wherein said yeast chromosomal DNA comprises an autonomously replicating DNA sequence and a marker gene.

38. A DNA fragment in accordance with claim 36 wherein said fragment is in the form of a closed circular hybrid plasmid.

39. An isolated DNA fragment comprising the 3' portion of the p40, p76 or alcohol oxidase genes derived from *Pichia pastoris* which fragment when positioned at the 3' end of a structural gene is capable of controlling the polyadenylation, termination of transcription and termination of translation of messenger corresponding to said structural gene and the 5' portion of the p40, p76 or alcohol oxidase genes derived from *Pichia pastoris* which fragment is responsive to the presence of methanol in the culture medium with which a host organism for said fragment is in contact and wherein said fragment is capable of controlling the transcription of messenger RNA when positioned at the 5' end of said structural gene.

40. An isolated DNA fragment in accordance with claim 39 wherein said DNA fragment is characterized by the restriction map in FIG. 7 of the drawings.

41. An isolated DNA fragment in accordance with claim 39 wherein said DNA fragment is selected from the group characterized by the restriction map in FIG. 8 of the drawings.

42. An isolated DNA fragment in accordance with claim 39 wherein said DNA fragment is characterized by the restriction map in FIG. 9 of the drawings.

43. An isolated gene derived from *Pichia pastoris* which upon expression codes for the production of biologically active alcohol oxidase or a biologically active sub-unit thereof.

44. A gene in accordance with claim 43 wherein said gene is characterized by the restriction map in FIG. 13 of the drawings.

45. A gene in accordance with claim 43 wherein said gene has the nucleotide sequence:

| | | | | | 5'-ATG | GCT | ATC | CCC | GAA | GAG | TTT |
| | | | | | 3'-TAC | CGA | TAG | GGG | CTT | CTC | AAA |
| GAT | ATC | CTA | GTT | CTA | GGT | GGT | GGA | TTC | AGT | GGA | TCC |
| CTA | TAG | GAT | CAA | GAT | CCA | CCA | CCT | AGG | TCA | CCT | AGG |
| TGT | ATT | TCC | GGA | AGA | TTG | GCA | AAC | TTG | GAC | CAC | TCC |
| ACA | TAA | AGG | CCT | TCT | AAC | CGT | TTG | AAC | CTG | GTG | AGG |
| TTG | AAA | GTT | GGT | CTT | ATC | GAA | GCA | GGT | GAG | AAC | CAA |
| AAC | TTT | CAA | CCA | GAA | TAG | CTT | CGT | CCA | CTC | TTG | GTT |
| CCT | CAA | CAA | CCC | ATG | GGT | CTA | CCT | TCC | AGG | TAT | TTA |
| GGA | GTT | GTT | GGG | TAC | CCA | GAT | GGA | AGG | TCC | ATA | AAT |
| CCC | AAG | AAA | CAG | AAG | TTG | GAC | TCC | AAG | ACT | GCT | TCC |
| GGG | TTC | TTT | GTC | TTC | AAC | CTG | AGG | TTC | TGA | CGA | AGG |

-continued

| | | | | | | | | | | |
|---|---|---|---|---|---|---|---|---|---|---|
| TTC | TAC | ACT | TCT | AAC | CCA | TCT | CCT | CAC | TTG | AAT | GGT |
| AAG | ATG | TGA | AGA | TTG | GGT | AGA | GGA | GTG | AAC | TTA | CCA |
| AGA | AGA | GCC | ATC | GTT | CCA | TGT | GCT | AAC | GTC | TTG | GGT |
| TCT | TCT | CGG | TAG | CAA | GGT | ACA | CGA | TTG | CAG | AAC | CCA |
| GGT | GGT | TCT | TCT | ATC | AAC | TTC | ATG | ATG | TAC | ACC | AGA |
| CCA | CCA | AGA | AGA | TAG | TTG | AAG | TAC | TAC | ATG | TGG | TCT |
| GGT | TCT | GCT | TCT | GAT | TCT | GAT | GAC | TTN | CAA | GCC | GAG |
| CCA | AGA | CGA | AGA | CTA | AGA | CTA | CTG | AAN | GTT | CGG | CTC |
| GGC | TCG | AAA | ACA | GAG | GAC | TTG | CTT | CCA | TTG | ATG | AAA |
| CCG | AGC | TTT | TGT | CTC | CTG | AAC | GAA | GGT | AAC | TAC | TTT |
| AAG | AAC | GAG | ACC | TAC | CAA | AGA | GCT | TGN | CAA | CNA | TAC |
| TTC | TGA | CTC | TGG | ATG | GTT | TCT | CGA | ACN | GTT | GNT | ATG |
| CCT | GAC | ATT | CAC | GGT | TTC | GAA | GGT | CCA | ATC | AAG | GTT |
| GGA | CTG | TAA | GTG | CCA | AAG | CTT | CCA | GGT | TAG | TTC | CAA |
| TCT | TTC | GGT | AAC | TAC | ACC | TAC | CCA | GTT | TGC | CAG | GAC |
| AGA | AAG | CCA | TTG | ATG | TGG | ATG | GGT | CAA | ACG | GTC | CTG |
| TTC | TTG | AGG | GCT | TCT | GAG | TCC | CAA | GGT | ATT | CCA | TAC |
| AAG | AAC | TCC | CGA | AGA | CTC | AGG | GTT | CCA | TAA | CGT | ATG |
| GTT | GAC | GAT | CTG | GAA | GAC | TTG | GTA | CTG | ACT | CAC | GGT |
| CAA | CTG | CTA | GAC | CTT | CTG | AAC | CAT | GAC | TGA | GTG | CCA |
| GCT | GAA | CAC | TGG | TTG | AAG | TGG | ATC | AAC | AGA | GAC | ACT |
| CGA | CTT | GTG | ACC | AAC | TTC | ACC | TAG | TTG | TCT | CTG | TGA |
| CGT | CGT | TCC | GAC | TCT | GCT | CAT | GCA | TTT | GTC | CAC | TCT |
| GCA | GCA | AGG | CTG | AGA | CGA | GTA | CGT | AAA | CAG | GTG | AGA |
| TCT | ACT | ATG | AGA | AAC | CAC | GAC | AAC | TTG | TAC | TTG | ATC |
| AGA | TGA | TAC | TCT | TTG | GTG | CTG | TTG | AAC | ATG | AAC | TAG |
| TGT | AAC | ACG | AAG | GTC | GAC | AAA | ATT | ATT | GTC | GAA | GAC |
| ACA | TTG | TGC | TTC | CAG | CTG | TTT | TAA | TAA | CAG | CTT | CTG |
| GGA | AGA | GCT | GCT | GCT | GTT | AGA | ACC | GTT | CCA | AGC | AAG |
| CCT | TCT | CGA | CGA | CGA | CAA | TCT | TGG | CAA | GGT | TCG | TTC |
| CCT | TTG | AAC | CCA | AAG | AAG | CCA | AGT | CAC | AAG | ATC | TAC |
| GCA | AAC | TTG | GGT | TTC | TTC | GGT | TCA | GTG | TTC | TAG | ATG |
| CGT | GCT | AGA | AAG | CAA | ATC | TTT | TTG | TCT | TGT | GGT | ACC |
| GCA | CGA | TCT | TTC | GTT | TAG | AAA | AAC | AGA | ACA | CCA | TGG |
| ATC | TCC | TCT | CCA | TTG | GTT | TTG | CAA | AGA | TCC | GGT | TTT |
| TAG | AGG | AGA | GGT | AAC | CAA | AAC | GTT | TCT | AGG | CCA | AAA |
| GGT | GAC | CCA | ATC | AAG | TTG | AGA | GCT | GGT | GTT | AAG | |
| CCA | CTG | GGT | TAG | TTC | AAC | TCT | CGG | CGA | CCA | CAA | TTC |
| CCT | TTG | GTC | AAC | TTG | CCA | GGT | GTC | GGA | AGA | AAC | TTC |
| GGA | AAC | CAG | TTG | AAC | GGT | CCA | CAG | CCT | TCT | TTG | AAG |
| CAA | GAC | CAT | TAT | TGT | TTC | TTC | AGT | CCT | TAC | AGA | ATC |
| GTT | CTG | GTA | ATA | ACA | AAG | AAG | TCA | GGA | ATG | TCT | TAG |
| AAG | CCT | CAG | TAC | GAG | TCT | TTC | GAT | GAC | TTC | GTC | CGT |
| TTC | GCA | GTC | ATG | CTC | AGA | AAG | CTA | CTG | AAG | CAG | GCA |
| GGT | GAT | GCT | GAG | ATT | CAA | AAG | AGA | GTC | GTT | GAC | CAA |
| CCA | CTA | CGA | CTC | TAA | GTT | TTC | TCT | CAG | CAA | CTG | GTT |
| TGG | TAC | GCC | AAT | GGT | ACT | GGT | CCT | CTT | GCC | ACT | AAC |
| ACC | ATG | CGG | TTA | CCA | TGA | CCA | GGA | GAA | CGG | TGA | TTG |
| GGT | ATC | GAA | GCT | GGT | GTC | AAG | ATC | AGA | CCA | ACA | CCA |
| CCA | TAG | CTT | CGA | CCA | CAG | TTC | TAG | TCT | GGT | TGT | GGT |
| GAA | GAA | CTC | TCT | CAA | ATG | GAC | GAA | TCC | TTC | CAG | GAG |
| CTT | CTT | GAG | AGA | GTT | TAC | CTG | CTT | AGG | AAG | GTC | CTC |
| GGT | TAC | AGA | GAA | TAC | TTC | GAA | GAC | AAG | CCA | GAC | AAG |
| CCA | ATG | TCT | CTT | ATG | AAG | CTT | CTG | TTC | GGT | CTG | TTC |
| CCA | GTT | ATG | CAC | TAC | TCC | ATC | ATT | GCT | GGT | TTC | TTC |
| GGT | CAA | TAC | GTG | ATG | AGG | TAG | TAA | CGA | CCA | AAG | AAG |
| GGT | GAC | CAC | ACC | AAG | ATT | CCT | CCT | GGA | AAG | TAC | ATG |
| CCA | CTG | GTG | TGG | TTC | TAA | GGA | GGA | CCT | TTC | ATG | TAC |
| ACT | ATG | TTC | CAC | TTC | TTG | GAA | TAC | CCA | TTC | TCC | AGA |
| TGA | TAC | AAG | GTG | AAG | ACC | CTT | ATG | GGT | AAG | AGG | TCT |
| GGT | TCC | ATT | CAC | ATT | ACC | TCC | CCA | GAC | CCA | TAC | GCA |
| CCA | AGG | TAA | GTG | TAA | TGG | AGG | GGT | CTG | GGT | ATG | CGT |
| GCT | CCA | GAC | TTC | GAC | CGA | GGT | TTC | ATG | AAC | GAT | GAA |
| CGA | GGT | CTG | AAG | CTG | GCT | CCA | AAG | TAC | TTG | CTA | CTT |
| AGA | GAC | ATG | GCT | CCT | ATG | GTT | TGG | GCT | TAC | AAG | TCT |
| TCT | CTG | TAC | CGA | GGA | TAC | CAA | ACC | CGA | ATG | TTC | TTC |
| TCT | AGA | GAA | ACC | GCT | AGA | AGA | AGT | GAC | CAC | TTT | GCC |
| AGA | TCT | CTT | TGG | CGA | TCT | TCT | TCA | CTG | GTG | AAA | CGG |
| GGT | GAG | GTC | ACT | TCT | CAC | CAC | CCT | CTG | TTC | CCA | TAC |
| CCA | CTC | CAG | TGA | AGA | GTG | GTG | GGA | GAC | AGG | GGT | ATG |
| TCA | TCC | GAG | GCC | AGA | GCC | TTG | GAA | ATG | GAT | TTG | GAG |
| AGT | AGG | CTC | CGG | TCT | CGG | AAC | CTT | TAC | CTA | AAC | CTC |
| ACC | TCT | AAT | GCC | TAC | GGT | GGA | CCT | TTG | AAC | TTG | TCT |
| TGG | AGA | TTA | CGG | ATG | CCA | CCT | GGA | AAC | TTG | AAC | AGA |
| GCT | GGT | CTT | GCT | CAC | GGT | TCT | TGG | ACT | CAA | CCT | TTG |
| CGA | CCA | GAA | CGA | GTG | CCA | AGA | ACC | TGA | GTT | GGA | AAC |
| AAG | AAG | CCA | ACT | GCA | AAG | AAC | GAA | GGC | CAC | GIT | ACT |
| TTC | TTC | GGT | TGA | CGT | TTC | TTG | CTT | CCG | GTG | CAA | TGA |
| TCG | AAC | CAG | GTC | GAG | CTT | CAT | CCA | GAC | ATC | GAG | TAC |
| AGC | TTG | GTC | CAG | CTC | GAA | GTA | GGT | CTG | TAG | CTC | ATG |
| GAT | GAG | GAG | GAT | GAC | AAG | GCC | ATT | GAG | ACC | TAC | ATT |
| CTA | CTC | CTC | CTA | CTG | TTC | CGG | TAA | CTC | TTG | ATG | TAA |

-continued

| | | | | | | | | | | |
|---|---|---|---|---|---|---|---|---|---|---|
| CGT | GAG | CAC | ACT | GAG | ACC | ACA | TGG | CAC | TGT | CTG | GGA |
| GCA | CTC | GTG | TGA | CTC | TGG | TGT | ACC | GTG | ACA | CCA | GGT |
| ACC | TGT | TCC | ATC | GGT | CCA | AGA | GAA | GGT | TCC | AAG | ATC |
| TGG | ACA | AGG | TAG | CCA | GGT | TCT | CTT | CCA | AGG | TTC | TAG |
| GTC | AAA | TGG | GGT | GGT | GTT | TIG | GAC | CAC | AGA | TCC | AAC |
| CAG | TTT | ACC | CCA | CCA | CAA | AAC | CTG | GTG | TCT | AGG | TTG |
| GTT | TAC | GGA | GTC | AAG | GGC | TIG | AAG | GTT | GGT | GAC | TTG |
| CAA | ATG | CCT | CAG | TTC | CCG | AAC | TTC | CAA | CCA | CTG | AAC |
| TCC | GTG | TGC | CCA | GAC | AAT | GTT | GGT | TGT | AAC | ACC | TAC |
| AGG | CAC | ACG | GGT | CTG | TTA | CAA | CCA | ACA | TTG | TGG | ATG |
| ACC | ACC | GCT | CTT | TTG | ATC | GGT | GAA | AAG | ACT | GCC | ACT |
| TGG | TGG | CGA | GAA | AAC | TAG | CCA | CTT | TTC | TGA | CGG | TGA |
| TTG | GTT | GGA | GAA | CAT | TTA | GGA | TAC | TCT | GGT | GAG | GCC |
| AAC | CAA | CCT | CTT | CTA | AAT | CCT | ATG | AGA | CCA | CTC | CGG |
| TTA | GAC | ATG | ACT | GTT | CCT | CAG | TTC | AAG | TTG | GGC | ACT |
| AAT | CTG | TAC | TGA | CAA | GGA | GTC | AAG | TTC | AAC | CCG | TGA |
| TAC | GAG | AAG | ACC | GGT | CTT | GCT | AGA | TTC | TAA-3' | | |
| ATG | CTG | TTC | TGG | CCA | GAA | CGA | TCT | AAG | ATT-5' | | |

46. A gene in accordance with claim 43 further comprising flanking regions of chromosomal DNA as characterized by the restriction map in FIG. 2a of the drawings.

47. An isolated *Pichia pastoris* gene coding for the production of polypeptide p76.

48. A gene in accordance with claim 47 wherein said gene is characterized by the restriction map in FIG. 12 of the drawings.

49. A gene in accordance with claim 47 further comprising flanking regions of chromosomal DNA as characterized by the restriction map in FIG. 1a of the drawings.

50. An isolated gene derived from *Pichia pastoris* which upon expression codes for the production of biologically active polypeptide p40 or a biologically active sub-unit thereof.

51. A gene in accordance with claim 50 wherein said gene is characterized by the restriction map in FIG. 14 of the drawings.

52. A gene in accordance with claim 50 further comprising flanking regions of chromosomal DNA as characterized by the restriction map in FIG. 3a of the drawings.

53. A methylotrophic yeast strain which has been transformed with a hybrid plasmid which plasmid comprises:
(1) a 5' regulatory region derived from a gene selected from the group consisting of the alcohol oxidase, p40 and p76 genes obtained from *Pichia pastoris* which regulatory region is responsive to methanol, operably linked to;
(2) a structural gene which encodes a desired polypeptide and which transformed methylotrophic yeast is capable of expressing said desired polypeptide when cultured under suitable conditions for expression.

54. A process for preparing a desired polypeptide comprising:
(1) transforming methylotrophic yeast strain with a hybrid plasmid which contains the 5' region of the p40, p76 or alcohol oxidase genes derived from *Pichia pastoris*, which regulatory region is operably linked to a gene encoding a desired polypeptide, and
(2) culturing the transformed yeast strain in an amount of methanol sufficient to induce expression of the desired polypeptide.

55. A process in accordance with claim 54 further comprising; isolating and purifying said polypeptide.

56. A transformed yeast strain in accordance with claim 53 wherein said transformed yeast strain is selected from the genus Pichia.

57. A transformed yeast strain in accordance with claim 53 wherein said yeast strain is *Pichia pastoris* NRRL Y-15852 (GS115-pSAOH 1).

58. A transformed yeast strain in accordance with claim 53 wherein said yeast strain is *Pichia pastoris* NRRL Y-15853 (GS115-pSAOH 5).

59. A transformed yeast strain in accordance with claim 53 wherein said yeast strain is *Pichia pastoris* NRRL Y-15854 (GS115-pSAOH 10).

60. A transformed yeast strain in accordance with claim 53 wherein said yeast strain is *Pichia pastoris* NRRL Y-15855 (GS115-pTAFH.85).

61. A transformed yeast strain in accordance with claim 53 wherein said yeast strain is *Pichia pastoris* NRRL Y-15856 (GS115-pT76H1).

62. A transformed yeast strain in accordance with claim 53 wherein said yeast strain is *Pichia pastoris* NRRL Y-15857 (GS115-pT76H2).

63. A transformed yeast strain in accordance with claim 53 wherein said yeast strain is *Saccharomyces cerevisiae* NRRL Y-15858 (SEY 2102-pTA013).

64. The hybrid plasmid pPG 6.0.
65. The hybrid plasmid pPG 4.0.
66. The hybrid plasmid pPC 4.8.
67. The hybrid plasmid pPC 15.0.
68. The hybrid plasmid pPC 8.3.
69. The hybrid plasmid pPC 8.0.
70. The hybrid plasmid pPC 6.7.
71. The hybrid plasmid pSAOH 1.
72. The hybrid plasmid pSAOH 5.
73. The hybrid plasmid pSAOH 10.
74. The hybrid plasmid pTAFH 85.
75. The hybrid plasmid pT76H 1.
76. The hybrid plasmid pT76H 2.
77. The hybrid plasmid pT76H 3.
78. The hybrid plasmid pT76H 4.
79. The hybrid plasmid pTAO 13.
80. The hybrid plasmid pT76U 1.

81. An essentially pure culture of *Escherichia coli* NRRL B-15861; MC1061-pSAOH 1.

82. An essentially pure culture of *Escherichia coli* NRRL B-15862; MC1061-pSAOH 5.

83. An essentially pure culture of *Escherichia coli* NRRL B-15863; MC1061-pSAOH 10.

84. An essentially pure culture of *Escherichia coli* NRRL B-15864; MC1061-pTAFH 85.

85. An essentially pure culture of *Escherichia coli* NRRL B-15865; MC1061-pT76H 1.

86. An essentially pure culture of *Escherichia coli* NRRL B-15866; MC1060-pT76H 2.

87. An essentially pure culture of *Escherichia coli* NRRL B-18000; MC1061-pT76H 3.

88. An essentially pure culture of *Escherichia coli* NRRL B-18001; MC1061-pY76H 4.

89. An essentially pure culture of *Escherichia coli* NRRL B-18575; MC1061-pTAO 13.

90. An essentially pure culture of *Escherichia coli* NRRL B-18002; MC1061pT76U1.

91. An essentially pure culture of *Escherichia coli* NRRL B-15867; LE392-pPG 6.0.

92. An essentially pure culture of *Escherichia coli* NRRL B-15868; LE392-pPG 4.0.

93. An essentially pure culture of *Escherichia coli* NRRL B-15869; LE392-pPG 4.8.

94. An essentially pure culture of *Escherichia coli* NRRL B-15870; LE392-pPC 15.0.

95. An essentially pure culture of *Escherichia coli* NRRL B-15871; LE392-pPC 8.3.

96. An essentially pure culture of *Escherichia coli* NRRL B-15873; MM294-pPC 8.0.

97. An essentially pure culture of *Escherichia coli* NRRL B-15872; LE392-pPC 6.7.

98. A process in accordance with claim 54 wherein said transformed yeast strain is a *Pichia* strain consisting of members of the genera:

Candida,
Kloeckera,
Saccharomyces,
Rhodotorula,
Hansenula,
Torulopsis.

* * * * *